US007189565B2

(12) United States Patent
Saatcioglu

(10) Patent No.: US 7,189,565 B2
(45) Date of Patent: Mar. 13, 2007

(54) PROSTATE-SPECIFIC OR TESTIS-SPECIFIC NUCLEIC ACID MOLECULES, POLYPEPTIDES, AND DIAGNOSTIC AND THERAPEUTIC METHODS

(76) Inventor: Fahri Saatcioglu, 26 Halsey Ave., Wellesley, MA (US) 02482

(*) Notice: Subject to any disclaimer, the term of this patent is extended or adjusted under 35 U.S.C. 154(b) by 12 days.

(21) Appl. No.: 10/239,607

(22) PCT Filed: Mar. 23, 2001

(86) PCT No.: PCT/US01/09410

§ 371 (c)(1),
(2), (4) Date: Mar. 20, 2003

(87) PCT Pub. No.: WO01/72962

PCT Pub. Date: Oct. 4, 2001

(65) Prior Publication Data

US 2003/0219761 A1    Nov. 27, 2003

Related U.S. Application Data

(60) Provisional application No. 60/191,929, filed on Mar. 24, 2000.

(51) Int. Cl.
*C12N 15/85* (2006.01)
(52) U.S. Cl. .................. 435/325; 435/320.1; 536/23.1; 536/24.3; 536/24.31; 536/23.5; 530/350
(58) Field of Classification Search ............... 536/23.1, 536/24.3, 23.5, 24.31; 530/350; 435/325, 435/320.1
See application file for complete search history.

(56) References Cited

U.S. PATENT DOCUMENTS

| 5,599,686 A | 2/1997 | Defeo-Jones et al. |
| 5,820,880 A | 10/1998 | Alving et al. |
| 6,048,970 A | 4/2000 | Lal et al. |
| 6,277,972 B1 | 8/2001 | Afar et al. |
| 6,329,503 B1 * | 12/2001 | Afar et al. ................... 530/350 |
| 6,509,458 B1 | 1/2003 | Afar et al. |
| 2002/0187472 A1 | 12/2002 | Lal et al. |
| 2003/0045682 A1 | 3/2003 | Afar et al. |
| 2003/0064397 A1 | 4/2003 | Spancake et al. |

FOREIGN PATENT DOCUMENTS

| WO | WO 99/62941 A2 | 12/1999 |
| WO | WO 99/62941 A3 | 12/1999 |
| WO | WO 00/73509 A2 | 12/2000 |
| WO | WO 01/05970 A2 | 1/2001 |
| WO | WO 01/40276 | 6/2001 |

OTHER PUBLICATIONS

Bowie et al (Science, 1990, 257 : 1306-1310).*
Burgess et al, (Journal of Cell Biology, 1990, 11: 2129-2138).*
Lazar et al. Molecular and Cell Biology, 1988, 8: 1247-1252.*
Tao. et al. The Journal of Immunology, 1989, 143(8): 2595-2601.*
Gillies et al. Human Antibodies and Hybridomas, 1990, 1(1): 47-54.*
Schmid S et al, 2001, J comparative Neurology, 430(2): 160-71.*
Conner et al, 1996, Mol Brain Res, 42: 1-17.*
Brennan et al (Journal of Autoimmunity, 1989, vol. 2 suppl., pp. 177-186).*
Zimmer (Cell Motility and the Cytoskeleton, 1991, vol. 20, pp. 325-337).*
Eriksson et al (Diabetologia, 1992, vol. 35, pp. 143-147).*
Boehringer Mannheim Biochemicals, 1994 Catalog, p. 93.*
MPSRCH search report, 2004, us-10-239-607a-23-copy-1510-1647, pp. 2-4, and us-10-239-607a-14-copy-445-490.rapb, pp. 1-4.*
MPSRCH search report, 2005, us10-239-607a-23.oligo-500.rni, pp. 1-2.*
Dias et al., "Shotgun Sequencing of the Human Transcriptome with ORF Expressed Sequence Tags," *Database EMBL Online*! Database Accession No. AI908168 [XP002279053] (1999).
Diatchenko et al., "Suppression Subtractive Hybridization: A Method for Generating Differentially Regulated or Tissue-Specific cDNA Probes and Libraries," *Proc. Natl. Acad. Sci. USA* 93:6025-6030 (1996).
Isogai et al., "Homo Sapiens cDNA FLJ10829 fis, Clone NT2RP4001138," *Database EMBL Online*! Database Accession No. AK001691 [XP002241852] (2000).
Mahairas et al., "Sequence-Tagged Connectors: A Sequence Approach to Mapping and Scanning the Human Genome," *Proc. Natl. Acad. Sci. USA* 96:9739-9744 (1999).
Watanabe et al., "Protein Kinase N (PKN) and PKN-Related Protein Rhophilin as Targets of Small GTPase Rho," *Science* 271:645-648 (1996).

* cited by examiner

*Primary Examiner*—Susan Ungar
*Assistant Examiner*—Minh-Tam Davis
(74) *Attorney, Agent, or Firm*—Clark & Elbing LLP; Kristina Bieker-Brady

(57) ABSTRACT

The invention provides novel prostate-specific or testis-specific nucleic acid molecules, polypeptides, antibodies, and modulatory compounds for use in methods of diagnosing, treating, and preventing diseases and conditions of the prostate and testis, such as cancer.

10 Claims, 40 Drawing Sheets

Multiple tissue northern blot. Lane 11: Prostate, 12:testis

| SEQ. ID NO. | SEQ. NAME | LENGTH | SEQUENCE |
|---|---|---|---|
| 1 | PSL 22 | 349 | ACTAATGTGAGGAAaCAAACATGTTCAGGCCTGAACATTTCCGGTGCTGACT CGGCcTTAAACGTTTGTGCCATAATGGAAAATATCTATCTATCTGTTCTCAA ATCCTGTTTTTCTCATAGTGTAAACTCACATTTGATGTGTTTTTATGAAGGAA AGTAACCAAGAAACCTCTAGGAATTAGGAAAAAAaGAACTTTTTTGAGGTG TGTTACTATACTGCTGTAAGTTATTTATTATATAAAGTATTGTAAATAGAAaT AGTGTTGAGATATGAAATATGGCTATTTTTAATGGTGACAATTATAGACTTT TAGgTCACTATTAAATTGGGGTTACCTATATCcAGT |
| 2 | PSL 229A | 251 | ACACATCCATCATTGTGAAATCTCTTTTCCAACAAACGTCCTCTTAATGAGC ACAATTCATTAAAaTCTTTGGGGACTAAGCTACGAACAAAGTTCAACTAAAC TACCTACTGACTTCAAAAGGAACATATACCCACCACGTGTGGTAGCTCATG ACTGTAATCCCAGCACTTTGGGAGGCTGAGGCAGGAGGATCACCTGAGCCC AGGAGTTCCAGACCAGCCTAAGCAACATGCCAAGACCCTGTATGT |
| 3 | PSL E15C | 51 | ACAAAGACACCCTTGTYCCCCGGGCAAGGTCCTCCAGCTACAAGGGGGCCA |
| 4 | PSL E156 | 149 | CCXYACATTGTCACAGAGAGGCTCCAGGCTTAAAGTTGACCTGCGTAGAAA GCAAGAATGAATTGTTGGAGGAAGTAAGGAGGGCGATTGAATAAAGACTTT TAGCAGCTGGGCCAGCTGAACCATCCCAACCCTTCAAATCCCCTTGT |
| 5 | PSL E157 | 261 | ACCCTAACTGAACCCATTTCAGCCACTCAGATTGATAGGGTGGAAAAGACA GGGCAGGTGGTAGCAGCTGTGAAGAAAAGAGGAAAGCAGAAGGGTGGCCT ATAATCTACAGGCATGTAGAGAGGACTACATAGGCCTCTGTTCTTTGCCCTC AGGAGCCCCCTTCCTGTCCCTTGGACTCAGAATGATCCTTCCAGCACACAT GGCCCAACACTGAGAGTGCAGGAAGCATGGGTAGGGGCCTCCTGCTGCTGG TATGT |
| 6 | PSL E391 | 121 | AGTNTGNGGGGANTTGAGGGCNGNTACGNNAAANGNTGGNCTACTNTAGA TGCTGCTCGAGCGGCCGCCAGTGTGATGGATACAAGCTTTCTTTTTTTTTTTT ATTTTCGNNTTTTTTTTC |
| 7 | PSL K31 | 93 | ACTCAGTAGGGACTGAGCACTAAATGCTTATTTTAAAAGAAATGTAAAGAG CAGAAAGCAATTCAGGCTACCCTGCCTTTTGTGCTGGCTAGT |
| 8 | PSL L28 | 169 | ACACTTAAAATAGTTAATGTGATACATTTTATGTTACATGTATTTTGCCCAC TGAAAAAATAAAAATATATAAACACACAGCAAATGATGACCAGGCCTTTGA AGAAAGCTTATAAAACAAAATTAAGAAGCCTGGCTACAGAGCGAGACTCTG TCTCAAAAAAAAAAAA |
| 9 | PSL L74 | 262 | ACTTTACAAGCATGAAGGATATTAGGGTAAGTGGCTAATTATAAATCTACT CTAGAGACATATAATCATACAGATTATTCATAAAATTTTTCAGTGCTGTCCT TCCACATTTAATTGCATTTTGCTCAAACTGTAGAATGCCCTACATTCCCCCC ACCCCAATTTGCTATTTCCTTATTAAAATAGAAAATTATAGGCAAGATACAA TTATATGCGTTCCTCTTCCTGAAATTATAACATTTCTAAACTTACCCACGTAG GT |
| 10 | PSL SSH 20 | 175 | ACAGGTTGGCCCTTCACCTAGTTGACTCAGCCCTCGATAGTCTAGAGCCCAC CCCCTCCTCAGGAACTCAAGAGCTCAGCATTTATAATGAGCAGTTGGTAAT GAGTTGCCCTATGTGCTTGTCGCAAGCAGTCACAGAGATGAGCCCTATTACT TGATATTCAGGAACAAAGGT |
| 11 | PSL SSH 4 | 331 | ACATCCAAGCCTTCCTCTGCGTGAGAGCAAAGGCTTTGCTCATCAGCCAGCC AGTCTTGTTACTATCTGGCTACTTTTTAAGGTTAAAAAATAAAAGGCAGTTT CTTTGCTCTGCAGGCGGCAAGGCAGGAGGCGCAGGCCTTCTTCATTGTTCAC ATGTCACAGGAGGAGGCTCTGAGCAAAGGCCACTGGCAAGTTAGGGCAAC ACCAAGAAGGCTCTGCGGAGAGACTCCCTGTGGGTTGGGGGsCTGGCAGGA ACGGTGCcTGTGGACTGTTTATGGTCTGTCCAGTTGAGGCTTGGTAAACCCA AGTAAAGTGTTAAAAACCTCAGT |
| 12 | PSL SSH 9 | 170 | ACGACTCATCCACCTCCGGCTGAAGCTCCAGGAGCTGAAGGACCCCAATGA GGATGAGCCAAACATCCGAGTGCTCCTTGAGCACCGCTTTTACAAGGAGAA GAGCAAGAGCGTCAAGCAGACCTGTGACAAGTGTAACACCATCATCTGGGG GCTCATTCAGACCTGGT |

```
EXON_1  83bp
     1  ACGCGGGGATCCAGCTTGGGTAGGCGGGGAAGCAGCTGGAGTGCGACCGCTACGGCAGC
    61  CACCCTGCAACCGCCAGTCGGAG

EXON_2  61bp
     1  AGCTAAGGGCAAGTCCTGAGGTTGGGCCCAGGAGAAAGAAGGCAAGGAGACATTGTCCCA
    61  G

EXON_3  525bp
     1  GATATTCTTGGTGATCTTGGAAGTGTCCGTATCATGGAATCAATCTCTATGATGGGAAGC
    61  CCTAAGAGCCTTAGTGAAACTTTTTTACCTAATGGCATAAATGGTATCAAAGATGCAAGG
   121  AAGGTCACTGTAGGTGTGATTGGAAGTGGAGATTTTGCCAAATCCTTGACCATTCGACTT
   181  ATTAGATGCGGCTATCATGTGGTCATAGGAAGTAGAAATCCTAAGTTTGCTTCTGAATTT
   241  TTTCCTCATGTGGTAGATGTCACTCATCATGAAGATGCTCTCACAAAAACAAATATAATA
   301  TTTGTTGCTATACACAGAGAACATTATACCTCCCTGTGGGACCTGAGACATCTGCTTGTG
   361  GGTAAAATCCTGATTGATGTGAGCAATAACATGAGGATAAACCAGTACCCAGAATCCAAT
   421  GCTGAATATTTGGCTTCATTATTCCCAGATTCTTGATTGTCAAAGGATTTAATGTTGTC
   481  TCAGCTTGGGCACTTCAGTTAGGACCTAAGGATGCCAGCCGGCAG

EXON_4  528bp
     1  GTTTATATATGCAGCAACAATATTCAAGCGCGACAACAGGTTATTGAACTTGCCGGCCAG
    61  TTGAATTTCATTCCCATTGACTTGGGATCCTTATCATCAGCCAGAGAGATTGAAAATTTA
   121  CCCCTACGACTCTTTACTCTCTGGAGAGGGCCAGTGGTGGTAGCTATAAGCTTGGCCACA
   181  TTTTTTTTCCTTTATTCCTTTGTCAGAGATGTGATTCATCCATATGCTAGAAACCAACAG
   241  AGTGACTTTTACAAAATTCCTATAGAGATTGTGAATAAAACCTTACCTATAGTTGCCATT
   301  ACTTTGCTCTCCCTAGTATACCTCGCAGGTCTTCTGGCAGCTGCTTATCAACTTATTAC
   361  GGCACCAAGTATAGGAGATTTCCACCTTGGTTGGAAACCTGGTTACAGTGTAGAAAACAG
   421  CTTGGATTACTAAGTTTTTTCTTCGCTATGGTCCATGTTGCCTACAGCCTCTGCTTACCG
   481  ATGAGAAGGTCAGAGAGATATTTGTTTCTCAACATGGCTTATCAGCAG

EXON_5  165bp
     1  GTTCATGCAAATATTGAAAACTCTTGGAATGAGGAAGAAGTTTGGAGAATTGAAATGTAT
    61  ATCTCCTTTGGCATAATGAGCCTTGGCTTACTTTCCCTCCTGGCAGTCACTTCTATCCCT
   121  TCAGTGAGCAATGCTTTAAACTGGAGAGAATTCAGTTTTATTCAG

EXON_6  148bp
     1  TCTACACTTGGATATGTCGCTCTGCTCATAAGTACTTTCCATGTTTTAATTTATGGATGG
    61  AAACGAGCTTTTGAGGAAGAGTACTACAGATTTTTATACACCACCAAACTTTGTTCTTGCT
   121  CTTGTTTTGCCCTCAATTGTAATTCTGG cont_6+UTR
     1  GTAAGATTATTTTATTCCTTCCATGTATAAGCCGAAAGCTAAAACGAATTAAAAAGGCT
    61  GGGAAAAGAGCCAATTTCTGGAAGAAGGTATTGGAGGAACAATTCCTCATGTCTCCCGG
   121  AGAGGGTCACAGTAATGTGATGATAAATGGTGTTCACAGCTGCCATATAAAGTTCTACTC
   181  ATGCCATTATTTTATGACTTCTACGTTCAGTTACAAGTATGCTGTCAAATTATCGTGGG
   241  TTGAAACTTGTTAAATGAGATTTCAACTGACTTAGTGATAGAGTTTTCTTCAAGTTAATT
   301  TTCACAAATGTCATGTTTGCCAATATGAATTTTCTAGTCAACATATTATTGTAATTTAG
   361  GTATGTTTTGTTTTGTTTTGCACAACTGTAACCCTGTTGTTACTTTATATTTCATAATCA
   421  GACAAAAATACTTACAGTTAATAATATAGATATAATGTTAAAAACAATTTGCAAACCAGC
   481  AGAATTTTAAGCTTTTAAAATAATTCAATGGATATACATTTTTTTCTGAAGATTAAGATT
   541  TTAATTATTCAACTTAAAAAGTAGAAATGCATTATTATACATTTTTTTAAGAAAGGACAC
   601  GTTATGTTAGCATCTAGGTAAGGCTGCATGATAGCATTCCTATATTTCTCTCATAAAATA
   661  GGATTTGAAGGATGAAATTAATTGTATGAAGCAATGTGATTATATGAAGAGACACAAATT
   721  AAAAAGACAAATTAAACCTGAAATTATATTTAAAATATATTTGAGACATGAAATACATAC
   781  TGATAATACATACCTCATGAAAGATTTTATTCTTTATTGTGTTACAGAGCAGTTTCATTT
   841  TCATATTAATATACTGATCAGGAAGAGGATTCAGTAACATTTGGCTTCCAAAACTGCTAT
   901  CTCTAATACGGTACCAATCCTAGGAACTGTATACTAGTTCCTACTTAGAACAAAAGTATC
```

```
 961 AAGTTTGCACACAAGTAATCTGCCAGCTGACCTTTGTCGCACCTTAACCAGTCACCACTT
1021 GCTATGGTATAGGATTATACTGATGTTCTTTGAGGGATTCTGATGTGCTAGGCATGGTTC
1081 TAAGTACTTTACTTGTATTATCCCATTTAATACTTAGAACAACCCCGTGAGATAAGTAGT
1141 TATTATCCTCATTTTACACATGAGGGACCGAAGGATAGAAAAGTTATTTTTCAAAGGTCT
1201 TGCAGTTAATAAATGGCAGAGTGAGCATTCAAGTCCAGGTAGTCATATTCCAGAGGCCAC
1261 GGTTTTAACCACTAGGCTCTAGAGCTCCCGCCGCGCCCCTATGCATTATGTTCACAATGC
1321 CAATCTAGATGCTTCCTCTTTTGTATAAAGTCACTGACATTCTTTAGAGTGGGTTGGGTG
1381 CATCCAAAAATGTATAAAAATATTATTATAATAAACTTATTACTGCTTGTAGGGTAATTC
1441 ACAGTTACTTACCCTATTCTTGCTTGGAACATGAGCCTGGAGACCCATGGCAGTCCATAT
1501 GCCTCCCTATGCAGTGAAGGGCCCTAGCAGTGTTAACAAATTGCTGAGATCCCACGGAGT
1561 CTTTCAAAAATCTCTGTAGAGTTAGTCTTCTCCTTTTCTCTTCCTGAGAAGTTCTCCTGC
1621 CTGCATAACCATTCATTAGGGAGTACTTTACAAGCATGAAGGATATTAGGGTAAGTGGCT
1681 AATTATAAATCTACTCTAGAGACATATAATCATACAGATTATTCATAAAATTTTTCAGTG
1741 CTGTCCTTCCACATTTAATTGCATTTTGCTCAAACTGTAGAATGCCCTACATTCCCCCCA
1801 CCCCAATTTGCTATTTCCTTATTAAAATAGAAAATTATAGGCAAGATACAATTATATGCG
1861 TTCCTCTTCCTGAAATTATAACATTTCTAAACTTACCCACGTAGGGACTACTGAATCCAA
1921 CTGCCAACAATAAAAAGACTTTTATTTAGTAGAGGCTACCTTTCCCCCCAGTGACTCTTT
1981 TTCTACAACTGCCTTGTCAGTTTGGTAATTCACTTATGATTTTCTAATGTTCTCTTGGTG
2041 AATTTTATTATCTTGGACCCTCTTTTTTTTTTTTTTTAAAGACAGAGTCTTGCTCTGTCA
2101 CCCATTGCTCTCGTTTGGGCAACAAGAGTGAAACTCTTGTCTCAAAAAAAAAAAAAAATG
2161 AGGTTTAAGACAGTTTTGTCATTACTGGTGGGATCTGGTCACACAAGATAGCATTAAACG
2221 TGACATGGCACATAAAATTGGTTAAAAAATTTTGTTTTTTAATTGCGTAATGTAAAAGCC
2281 CAACAAACACTTTATGCAAGATTGGAATGTATCTTCAAATTCAGATTTAATAAACATGTA
2341 AAGATCCTCTGTAAAAAAAAAAAAAAAAAAAAAAAAAAAAAA
```

FIGURE 4C

```
   1 ACGCGGGGGATCCAGCTTGGGTAGGCGGGGAAGCAGCTGGAGTGCGACCGCTACGGCAGC
  61 CACCCTGCAACCGCCAGTCGGAGAGCTAAGGGCAAGTCCTGAGGTTGGGCCCAGGAGAAA
 121 GAAGGCAAGGAGACATTGTCCCAGGATATTCTTGGTGATCTTGGAAGTGTCCGTATCATG
 181 GAATCAATCTCTATGATGGGAAGCCCTAAGAGCCTTAGTGAAACTTGTTTACCTAATGGC
 241 ATAAATGGTATCAAAGATGCAAGGAAGGTCACTGTAGGTGTGATTGGAAGTGGAGATTTT
 301 GCCAAATCCTTGACCATTCGACTTATTAGATGCGGCTATCATGTGGTCATAGGAAGTAGA
 361 AATCCTAAGTTTGCTTCTGAATTTTTTCCTCATGTGGTAGATGTCACTCATCATGAAGAT
 421 GCTCTCACAAAAACAAATATAATATTTGTTGCTATACACAGAGAACATTATACCTCCCTG
 481 TGGGACCTGAGACATCTGCTTGTGGGTAAAATCCTGATTGATGTGAGCAATAACATGAGG
 541 ATAAACCAGTACCCAGAATCCAATGCTGAATATTTGGCTTCATTATTCCCAGATTCTTTG
 601 ATTGTCAAAGGATTTAATGTTGTCTCAGCTTGGGCACTTCAGTTAGGACCTAAGGATGCC
 661 AGCCGGCAGGTTTATATATGCAGCAACAATATTCAAGCGCGACAACAGGTTATTGAACTT
 721 GCCCGCCAGTTGAATTTCATTCCCATTGACTTGGGATCCTTATCATCAGCCAGAGAGATT
 781 GAAAATTTACCCCTACGACTCTTTACTTTCTGGAGAGGGCCAGTGGTGGTAGCTATAAGC
 841 TTGGCCACATTTTTTTTCCTTTATTCCTTTGTCAGAGATGTGATTCATCCATATGCTAGA
 901 AACCAACAGAGTGACTTTTACAAAATTCCTATAGAGATTGTGAATAAAACCTTACCTATA
 961 GTTGCCATTACTTTGCTCTCCCTAGTATACCTTGCAGGTCTTCTGGCAGCTGCTTATCAA
1021 CTTTATTACGGCACCAAGTATAGGAGATTTCCACCTTGGTTGGAAACCTGGTTACAGTGT
1081 AGAAAACAGCTTGGATTACTAAGTTTTTTCTTCGCTATGGTCCATGTTGCCTACAGCCTC
1141 TGCTTACCGATGAGAAGGTCAGAGAGATATTTGTTTCTCAACATGGCTTATCAGCAGGTT
1201 CATGCAAATATTGAAACTCTTGAATGAGGAAGAAGTTTGGAGAATTGAAATGTATATC
1261 TCCTTTGGCATAATGAGCCTTGGCTTACTTTCCCTCCTGGCAGTCACTTCTATCCCTTCA
1321 GTGAGCAATGCCTTAAACTGGAGAGAATTCAGTTTTATTCAGTCTACACTTGGATATGTC
1381 GCTCTGCTCATAAGTACTTTCCATGTTTTAATTTATGGATGGAAACGAGCTTTTGAGGAA
1441 GAGTACTACAGATTTTATACACCACCAAACTTTGTTCTTGCTCTTGTTTTGCCCTCAATT
1501 GTAATTCTGGGTAAGATTATTTTATTCCTTCCATGTATAAGCCGAAAGCTAAAACGAATT
1561 AAAAAAGGCTGGGAAAAGAGCCAATTTCTGGAAGAAGGTATTGGAGGAACAATTCCTCAT
1621 GTCTCCCCGGAGAGGGTCACAGTAATGTGATGATAAATGGTGTTCACAGCTGCCATATAA
1681 AGTTCTACTCATGCCATTATTTTTATGACTTCTACGTTCAGTTACAAGTATGCTGTCAAA
1741 TTATCGTGGGTTGAAACTTGTTAAATGAGATTTCAACTGACTTAGTGATAGAGTTTTCTT
1801 CAAGTTAATTTTCACAAATGTCATGTTTGCCAATATGAATTTTTCTAGTCAACATATTAT
1861 TGTAATTTAGGTATGTTTTGTTTTGTTTTGCACAACTGTAACCCTGTTGTTACTTTATAT
1921 TTCATAATCAGACAAAAATACTTACAGTTAATAATATAGATATAATGTTAAAAACAATTT
1981 GCAAACCAGCAGAATTTTAAGCTTTTAAAATAATTCAATGGATATACATTTTTTTCTGAA
2041 GATTAAGATTTTAATTATTCAACTTAAAAAGTAGAAATGCATTATTATACATTTTTTTAA
2101 GAAAGGACACGTTATGTTAGCATCTAGGTAAGGCTGCATGATAGCATTCCTATATTTCTC
2161 TCATAAAATAGGATTTGAAGGATGAAATTAATTGTATGAAGCAATGTGATTATATGAAGA
2221 GACACAAATTAAAAAGACAAATTAAACCTGAAATTATATTTAAAATATATTTGAGACATG
2281 AAATACATACTGATAATACATACCTCATGAAAGATTTTATTCTTTATTGTGTTACAGAGC
2341 AGTTTCATTTTCATATTAATATACTGATCAGGAAGAGGATTCAGTAACATTTGGCTTCCA
2401 AAACTGCTATCTCTAATACGGTACCAATCCTAGGAACTGTATACTAGTTCCTACTTAGAA
2461 CAAAAGTATCAAGTTTGCACACAAGTAATCTGCCAGCTGACCTTTGTCGCACCTTAACCA
2521 GTCACCACTTGCTATGGTATAGGATTATACTGATGTTCTTTGAGGGATTCTGATGTGCTA
2581 GGCATGGTTCTAAGTACTTTACTTGTATTATCCCATTTAATACTTAGAACAACCCCGTGA
2641 GATAAGTAGTTATTATCCTCATTTTACACATGAGGGACCGAAGGATAGAAAAGTTATTTT
2701 TCAAAGGTCTTGCAGTTAATAAATGGCAGAGTGAGCATTCAAGTCCAGGTAGTCATATTC
2761 CAGAGGCCACGGTTTTAACCACTAGGCTCTAGAGCTCCCGCCGCGCCCCTATGCATTATG
2821 TTCACAATGCCAATCTAGATGCTTCCTCTTTTGTATAAAGTCACTGACATTCTTTAGAGT
2881 GGGTTGGGTGCATCCAAAAATGTATAAAAATATTATTATAATAAACTTATTACTGCTTGT
2941 AGGGTAATTCACAGTTACTTACCCTATTCTTGCTTGGAACATGAGCCTGGAGACCCATGG
3001 CAGTCCATATGCCTCCCTATGCAGTGAAGGGCCCTAGCAGTGTTAACAAATTGCTGAGAT
3061 CCCACGGAGTCTTTCAAAAATCTCTGTAGAGTTAGTCTTCTCCTTTTCTCTTCCTGAAA
3121 GTTCTCCTGCCTGCATAACCATTCATTAGGGAGTACTTTACAAGCATGAAGGATATTAGG
3181 GTAAGTGGCTAATTATAAATCTACTCTAGAGACATATAATCATACAGATTATTCATAAAA
3241 TTTTTCAGTGCTGTCCTTCCACATTTAATTGCATTTGCTCAAACTGTAGAATGCCCTAC
3301 ATTCCCCCCACCCCAATTTGCTATTTCCTTATTAAAAATGTATAAAAATATTATTATAAT
3361 AAACTTATTACTGCTTGTAGGGTAATTCACAGTTACTTACCCTATTCTTGCTTGGAACAT
```

```
3421 GAGCCTGGAGACCCATGGCAGTCCATATGCCTCCCTATGCAGTGAAGGGCCCTAGCAGTG
3481 TTAACAAATTGCTGAGATCCCACGGAGTCTTTCAAAAATCTCTGTAGAGTTAGTCTTCTC
3541 CTTTTCTCTTCCTGAGAAGTTCTCCTGCCTGCATAACCATTCATTAGGGAGTACTTTACA
3601 AGCATGAAGGATATTAGGGTAAGTGGCTAATTATAAATCTACTCTAGAGACATATAATCA
3661 TACAGATTATTCATAAAATTTTTCAGTGCTGTCCTTCCACATTTAATTGCATTTTGCTCA
3721 AACTGTAGAATGCCCTACATTCCCCCCACCCCAATTTGCTATTTCCTTATTAAAATAGAA
3781 AATTATAGGCAAGATACAATTATATGCGTTCCTCTTCCTGAAATTATAACATTTCTAAAC
3841 TTACCCACGTAGGGACTACTGAATCCAACTGCCAACAATAAAAAGACTTTTATTTAGTAG
3901 AGGCTACCTTTCCCCCCAGTGACTCTTTTTCTACAACTGCCTTGTCAGTTTGGTAATTCA
3961 CTTATGATTTTCTAATGTTCTCTTGGTGAATTTTATTATCTTGGACCCTCTTTTTTTTTT
4021 TTTTTAAAGACAGAGTCTTGCTCTGTCACCCATTGCTCTCGTTTGGGCAACAAGAGTGAA
4081 ACTCTTGTCTCAAAAAAAAAAAAAAATGAGGTTTAAGACAGTTTTGTCATTACTGGTGGG
4141 ATCTGGTCACACAAGATAGCATTAAACGTGACATGGCACATAAAATTGGTTAAAAAATTT
4201 TGTTTTTTAATTGCGTAATGTAAAAGCCCAACAAACACTTTATGCAAGATTGGAATGTAT
4261 CTTCAAATTCAGATTTAATAAACATGTAAAGATCCTCTGTAAAAAAAAAAAAAAAAAAAA
4321 AAAAAAAAA
```

FIGURE 4D

```
  1 ACGCGGGGGATCCAGCTTGGGTAGGCGGGGAAGCAGCTGGAGTGCGACCGCTACGGCAGC
 61 CACCCTGCAACCGCCAGTCGGAGAGCTAAGGGCAAGTCCTGAGGTTGGGCCCAGGAGAAA

1                                                             M
121 GAAGGCAAGGAGACATTGTCCCAGGATATTCTTGGTGATCTTGGAAGTGTCCGTATCATG

2   E  S  I  S  M  M  G  S  P  K  S  L  S  E  T  C  L  P  N  G
181 GAATCAATCTCTATGATGGGAAGCCCTAAGAGCCTTAGTGAAACTTGTTTACCTAATGGC

22   I  N  G  I  K  D  A  R  K  V  T  V  G  V  I  G  S  G  D  F
241 ATAAATGGTATCAAAGATGCAAGGAAGGTCACTGTAGGTGTGATTGGAAGTGGAGATTTT

42   A  K  S  L  T  I  R  L  I  R  C  G  Y  H  V  V  I  G  S  R
301 GCCAAATCCTTGACCATTCGACTTATTAGATGCGGCTATCATGTGGTCATAGGAAGTAGA

62   N  P  K  F  A  S  F  F  P  H  V  V  D  V  T  H  H  E  D
361 AATCCTAAGTTTGCTTCTGAATTTTTTCCTCATGTGGTAGATGTCACTCATCATGAAGAT

82   A  L  T  K  T  N  I  I  F  V  A  I  H  R  E  H  Y  T  S  L
421 GCTCTCACAAAAACAAATATAATATTTGTTGCTATACACAGAGAACATTATACCTCCCTG

102   W  D  L  R  H  L  L  V  G  K  I  L  I  D  V  S  N  N  M  R
481 TGGGACCTGAGACATCTGCTTGTGGGTAAAATCCTGATTGATGTGAGCAATAACATGAGG

122   I  N  Q  Y  P  E  S  N  A  E  Y  L  A  S  L  F  P  D  S  L
541 ATAAACCAGTACCCAGAATCCAATGCTGAATATTTGGCTTCATTATTCCCAGATTCTTTG

142   I  V  K  G  F  N  V  V  S  A  W  A  L  Q  L  G  P  K  D  A
601 ATTGTCAAAGGATTTAATGTTGTCTCAGCTTGGGCACTTCAGTTAGGACCTAAGGATGCC

162   S  R  Q  V  Y  I  C  S  N  N  I  Q  A  R  Q  Q  V  I  E  L
661 AGCCGGCAGGTTTATATATGCAGCAACAATATTCAAGCGCGACAACAGGTTATTGAACTT

182   A  R  Q  L  N  F  I  P  I  D  L  G  S  L  S  S  A  R  E  I
721 GCCCGCCAGTTGAATTTCATTCCCATTGACTTGGGATCCTTATCATCAGCCAGAGAGATT

202   E  N  L  P  L  R  L  F  T  F  W  R  G  P  V  V  V  A  I  S
781 GAAAATTTACCCCTACGACTCTTTACTTTCTGGAGAGGGCCAGTGGTGGTAGCTATAAGC

222   L  A  T  F  F  F  L  Y  S  F  V  R  D  V  I  H  P  Y  A  R
841 TTGGCCACATTTTTTTTTCCTTTATTCCTTTGTCAGAGATGTGATTCATCCATATGCTAGA

242   N  Q  Q  S  D  F  Y  K  I  P  I  E  I  V  N  K  T  L  P  I
901 AACCAACAGAGTGACTTTTACAAAATTCCTATAGAGATTGTGAATAAAACCTTACCTATA

262   V  A  I  T  L  L  S  L  V  Y  L  A  G  L  L  A  A  A  Y  Q
961 GTTGCCATTACTTTGCTCTCCCTAGTATACCTTGCAGGTCTTCTGGCAGCTGCTTATCAA

282   L  Y  Y  G  T  K  Y  R  R  F  P  P  W  L  E  T  W  L  Q  C
1021 CTTTATTACGGCACCAAGTATAGGAGATTTCCACCTTGGTTGGAAACCTGGTTACAGTGT

302   R  K  Q  L  G  L  L  S  F  F  A  M  V  H  V  A  Y  S  L
1081 AGAAAACAGCTTGGATTACTAAGTTTTTTCTTCGCTATGGTCCATGTTGCCTACAGCCTC

322   C  L  P  M  R  R  S  E  R  Y  L  F  L  N  M  A  Y  Q  Q  V
1141 TGCTTACCGATGAGAAGGTCAGAGAGATATTTGTTTCTCAACATGGCTTATCAGCAGGTT
```

```
342  H   A   N   I   E   N   S   W   N   E   E   V   W   R   I   E   M   Y   I
1201 CATGCAAATATTGAAAACTCTTGGAATGAGGAAGAAGTTTGGAGAATTGAAATGTATATC

362  S   F   G   I   M   S   L   G   L   L   S   L   L   A   V   T   S   I   P   S
1261 TCCTTTGGCATAATGAGCCTTGGCTTACTTTCCCTCCTGGCAGTCACTTCTATCCCTTCA

382  V   S   N   A   L   N   W   R   E   F   S   F   I   Q   S   T   L   G   Y   V
1321 GTGAGCAATGCCTTAAACTGGAGAGAATTCAGTTTTATTCAGTCTACACTTGGATATGTC

402  A   L   L   I   S   T   F   H   V   L   I   Y   G   W   K   R   A   F   E   E
1381 GCTCTGCTCATAAGTACTTTCCATGTTTTAATTTATGGATGGAAACGAGCTTTTGAGGAA

422  E   Y   Y   R   F   Y   T   P   P   N   F   V   L   A   L   V   L   P   S   I
1441 GAGTACTACAGATTTTATACACCACCAAACTTTGTTCTTGCTCTTGTTTTGCCCTCAATT

442  V   I   L   G   K   I   I   L   F   L   P   C   I   S   R   K   L   K   R   I
1501 GTAATTCTGGGTAAGATTATTTTATTCCTTCCATGTATAAGCCGAAAGCTAAAACGAATT

462  K   K   G   W   E   K   S   Q   F   L   E   E   G   I   G   G   T   I   P   H
1561 AAAAAAGGCTGGGAAAAGAGCCAATTTCTGGAAGAAGGTATTGGAGGAACAATTCCTCAT

482  V   S   P   E   R   V   T   V   M   *
1621 GTCTCCCCGGAGAGGGTCACAGTAATGTGATGATAAATGGTGTTCACAGCTGCCATATAA
```

FIGURE 4E

```
EXON_1   75bp
     1   GATCCAGCTTGGGTAGGCGGGGAAGCAGCTGGAGTGCGACCGCCGCGGCAGCCACCCTGC
    61   AACCGCCAGTCGGAG

EXON_2   79bp
     1   AGAGCTAAGGGCAAGTCCTGAGGTTGGGCCCAGGAGAAAGAAGGCAAGGAGACATTGTCC
    61   CAGGTAGGATGTGTCCCAG

EXON_3   525bp
     1   GATATTCTTGGTGATCTTGGAAGTGTCCGTATCATGGAATCAATCTCTATGATGGGAAGC
    61   CCTAAGAGCCTTAGTGAAACTTTTTTACCTAATGGCATAAATGGTATCAAAGATGCAAGG
   121   AAGGTCACTGTAGGTGTGATTGGAAGTGGAGATTTTGCCAAATCCTTGACCATTCGACTT
   181   ATTAGATGCGGCTATCATGTGGTCATAGGAAGTAGAAATCCTAAGTTTGCTTCTGAATTT
   241   TTTCCTCATGTGGTAGATGTCACTCATCATGAAGATGCTCTCACAAAAACAAATATAATA
   301   TTTGTTGCTATACACAGAGAACATTATACCTCCCTGTGGGACCTGAGACATCTGCTTGTG
   361   GGTAAAATCCTGATTGATGTGAGCAATAACATGAGGATAAACCAGTACCCAGAATCCAAT
   421   GCTGAATATTTGGCTTCATTATTCCCAGATTCTTTGATTGTCAAAGGATTTAATGTTGTC
   481   TCAGCTTGGGCACTTCAGTTAGGACCTAAGGATGCCAGCCGGCAG

EXON_4   528bp
     1   GTTTATATATGCAGCAACAATATTCAAGCGCGACAACAGGTTATTGAACTTGCCCGCCAG
    61   TTGAATTTCATTCCCATTGACTTGGGATCCTTATCATCAGCCAGAGAGATTGAAAATTTA
   121   CCCCTACGACTCTTTACTCTCTGGAGAGGGCCAGTGGTGGTAGCTATAAGCTTGGCCACA
   181   TTTTTTTTCCTTTATTCCTTTGTCAGAGATGTGATTCATCCATATGCTAGAAACCAACAG
   241   AGTGACTTTTACAAAATTCCTATAGAGATTGTGAATAAAACCTTACCTATAGTTGCCATT
   301   ACTTTGCTCTCCCTAGTATACCTCGCAGGTCTTCTGGCAGCTGCTTATCAACTTTATTAC
   361   GGCACCAAGTATAGGAGATTTCCACCTTGGTTGGAAACCTGGTTACAGTGTAGAAAACAG
   421   CTTGGATTACTAAGTTTTTTCTTCGCTATGGTCCATGTTGCCTACAGCCTCTGCTTACCG
   481   ATGAGAAGGTCAGAGAGATATTTGTTTCTCAACATGGCTTATCAGCAG

EXON_5   165bp
     1   GTTCATGCAAATATTGAAAACTCTTGGAATGAGGAAGAAGTTTGGAGAATTGAAATGTAT
    61   ATCTCCTTTGGCATAATGAGCCTTGGCTTACTTTCCCTCCTGGCAGTCACTTCTATCCCT
   121   TCAGTGAGCAATGCTTTAAACTGGAGAGAATTCAGTTTTATTCAG

EXON_6   148bp
     1   TCTACACTTGGATATGTCGCTCTGCTCATAAGTACTTTCCATGTTTTAATTTATGGATGG
    61   AAACGAGCTTTTGAGGAAGAGTACTACAGATTTTATACACCACCAAACTTTGTTCTTGCT
   121   CTTGTTTTGCCCTCAATTGTAATTCTGG

EXON_7+UTR   718bp
     1   ATCTTTTGCAGCTTTGCAGATACCCAGACTGAGCTGGAACTGGAATTTGTCTTCCTATTG
    61   ACTCTACTTCTTTAAAAGCGGCTGCCCATTACATTCCTCAGCTGTCCTTGCAGTTAGGTG
   121   TACATGTGACTGAGTGTTGGCCAGTGAGATGAAGTCTCCTCAAAGGAAGGCAGCATGTGT
   181   CCTTTTTCATCCCTTCATCTTGCTGCTGGGATTGTGGATATAACAGGAGCCCTGGCAGCT
   241   GTCTCCAGAGGATCAAAGCCACACCCAAAGAGTAAGGCAGATTAGAGACCAGAAAGACCT
   301   TGACTACTTCCCTACTTCCACTGCTTTTTCCTGCATTTAAGCCATTGTAAATCTGGGTGT
   361   GTTACATGAAGTGAAAATTAATTCTTTCTGCCCTTCAGTTCTTTATCCTGATACCATTTA
   421   ACACTGTCTGAATTAACTAGACTGCAATAATTCTTTCTTTTGAAAGCTTTTAAAGGATAA
   481   TGTGCAATTCACATTAAAATTGATTTTCCATTGTCAATTAGTTATACTCATTTTCCTGCC
   541   TTGATCTTTCATTAGATATTTTGTATCTGCTTGGAATATATTATCTTCTTTTTAACTGTG
   601   TAATTGGTAATTACTAAAACTCTGTAATCTCCAAAATATTGCTATCAAATTACACACCAT
   661   GTTTTCTATCATTCTCATAGATCTGCCTTATAAACATTTAAATAAAAAGTACTATTTA
```

FIGURE 4F

```
   1 GATCCAGCTTGGGTAGGCGGGGAAGCAGCTGGAGTGCGACCGCCGCGGCAGCCACCCTGC
  61 AACCGCCAGTCGGAGAGAGCTAAGGGCAAGTCCTGAGGTTGGGCCCAGGAGAAAGAAGGC
 121 AAGGAGACATTGTCCCAGGTAGGATGTGTCCCAGGATATTCTTGGTGATCTTGGAAGTGT
 181 CCGTATCATGGAATCAATCTCTATGATGGGAAGCCCTAAGAGCCTTAGTGAAACTTTTTT
 241 ACCTAATGGCATAAATGGTATCAAAGATGCAAGGAAGGTCACTGTAGGTGTGATTGGAAG
 301 TGGAGATTTTGCCAAATCCTTGACCATTCGACTTATTAGATGCGGCTATCATGTGGTCAT
 361 AGGAAGTAGAAATCCTAAGTTTGCTTCTGAATTTTTTCCTCATGTGGTAGATGTCACTCA
 421 TCATGAAGATGCTCTCACAAAAACAAATATAATATTTGTTGCTATACACAGAGAACATTA
 481 TACCTCCCTGTGGGACCTGAGACATCTGCTTGTGGGTAAAATCCTGATTGATGTGAGCAA
 541 TAACATGAGGATAAACCAGTACCCAGAATCCAATGCTGAATATTTGGCTTCATTATTCCC
 601 AGATTCTTTGATTGTCAAAGGATTTAATGTTGTCTCAGCTTGGGCACTTCAGTTAGGACC
 661 TAAGGATGCCAGCCGGCAGGTTTATATATGCAGCAACAATATTCAAGCGCGACAACAGGT
 721 TATTGAACTTGCCCGCCAGTTGAATTTCATTCCCATTGACTTGGGATCCTTATCATCAGC
 781 CAGAGAGATTGAAAATTTACCCCTACGACTCTTTACTCTCTGGAGAGGGCCAGTGGTGGT
 841 AGCTATAAGCTTGGCCACATTTTTTTTCCTTTATTCCTTTGTCAGAGATGTGATTCATCC
 901 ATATGCTAGAAACCAACAGAGTGACTTTTACAAAATTCCTATAGAGATTGTGAATAAAAC
 961 CTTACCTATAGTTGCCATTACTTTGCTCTCCCTAGTATACCTCGCAGGTCTTCTGGCAGC
1021 TGCTTATCAACTTTATTACGGCACCAAGTATAGGAGATTTCCACCTTGGTTGGAAACCTG
1081 GTTACAGTGTAGAAAACAGCTTGGATTACTAAGTTTTTTCTTCGCTATGGTCCATGTTGC
1141 CTACAGCCTCTGCTTACCGATGAGAAGGTCAGAGAGATATTTGTTTCTCAACATGGCTTA
1201 TCAGCAGGTTCATGCAAATATTGAAAACTCTTGGAATGAGGAAGAAGTTTGGAGAATTGA
1261 AATGTATATCTCCTTTGGCATAATGAGCCTTGGCTTACTTTCCCTCCTGGCAGTCACTTC
1321 TATCCCTTCAGTGAGCAATGCTTTAAACTGGAGAGAATTCAGTTTTATTCAGTCTACACT
1381 TGGATATGTCGCTCTGCTCATAAGTACTTTCCATGTTTTAATTTATGGATGGAAACGAGC
1441 TTTTGAGGAAGAGTACTACAGATTTTATACACCACCAAACTTTGTTCTTGCTCTTGTTTT
1501 GCCCTCAATTGTAATTCTGGATCTTTTGCAGCTTTGCAGATACCCAGACTGAGCTGGAAC
1561 TGGAATTTGTCTTCCTATTGACTCTACTTCTTTAAAAGCGGCTGCCCATTACATTCCTCA
1621 GCTGTCCTTGCAGTTAGGTGTACATGTGACTGAGTGTTGGCCAGTGAGATGAAGTCTCCT
1681 CAAAGGAAGGCAGCATGTGTCCTTTTTCATCCCTTCATCTTGCTGCTGGGATTGTGGATA
1741 TAACAGGAGCCCTGGCAGCTGTCTCCAGAGGATCAAAGCCACACCCAAAGAGTAAGGCAG
1801 ATTAGAGACCAGAAAGACCTTGACTACTTCCCTACTTCCACTGCTTTTTCCTGCATTTAA
1861 GCCATTGTAAATCTGGGTGTGTTACATGAAGTGAAAATTAATTCTTTCTGCCCTTCAGTT
1921 CTTTATCCTGATACCATTTAACACTGTCTGAATTAACTAGACTGCAATAATTCTTTCTTT
1981 TGAAAGCTTTTAAAGGATAATGTGCAATTCACATTAAAATTGATTTTCCATTGTCAATTA
2041 GTTATACTCATTTTCCTGCCTTGATCTTTCATTAGATATTTTGTATCTGCTTGGAATATA
2101 TTATCTTCTTTTTAACTGTGTAATTGGTAATTACTAAAACTCTGTAATCTCCAAAATATT
2161 GCTATCAAATTACACACCATGTTTTCTATCATTCTCATAGATCTGCCTTATAAACATTTA
2221 AATAAAAAGTACTATTTA
```

FIGURE 4G

```
   1 GATCCAGCTTGGGTAGGCGGGGAAGCAGCTGGAGTGCGACCGCCGCGGCAGCCACCCTGCA

62 ACCGCCAGTCGGAGAGAGCTAAGGGCAAGTCCTGAGGTTGGGCCCAGGAGAAAGAAGGCA

122 AGGAGACATTGTCCCAGGTAGGATGTGTCCCAGGATATTCTTGGTGATCTTGGAAGTGTC

M  E  S  I  S  M  M  G  S  P  K  S  L  S  E  T  C  L
 182 CGTATCATGGAATCAATCTCTATGATGGGAAGCCCTAAGAGCCTTAGTGAAACTTGTTTA

19  P  N  G  I  N  G  I  K  D  A  R  K  V  T  V  G  V  I  G  S
 242 CCTAATGGCATAAATGGTATCAAAGATGCAAGGAAGGTCACTGTAGGTGTGATTGGAAGT

39  G  D  F  A  K  S  L  T  I  R  L  I  R  C  G  Y  H  V  V  I
 302 GGAGATTTTGCCAAATCCTTGACCATTCGACTTATTAGATGCGGCTATCATGTGGTCATA

59  G  S  R  N  P  K  F  A  S  E  F  F  P  H  V  V  D  V  T  H
 362 GGAAGTAGAAATCCTAAGTTTGCTTCTGAATTTTTTCCTCATGTGGTAGATGTCACTCAT

79  H  E  D  A  L  T  K  T  N  I  I  F  V  A  I  H  R  E  H  Y
 422 CATGAAGATGCTCTCACAAAAACAAATATAATATTTGTTGCTATACACAGAGAACATTAT

99  T  S  L  W  D  L  R  H  L  L  V  G  K  I  L  I  D  V  S  N
 482 ACCTCCCTGTGGGACCTGAGACATCTGCTTGTGGGTAAAATCCTGATTGATGTGAGCAAT

119  N  M  R  I  N  Q  Y  P  E  S  N  A  E  Y  L  A  S  L  F  P
 542 AACATGAGGATAAACCAGTACCCAGAATCCAATGCTGAATATTTGGCTTCATTATTCCCA

139  D  S  L  I  V  K  G  F  N  V  V  S  A  W  A  L  Q  L  G  P
 602 GATTCTTTGATTGTCAAAGGATTTAATGTTGTCTCAGCTTGGGCACTTCAGTTAGGACCT

159  K  D  A  S  R  Q  V  Y  I  C  S  N  N  I  Q  A  R  Q  Q  V
 662 AAGGATGCCAGCCGGCAGGTTTATATATGCAGCAACAATATTCAAGCGCGACAACAGGTT

179  I  E  L  A  R  Q  L  N  F  I  P  I  D  L  G  S  L  S  S  A
 722 ATTGAACTTGCCCGCCAGTTGAATTTCATTCCCATTGACTTGGGATCCTTATCATCAGCC

199  R  E  I  E  N  L  P  L  R  L  F  T  L  W  R  G  P  V  V  V
 782 AGAGAGATTGAAAATTTACCCCTACGACTCTTTACTCTCTGGAGAGGGCCAGTGGTGGTA

219  A  I  S  L  A  T  F  F  F  L  Y  S  F  V  R  D  V  I  H  P
 842 GCTATAAGCTTGGCCACATTTTTTTTTCCTTTATTCCTTTGTCAGAGATGTGATTCATCCA

239  Y  A  R  N  Q  Q  S  D  F  Y  K  I  P  I  E  I  V  N  K  T
 902 TATGCTAGAAACCAACAGAGTGACTTTTACAAAATTCCTATAGAGATTGTGAATAAAACC

259  L  P  I  V  A  I  T  L  L  S  L  V  Y  L  A  G  L  L  A  A
 962 TTACCTATAGTTGCCATTACTTTGCTCTCCCTAGTATACCTCGCAGGTCTTCTGGCAGCT

279  A  Y  Q  L  Y  Y  G  T  K  Y  R  R  F  P  P  W  L  E  T  W
1022 GCTTATCAACTTTATTACGGCACCAAGTATAGGAGATTTCCACCTTGGTTGGAAACCTGG
```

```
299   L  Q  C  R  K  Q  L  G  L  L  S  F  F  F  A  M  V  H  V  A
1082  TTACAGTGTAGAAAACAGCTTGGATTACTAAGTTTTTTCTTCGCTATGGTCCATGTTGCC

319   Y  S  L  C  L  P  M  R  R  S  E  R  Y  L  F  L  N  M  A  Y
1142  TACAGCCTCTGCTTACCGATGAGAAGGTCAGAGAGATATTTGTTTCTCAACATGGCTTAT

339   Q  Q  V  H  A  N  I  E  N  S  W  N  E  E  E  V  W  R  I  E
1202  CAGCAGGTTCATGCAAATATTGAAAACTCTTGGAATGAGGAAGAAGTTTGGAGAATTGAA

359   M  Y  I  S  F  G  I  M  S  L  G  L  L  S  L  L  A  V  T  S
1262  ATGTATATCTCCTTTGGCATAATGAGCCTTGGCTTACTTTCCCTCCTGGCAGTCACTTCT

379   I  P  S  V  S  N  A  L  N  W  R  E  F  S  F  I  Q  S  T  L
1322  ATCCCTTCAGTGAGCAATGCTTTAAACTGGAGAGAATTCAGTTTTATTCAGTCTACACTT

399   G  Y  V  A  L  L  I  S  T  F  H  V  L  I  Y  G  W  K  R  A
1382  GGATATGTCGCTCTGCTCATAAGTACTTTCCATGTTTTAATTTATGGATGGAAACGAGCT

419   F  E  E  Y  Y  R  F  Y  T  P  P  N  F  V  L  A  L  V  L
1442  TTTGAGGAAGAGTACTACAGATTTTATACACCACCAAACTTTGTTCTTGCTCTTGTTTTG

439   P  S  I  V  I  L  D  L  L  Q  L  C  R  Y  P  D  -
1502  CCCTCAATTGTAATTCTGGATCTTTTGCAGCTTTGCAGATACCCAGACTGAGCTGGAACT
```

FIGURE 4H

EXON_1   75bp
    1   GATCCAGCTTGGGTAGGCGGGGAAGCAGCTGGAGTGCGACCGCCGCGGCAGCCACCCTGC
   61   AACCGCCAGTCGGAG

EXON_2   79bp
    1   AGAGCTAAGGGCAAGTCCTGAGGTTGGGCCCAGGAGAAAGAAGGCAAGGAGACATTGTCC
   61   CAGGTAGGATGTGTCCCAG

EXON_3   525bp
    1   GATATTCTTGGTGATCTTGGAAGTGTCCGTATCATGGAATCAATCTCTATGATGGGAAGC
   61   CCTAAGAGCCTTAGTGAAACTTTTTTACCTAATGGCATAAATGGTATCAAAGATGCAAGG
  121   AAGGTCACTGTAGGTGTGATTGGAAGTGGAGATTTTGCCAAATCCTTGACCATTCGACTT
  181   ATTAGATGCGGCTATCATGTGGTCATAGGAAGTAGAAATCCTAAGTTTGCTTCTGAATTT
  241   TTTCCTCATGTGGTAGATGTCACTCATCATGAAGATGCTCTCACAAAAACAAATATAATA
  301   TTTGTTGCTATACACAGAGAACATTATACCTCCCTGTGGGACCTGAGACATCTGCTTGTG
  361   GGTAAAATCCTGATTGATGTGAGCAATAACATGAGGATAAACCAGTACCCAGAATCCAAT
  421   GCTGAATATTTGGCTTCATTATTCCCAGATTCTTTGATTGTCAAAGGATTTAATGTTGTC
  481   TCAGCTTGGGCACTTCAGTTAGGACCTAAGGATGCCAGCCGGCAG

EXON_4   528bp
    1   GTTTATATATGCAGCAACAATATTCAAGCGCGACAACAGGTTATTGAACTTGCCCGCCAG
   61   TTGAATTTCATTCCCATTGACTTGGGATCCTTATCATCAGCCAGAGAGATTGAAAATTTA
  121   CCCCTACGACTCTTTACTCTCTGGAGAGGGCCAGTGGTGGTAGCTATAAGCTTGGCCACA
  181   TTTTTTTCCTTTATTCCTTTGTCAGAGATGTGATTCATCCATATGCTAGAAACCAACAG
  241   AGTGACTTTTACAAAATTCCTATAGAGATTGTGAATAAAACCTTACCTATAGTTGCCATT
  301   ACTTTGCTCTCCCTAGTATACCTCGCAGGTCTTCTGGCAGCTGCTTATCAACTTTATTAC
  361   GGCACCAAGTATAGGAGATTTCCACCTTGGTTGGAAACCTGGTTACAGTGTAGAAAACAG
  421   CTTGGATTACTAAGTTTTTTCTTCGCTATGGTCCATGTTGCCTACAGCCTCTGCTTACCG
  481   ATGAGAAGGTCAGAGAGATATTTGTTTCTCAACATGGCTTATCAGCAG

EXON_5   165bp
    1   GTTCATGCAAATATTGAAAACTCTTGGAATGAGGAAGAAGTTTGGAGAATTGAAATGTAT
   61   ATCTCCTTTGGCATAATGAGCCTTGGCTTACTTTCCCTCCTGGCAGTCACTTCTATCCCT
  121   TCAGTGAGCAATGCTTTAAACTGGAGAGAATTCAGTTTTATTCAG

EXON_7 and 3'UTR   718bp
    1   ATCTTTTGCAGCTTTGCAGATACCCAGACTGAGCTGGAACTGGAATTTGTCTTCCTATTG
   61   ACTCTACTTCTTTAAAAGCGGCTGCCCATTACATTCCTCAGCTGTCCTTGCAGTTAGGTG
  121   TACATGTGACTGAGTGTTGGCCAGTGAGATGAAGTCTCCTCAAAGGAAGGCAGCATGTGT
  181   CCTTTTTCATCCCTTCATCTTGCTGCTGGGATTGTGGATATAACAGGAGCCCTGGCAGCT
  241   GTCTCCAGAGGATCAAAGCCACACCCAAAGAGTAAGGCAGATTAGAGACCAGAAAGACCT
  301   TGACTACTTCCCTACTTCCACTGCTTTTTCCTGCATTTAAGCCATTGTAAATCTGGGTGT
  361   GTTACATGAAGTGAAAATTAATTCTTTCTGCCCTTCAGTTCTTTATCCTGATACCATTTA
  421   ACACTGTCTGAATTAACTAGACTGCAATAATTCTTTCTTTTGAAAGCTTTTAAAGGATAA
  481   TGTGCAATTCACATTAAAATTGATTTTCCATTGTCAATTAGTTATACTCATTTTCCTGCC
  541   TTGATCTTTCATTAGATATTTTGTATCTGCTTGGAATATATTATCTTCTTTTTAACTGTG
  601   TAATTGGTAATTACTAAAACTCTGTAATCTCCAAAATATTGCTATCAAATTACACACCAT
  661   GTTTTCTATCATTCTCATAGATCTGCCTTATAAACATTTAAATAAAAAGTACTATTTA

FIGURE 4I

```
   1  GGATCCAGCTTGGGTAGGCGGGGAAGCAGCTGGAGTGCGACCGCTACGGCAGCCACCCTG
  61  CAACCGCCAGTCGGAGAGCTAAGGGCAAGTCCTGAGGTTGGGCCCAGGAGAAAGAAGGCA
 121  AGGAGACATTGTCCCAGGATATTCTTGGTGATCTTGGAAGTGTCCGTATCATGGAATCAA
 181  TCTCTATGATGGGAAGCCCTAAGAGCCTTAGTGAAACTTGTTTACCTAATGGCATAAATG
 241  GTATCAAAGATGCAAGGAAGGTCACTGTAGGTGTGATTGGAAGTGGAGATTTTGCCAAAT
 301  CCTTGACCATTCGACTTATTAGATGCGGCTATCATGTGGTCATAGGAAGTAGAAATCCTA
 361  AGTTTGCTTCTGAATTTTTTCCTCATGTGGTAGATGTCACTCATCATGAAGATGCTCTCA
 421  CAAAAACAAATATAATATTTGTTGCTATACACAGAGAACATTATACCTCCCTGTGGGACC
 481  TGAGACATCTGCTTGTGGGTAAAATCCTGATTGATGTGAGCAATAACATGAGGATAAACC
 541  AGTACCCAGAATCCAATGCTGAATATTTGGCTTCATTATTCCCAGATTCTTTGATTGTCA
 601  AAGGATTTAATGTTGTCTCAGCTTGGGCACTTCAGTTAGGACCTAAGGATGCCAGCCGGC
 661  AGGTTTATATATGCAGCAACAATATTCAAGCGCGACAACAGGTTATTGAACTTGCCCGCC
 721  AGTTGAATTTCATTCCCATTGACTTGGGATCCTTATCATCAGCCAGAGGATTGAAAATT
 781  TACCCCTACGACTCTTTACTTTCTGGAGAGGGCCAGTGGTGGTAGCTATAAGCTTGGCCA
 841  CATTTTTTTTCCTTTATTCCTTTGTCAGAGATGTGATTCATCCATATGCTAGAAACCAAC
 901  AGAGTGACTTTTACAAAATTCCTATAGAGATTGTGAATAAAACCTTACCTATAGTTGCCA
 961  TTACTTTGCTCTCCCTAGTATACCTTGCAGGTCTTCTGGCAGCTGCTTATCAACTTTATT
1021  ACGGCACCAAGTATAGGAGATTTCCACCTTGGTTGGAAACCTGGTTACAGTGTAGAAAAC
1081  AGCTTGGATTACTAAGTTTTTTCTTCGCTATGGTCCATGTTGCCTACAGCCTCTGCTTAC
1141  CGATGAGAAGGTCAGAGAGATATTTGTTTCTCAACATGGCTTATCAGCAGGTTCATGCAA
1201  ATATTGAAAACTCTTGGAATGAGGAAGAAGTTTGGAGAATTGAAATGTATATCTCCTTTG
1261  GCATAATGAGCCTTGGCTTACTTTCCCTCCTGGCAGTCACTTCTATCCCTTCGGTGAGCA
1321  ATGCTTTAAACTGGAGAGAATTCAGTTTTATTCAGATCTTTTGCAGCTTTGCAGATACCC
1381  AGACTGAGCTGGAACTGGAATTTGTCTTCCTATTGACTCTACTTCTTTAAAAGCGGCTGC
1441  CCATTACATTCCTCAGCTGTCCTTGCAGTTAGGTGTACATGTGACTGAGTGTTGGCCAGT
1501  GAGATGAAGTCTCCTCAAAGGAAGGCAGCATGTGTCCTTTTTCATCCCTTCATCTTGCTG
1561  CTGGGATTGTGGATATAACAGGAGCCCTGGCAGCTGCTCCAGAGGATCAAAGCCACACCC
1621  AAAGAGTAAGGCAGATTAGAGACCAGAAAGACCTTGACTACTTCCCTACTTCCACTGCTT
1681  TTTCCTGCATTTAAGCCATTGTAAATCTGGGTGTGTTACATGAAGTGAAAATTAATTCTT
1741  TCTGCCCTTCAGTTCTTTATCCTGATACCATTTAACACTGTCTGAATTAACTAGACTGCA
1801  ATAATTCTTTCTTTTGAAAGCTTTTAAAGGATAATGTGCAATTCACATTAAAATTGATTT
1861  TCCATTGTCAATTAGTTATACTCATTTTCCTGCCTTGATCTTTCATTAGATATTTTGTAT
1921  CTGCTTGGAATATATTATCTTCTTTTTAACTGTGTAATTGGTAATTACTAAAACTCTGTA
1981  ATCTCCAAAATATTGCTATCAAATTACACACCATGTTTTCTATCATTCTCATAGATCTGC
2041  CTTATAAACATTTAAATAAAAAGTACTATTTACCAAAAAAAAAAAAAAAAAAAAAAAAAA
2101  AA
```

FIGURE 4J

```
  1 GGATCCAGCTTGGGTAGGCGGGGAAGCAGCTGGAGTGCGACCGCTACGGCAGCCACCCTGCA
 63 ACCGCCAGTCGGAGAGCTAAGGGCAAGTCCTGAGGTTGGGCCCAGGAGAAAGAAGGCAAG

1                                                      M  E  S  I
123 GAGACATTGTCCCAGGATATTCTTGGTGATCTTGGAAGTGTCCGTATCATGGAATCAATC

5   S  M  M  G  S  P  K  S  L  S  E  T  C  L  P  N  G  I  N  G
183 TCTATGATGGGAAGCCCTAAGAGCCTTAGTGAAACTTGTTTACCTAATGGCATAAATGGT

25   I  K  D  A  R  K  V  T  V  G  V  I  G  S  G  D  F  A  K  S
243 ATCAAAGATGCAAGGAAGGTCACTGTAGGTGTGATTGGAAGTGGAGATTTTGCCAAATCC

45   L  T  I  R  L  I  R  C  G  Y  H  V  V  I  G  S  R  N  P  K
303 TTGACCATTCGACTTATTAGATGCGGCTATCATGTGGTCATAGGAAGTAGAAATCCTAAG

65   F  A  S  E  F  F  P  H  V  V  D  V  T  H  H  E  D  A  L  T
363 TTTGCTTCTGAATTTTTTCCTCATGTGGTAGATGTCACTCATCATGAAGATGCTCTCACA

85   K  T  N  I  I  F  V  A  I  H  R  E  H  Y  T  S  L  W  D  L
423 AAAACAAATATAATATTTGTTGCTATACACAGAGAACATTATACCTCCCTGTGGGACCTG

105   R  H  L  L  V  G  K  I  L  I  D  V  S  N  N  M  R  I  N  Q
483 AGACATCTGCTTGTGGGTAAAATCCTGATTGATGTGAGCAATAACATGAGGATAAACCAG

125   Y  P  E  S  N  A  E  Y  L  A  S  L  F  P  D  S  L  I  V  K
543 TACCCAGAATCCAATGCTGAATATTTGGCTTCATTATTCCCAGATTCTTTGATTGTCAAA

145   G  F  N  V  V  S  A  W  A  L  Q  L  G  P  K  D  A  S  R  Q
603 GGATTTAATGTTGTCTCAGCTTGGGCACTTCAGTTAGGACCTAAGGATGCCAGCCGGCAG

165   V  Y  I  C  S  N  N  I  Q  A  R  Q  Q  V  I  E  L  A  R  Q
663 GTTTATATATGCAGCAACAATATTCAAGCGCGACAACAGGTTATTGAACTTGCCCGCCAG

185   L  N  F  I  P  I  D  L  G  S  L  S  S  A  R  E  I  E  N  L
723 TTGAATTTCATTCCCATTGACTTGGGATCCTTATCATCAGCCAGAGAGATTGAAAATTTA

205   P  L  R  L  F  T  F  W  R  G  P  V  V  V  A  I  S  L  A  T
783 CCCCTACGACTCTTTACTTTCTGGAGAGGGCCAGTGGTGGTAGCTATAAGCTTGGCCACA

225   F  F  F  L  Y  S  F  V  R  D  V  I  H  P  Y  A  R  N  Q  Q
843 TTTTTTTTCCTTTATTCCTTTGTCAGAGATGTGATTCATCCATATGCTAGAAACCAACAG

245   S  D  F  Y  K  I  P  I  E  I  V  N  K  T  L  P  I  V  A  I
903 AGTGACTTTTACAAAATTCCTATAGAGATTGTGAATAAAACCTTACCTATAGTTGCCATT

265   T  L  L  S  L  V  Y  L  A  G  L  L  A  A  A  Y  Q  L  Y  Y
963 ACTTTGCTCTCCCTAGTATACCTTGCAGGTCTTCTGGCAGCTGCTTATCAACTTTATTAC

285   G  T  K  Y  R  R  F  P  P  W  L  E  T  W  L  Q  C  R  K  Q
1023 GGCACCAAGTATAGGAGATTTCCACCTTGGTTGGAAACCTGGTTACAGTGTAGAAAACAG

305   L  G  L  L  S  F  F  F  A  M  V  H  V  A  Y  S  L  C  L  P
1083 CTTGGATTACTAAGTTTTTTCTTCGCTATGGTCCATGTTGCCTACAGCCTCTGCTTACCG

```
1143 ATGAGAAGGTCAGAGAGATATTTGTTTCTCAACATGGCTTATCAGCAGGTTCATGCAAAT

345      I  E  N  S  W  N  E  E  E  V  W  R  I  E  M  Y  I  S  F  G
1203 ATTGAAAACTCTTGGAATGAGGAAGAAGTTTGGAGAATTGAAATGTATATCTCCTTTGGC

365      I  M  S  L  G  L  L  S  L  L  A  V  T  S  I  P  S  V  S  N
1263 ATAATGAGCCTTGGCTTACTTTCCCTCCTGGCAGTCACTTCTATCCCTTCGGTGAGCAAT

385      A  L  N  W  R  E  F  S  F  I  Q  I  F  C  S  F  A  D  T  Q
1323 GCTTTAAACTGGAGAGAATTCAGTTTTATTCAGATCTTTTGCAGCTTTGCAGATACCCAG

405      T  E  L  E  L  E  F  V  F  L  L  T  L  L  L  *
1383 ACTGAGCTGGAACTGGAATTTGTCTTCCTATTGACTCTACTTCTTTAAAAGCGGCTGCCC
1443 ATTACATTCCTCAGCTGTCCTTGCAGTTAGGTGTACATGTGACTGAGTGTTGGCCAGTGA
1503 GATGAAGTCTCCTCAAAGGAAGGCAGCATGTGTCCTTTTTCATCCCTTCATCTTGCTGCT
1563 GGGATTGTGGATATAACAGGAGCCCTGGCAGCTGCTCCAGAGGATCAAAGCCACACCCAA
1623 AGAGTAAGGCAGATTAGAGACCAGAAAGACCTTGACTACTTCCCTACTTCCACTGCTTTT
1683 TCCTGCATTTAAGCCATTGTAAATCTGGGTGTGTTACATGAAGTGAAAATTAATTCTTTC
1743 TGCCCTTCAGTTCTTTATCCTGATACCATTTAACACTGTCTGAATTAACTAGACTGCAAT
1803 AATTCTTTCTTTTGAAAGCTTTTAAAGGATAATGTGCAATTCACATTAAAATTGATTTTC
1863 CATTGTCAATTAGTTATACTCATTTTCCTGCCTTGATCTTTCATTAGATATTTTGTATCT
1923 GCTTGGAATATATTATCTTCTTTTTAACTGTGTAATTGGTAATTACTAAAACTCTGTAAT
1983 CTCCAAAATATTGCTATCAAATTACACACCATGTTTTCTATCATTCTCATAGATCTGCCT
2043 TATAAACATTTAAATAAAAAGTACTATTTACCAAAAAAAAAAAAAAAAAAAAAAAAAAAA
```

FIGURE 4K

```
  1        M   E   K   T   C   I   D   A   L   P   L   T   M   N   S   S   E   K
  1 ACAGATCTATGGAGAAAACTTGTATAGATGCACTTCCTCTTACTATGAATTCTTCAGAAAAG

19    Q   E   T   V   C   I   F   G   T   G   D   F   G   R   S   L   G   L   K   M
 63 CAAGAGACTGTATGTATTTTTGGAACTGGTGATTTTGGAAGATCACTGGGATTGAAAATG

39    L   Q   C   G   Y   S   V   V   F   G   S   R   N   P   Q   K   T   T   L   L
123 CTCCAGTGTGGTTATTCTGTTGTTTTTGGAAGTCGAAACCCCCAGAAGACCACCCTACTG

59    P   S   G   A   E   V   L   S   Y   S   E   A   A   K   K   S   D   I   I   I
183 CCCAGTGGTGCAGAAGTCTTGAGCTATTCAGAAGCAGCCAAGAAGTCTGACATCATAATC

79    I   A   I   H   R   E   H   Y   D   F   L   T   E   L   T   E   V   L   N   G
243 ATAGCAATCCACAGAGAGCATTATGATTTTCTCACAGAATTAACTGAGGTTCTCAATGGA

99    K   I   L   V   D   I   S   N   N   L   K   I   N   Q   Y   P   E   S   N   A
303 AAAATATTGGTAGACATCAGCAACAACCTCAAAATCAATCAATATCCAGAATCTAATGCA

119    E   Y   L   A/T H   L   V   P   G   A   H   V   V   K   A   F   N   T   I   S
363 GAGTACCTTGCTCATTTGGTGCCAGGAGCCCACGTGGTAAAAGCATTTAACACCATCTCA

139    A   W   A   L   Q   S   G   A   L   D   A   S   R   Q   V   F   V   C   G   N
423 GCCTGGGCTCTCCAGTCAGGAGCACTGGATGCAAGTCGGCAGGTGTTTGTGTGTGGAAAT

159    D   S   K   A   K   Q   R   V   M   D   I   V   R   N   L   G   L   T   P   M
483 GACAGCAAAGCCAAGCAAAGAGTGATGGATATTGTTCGTAATCTTGGACTTACTCCAATG

179    D   Q   G   S   L   M   A   A   K   E   I   E   K   Y   P   L   Q   L   F   P
543 GATCAAGGATCACTCATGGCAGCCAAAGAAATTGAAAAGTACCCCCTGCAGCTATTTCCA

199    M   W   R   F   P   F   Y   L   S   A   V   L   C   V   F   L   F   F   Y   C
603 ATGTGGAGGTTCCCCTTCTATTTGTCTGCTGTGCTGTGTGTCTTCTTGTTTTTCTATTGT

219    V   I   R   D   V   I   Y   P   Y   V   Y   E   K   K   D   N   T   F   R   M
663 GTTATAAGAGACGTAATCTACCCTTATGTTTATGAAAAGAAAGATAATACATTTCGTATG

239    A   I   S   I   P   N   R   I   F   P   I   T   A   L   T   L   L   A   L   V
723 GCTATTTCCATTCCAAATCGTATCTTTCCAATAACAGCACTTACACTGCTTGCTTTGGTT

259    Y   L   P   G   V   I   A   A   I   L   Q   L   Y   R   G   T   K   Y   R   R
783 TACCTCCCTGGTGTTATTGCTGCCATTCTACAACTGTACCGAGGCACAAAATACCGTCGA

279    F   P   D   W   L   D   H   W   M   L   C   R   K   Q   L   G   L   V   A   L
843 TTCCCAGACTGGCTTGACCACTGGATGCTTTGCCGAAAGCAGCTTGGCTTGGTAGCTCTG

299    G   F   A   F   L   H   V   L   Y   T   L   V   I   P   I   R   Y   Y   V   R
903 GGATTTGCCTTCCTTCATGTCCTCTACACACTTGTGATTCCTATTCGATATTATGTACGA

319    W   R   L   G   N   L   T   V   T   Q   A   I P/L K   K   E   N   P   F   S
963 TGGAGATTGGGAAACTTAACCGTTACCCAGGCAATACCCAAGAAGGAGAATCCATTTAGC

339    T   S   S   A   W   L   S   D   S   Y   V   A   L   G   I   L   G   F   F   L
1023 ACCTCCTCAGCCTGGCTCAGTGATTCATATGTGGCTTTGGGAATACTTGGGTTTTTTCTG

```
1083  TTTGTACTCTTGGGAATCACTTCTTTGCCATCTGTTAGCAATGCAGTCAACTGGAGAGAG

379    F   R   F   V   Q   S   K   L   G   Y   L   T   L   I   L   C   T   A   H   T
1143  TTCCGATTTGTCCAGTCCAAACTGGGTTATTTGACCCTGATCTTGTGTACAGCCCACACC

399    L   V   Y   G   G   K   R   F   L   S   P   S   N   L   R   W   Y   L   P   A
1203  CTGGTGTACGGTGGAAGAGATTCCTCAGCCCTTCAAATCTCAGATGGTATCTTCCTGCA

429    A   Y   V   L   G   L   I   I   P   C   T   V   L   V   I   K   F   V   L   I
1263  GCCTACGTGTTAGGGCTTATCATTCCTTGCACTGTGCTGGTGATCAAGTTTGTCCTAATC

439    M   P   C   V   D   N   T   L   T   R   I   R   Q   G   W   E   R   N   S   K
1323  ATGCCATGTGTAGACAACACCCTTACAAGGATCCGCCAGGGCTGGGAAAGGAACTCAAAA

459    H
1383  CACTAGCTCGAGGT
```

FIGURE 4L

```
  1   ACCCTTCGCCGCGGACCTTCAGCTGCCGCGGTCGCTCCGAGCGGCGGGCCGCAGAGGTTC
 61   AAGCGATTCTCCTGCTTCAGCCTCCGGAGTAGCTGGGATTACAGGCACGTGCCAACACAC

1                 M  P  E  E  M  D  K  P  L  I  S  L  H  L  V  D
121   CCAGCCACCAAAATGCCAGAAGAGATGGACAAGCCACTGATCAGCCTCCACCTGGTGGAC

17    S  D  S  S  L  A  K  V  P  D  E  A  P  K  V  G  I  L  G  S
181   AGCGATAGTAGCCTTGCCAAGGTCCCCGATGAGGCCCCCAAAGTGGGCATCCTGGGTAGC

37    G  D  F  A  R  S  L  A  T  R  L  V  G  S  G  F  K  V  V  V
241   GGGGACTTTGCCCGCTCCCTGGCCACACGCCTGGTGGGCTCTGGCTTCAAAGTGGTGGTG

57    G  S  R  N  P  K  R  T  A  R  L  Y  P  S  A  A  Q  V  T  F
301   GGGAGCCGCAACCCCAAACGCACAGCCAGGCTGTATCCCTCAGCGGCCCAAGTGACTTTC

77    Q  E  E  A  V  S  S  P  E  V  I  F  V  A  V  F  R  E  H  Y
361   CAAGAGGAGGCAGTGAGCTCCCCGGAGGTCATCTTTGTGGCTGTGTTCCGGGAGCACTAC

97    S  S  L  C  S  L  S  D  Q  L  A  G  K  I  L  V  D  V  S  N
421   TCTTCACTGTGCAGTCTCAGTGACCAGCTGGCGGGCAAGATCCTGGTGGATGTGAGCAAC

117    P  T  E  Q  H  L  Q  H  R  E  S  N  A  E  Y  L  A  S  L
481   CCTACAGAGCAAGAGCACCTTCAGCATCGTGAGTCCAATGCTGAGTACCTGGCCTCCCTC

137    F  P  T  C  T  V  V  K  A  F  N  V  I  S  A  W  T  L  Q  A
541   TTCCCCACTTGCACAGTGGTCAAGGCCTTCAATGTCATCTCTGCCTGGACCCTGCAGGCT

157    G  P  R  D  G  N  R  Q  V  P  I  C  G  D  Q  P  E  A  K  R
601   GGCCCAAGGGATGGTAACAGGCAGGTGCCCATCTGCGGTGACCAGCCAGAAGCCAAGCGT

177    A  V  S  E  M  A  L  A  M  G  F  M  P  V  D  M  G  S  L  A
661   GCTGTCTCGGAGATGGCGCTCGCCATGGGCTTCATGCCCGTGGACATGGGATCCCTGGCG

197    S  A  W  E  V  E  A  M  P  L  R  L  L  P  A  W  K  V  P  T
721   TCAGCCTGGGAGGTGGAGGCCATGCCCCTGCGCCTCCTCCCGGCCTGGAAGGTGCCCACC

217    L  L  A  L  G  L  F  V  C  F  Y  A  Y  N  F  V  R  D  V  L
781   CTGCTGGCCCTGGGGCTCTTCGTCTGCTTCTATGCCTACAACTTCGTCCGGGACGTTCTG

237    Q  P  Y  V  Q  E  S  Q  N  K  F  F  K  L  P  V  S  V  V  N
841   CAGCCCTATGTGCAGGAAAGCCAGAACAAGTTCTTCAAGCTGCCCGTGTCCGTGGTCAAC

257    T  T  L  P  C  V  A  Y  V  L  L  S  L  V  Y  L  P  G  V  L
901   ACCACACTGCCGTGCGTGGCCTACGTGCTGCTGTCACTCGTGTACTTGCCCGGCGTGCTG

277    A  A  A  L  Q  L  R  R  G  T  K  Y  Q  R  F  P  D  W  L  D
961   GCGGCTGCCCTGCAGCTGCGGCGCGGCACCAAGTACCAGCGCTTCCCCGACTGGCTGGAC

297    H  W  L  Q  H  R  K  Q  I  G  L  L  S  F  F  C  A  A  L  H
1021  CACTGGCTACAGCACCGCAAGCAGATCGGGCTGCTCAGCTTCTTCTGCGCCGCCCTGCAC

317    A  L  Y  S  F  C  L  P  L  R  R  A  H  R  Y  D  L  V  N  L
1081  GCCCTCTACAGCTTCTGCTTGCCGCTGCGCCGCGCCCACCGCTACGACCTGGTCAACCTG

337    A  V  K  Q  V  L  A  N  K  S  H  L  W  V  E  E  E  V  W  R
1141  GCAGTCAAGCAGGTCTTGGCCAACAAGAGCCACCTCTGGGTGGAGGAGGAGGTCTGGCGG

357    M  E  I  Y  L  S  L  G  V  L  A  L  G  T  L  S  L  L  A  V
1201  ATGGAGATCTACCTCTCCCTGGGAGTGCTGGCCCTCGGCACGTTGTCCCTGCTGGCCGTG
```

```
377  T  S  L  P  S  I  A  N  S  L  N  W  R  E  F  S  F  V  Q  S
1261 ACCTCACTGCCGTCCATTGCAAACTCGCTCAACTGGAGGGAGTTCAGCTTCGTTCAGTCC

397  S  L  G  F  V  A  L  V  L  S  T  L  H  T  L  T  Y  G  W  T
1321 TCACTGGGCTTTGTGGCCCTCGTGCTGAGCACACTGCACACGCTCACCTACGGCTGGACC

417  R  A  F  E  S  R  Y  K  F  Y  L  P  P  T  F  T  L  T  L
1381 CGCGCCTTCGAGGAGAGCCGCTACAAGTTCTACCTGCCTCCCACCTTCACGCTCACGCTG

437  L  V  P  C  V  V  I  L  A  K  A  L  F  L  L  P  C  I  S  R
1441 CTGGTGCCCTGCGTCGTCATCCTGGCCAAAGCCCTGTTTCTCCTGCCCTGCATCAGCCGC

457  R  L  A  R  I  R  R  G  W  E  R  E  S  T  I  K  F  T  L  P
1501 AGACTCGCCAGGATCCGGAGAGGCTGGGAGAGGGAGAGCACCATCAAGTTCACGCTGCCC

477  T  D  H  A  L  A  E  K  T  S  H  V  -
1561 ACAGACCACGCCCTGGCCGAGAAGACGAGCCACGTATGAGGTGCCTGCCCTGGGCTCTGG

1621 ACCCCGGGCACACGAGGGACGGTGCCCTGAGCCCGTTAGGTTTTCTTTTCTTGGTGGTGC
1681 AAAGTGGTATAACTGTGTGCAAATAGGAGGTTTGAGGTCCAAATTCCTGGGACTCAAATG
1741 TATGCAGTACTATTCAGAATGATATACACACATATGTGTATATGTATTTACATATATTCC
1801 ACATATATAACAGGATTTGCAATTATACATAGCTAGCTAAAAAGTTGGGTCTCTGAGATT
1861 TCAACTTGTAGATTTAAAAACAAGTGCCGTACGTTAAGAGAAGAGCAGATCATGCTATTG
1921 TGACATTTGCAGAGATATACACACACTTTTTGTACAGAAGAGGCTTGTGCTGTGGTGGGT
1981 TCGATTTATCCCTGCCCACCCCATCCCCACAACTTCCCTTTTGCTACTTCCCCAAGGCTC
2041 TTGCAGAGCTAGGGCTCTGAAGGGGAGGGAAGGCAACGGCTCTGCCCAGAGCCATCCCTG
2101 GAGCATGTGAGCAGCGGCTGGTCTCTTCCCTCCACCTGGGGCAGCAGCAGGAGGCCTGGG
2161 GGGGAGGAAAATCAGGCAGTCGGCCTGGAGTCTGTGCCTGGTCCTTTGCCCGGTGGTGGG
2221 AGGATGGAGGGATTGGGCTGAAGCTGCTCCACCTCATCCTTGCTGAGTGGGGAGACATT
2281 TTCCCTGAAAGTCAGAAGTCACCATAGAGCCTGCAAATGGATCCTCCTGTGAGAGTGACG
2341 TCACCTCCTTTCCAGAGCCATTAGTGAGCCTGGCTTGGGAACAAGTGTAATTTCCTTCCC
2401 TCCTTTAACCTGGCGATGAGCGTCCTTTAAACCACTGTGCCTTCTCACCCTTTCCATCTT
2461 CAGTTTGAACGACTCCCAGGAAGGCCTAGAGCAGACCCTTTAGAAATCAGCCCAAGGGGG
2521 AGAGCAAGAGAAAACACTCTAGGGAGTAAAGCTCCCCGGGCGTCAGAGTTGAGCCCTGCC
2581 TGGGCTGAAGGACTGTCTTCACGAAGTCAGTCCTGAGGAAAAATATTGGGGACTCCAAAT
2641 GTCCTCTGGCAGAGGACCCAGAAAACCACACTGGCTCCAACTTCCTCCTCATGGGGCATT
2701 ACACTTCAAAACAGTGGGGAGCAACTTTTCCACCAAAGCTACAAACCTAAAATGCTGCTG
2761 CCCCAAAGCACAAGAGGGAAGAGCACCGCCGGGGCCACAGGACGTCTGTCCTCCAGTCAC
2821 AGGCCATCCTTGCTGCTCCCTACTGACTCTAGCTTACTTCCCCTGTGAAGAAACAGGTGT
2881 TCTCGGCTGAGCCCCCAACCCTCTGCAGAACCAGGTTGATCTGCCACAGAAAAAGCATCT
2941 TTGAAGACAAAGAGGGTGAGGTCTTCATGAGTCTCCTGGGCCCAAAGCCATCTTCTGATG
3001 GAAGGAAGAGAGTAGGGCCAGTGAAGGCTGCCCAGAGAGAATGTCACAGATGAGGCTGCC
3061 CCTGCCCCCTCCCCGCCAGGGAGGTTTCATGAGCTCATGTCTATGCAGCACATAAGGGTT
3121 CTTCAGTGAAAAGCAGGAGAAGAGCCCACTGCAAGGATAGCTCATTAGGCACATGACCGA
3181 TGCAGGGAAGGCCATGCCGGGGAAGCTCTTCCTGCAGGTATTTTCCATCTGCTGTGCCAA
3241 GGCTGAGCGGCAGAAACTTGTCTCATAAATTGGCACTGATGGAGCATCAGCTGTGGCCCA
3301 CAGAGAGCCTTGCTGAGAAGGGGGCAGGTAAAGCAGAGATTTTAGCATTGCCTTGGCATA
3361 ACAAGGGCCCATCGATTCCCTACTAATGAGAGGCAGGGAGAGCATGGGCAATGGAGACCC
3421 ACCAATGATCCCCAACCCCGGTGGGTACTGGCTGCCTGCCCTGGGCCAGGGAATGGCTCC
3481 TTATACCAAAGATGCTGGCACATAGCAGAACCCAGTGCACGTCCTCCCCTTCCCACCCAC
3541 CTCTGGCTGAAGGTGCTCAAGAGGGAAGCAATTATAAGGTGGGTGGCAGGAGGGAACAGG
3601 TGCCACCTGCTGGACAATCACACGAAAGGCAGGCGGGCTGTGTACTGGGCCCTGACTGTG
3661 CGTCCACTGCTGTCTTCCCTACCTCACCAGGCTACTGGCAGCAGCATCCCGAGAGCACAT
3721 CATCTCCACAGCCTGGTAAATTCCATGTGCCTCTGGGTACAAAAGTGCCTCAACGACATG
3781 CTCTGGAAATCCCAAATGCCACAGTCTGAGGTTGATATCTAAAATCTATGCCTTCAAAAG
3841 AGTCTCTGTTTTTTTTTTTAACCTGGTAGACGGTATAAAAGCAGTGCAAATAAACACCT
3901 AACCTTCTGC
```

```
   1 AGCGGCGGCTCCTGCAGCGGTGGTCGGCTGTTGGGTGTGGAGTTTCCCAGCGCCCCTCGGG
   1                                                           M  T
  62 TCCGACCCTTTGAGCGTTCTGCTCCGGCGCCAGCCTACCTCGCTCCTCGGCGCCATGACC

3  T  T  T  T  F  K  G  V  D  P  N  S  R  N  S  S  R  V  L  R
 122 ACAACCACCACCTTCAAGGGAGTCGACCCCAACAGCAGGAATAGCTCCCGAGTTTTGCGG

23  P  P  G  G  S  N  F  S  L  G  F  D  E  P  T  E  Q  P  V
 182 CCTCCAGGTGGTGGATCCAATTTTTCATTAGGTTTTGATGAACCAACAGAACAACCTGTG

43  R  K  N  K  M  A  S  N  I  F  G  T  P  E  E  N  Q  A  S  W
 242 AGGAAGAACAAAATGGCCTCTAATATCTTTGGGACACCTGAAGAAAATCAAGCTTCTTGG

63  A  K  S  A  G  A  K  S  S  G  G  R  E  D  L  E  S  S  G  L
 302 GCCAAGTCAGCAGGTGCCAAGTCTAGTGGTGGCAGGGAAGACTTGGAGTCATCTGGACTG

83  Q  R  R  N  S  S  E  A  S  S  G  D  F  L  D  L  K  G  E  G
 362 CAGAGAAGGAACTCCTCTGAAGCAAGCTCCGGAGACTTCTTAGATCTGAAGGGAGAAGGT

103  D  I  H  E  N  V  D  T  D  L  P  G  S  L  G  Q  S  E  K
 422 GATATTCATGAAAATGTGGACACAGACTTGCCAGGCAGCCTGGGGCAGAGTGAAGAGAAG

123  P  V  P  A  A  P  V  P  S  P  V  A  P  A  P  V  P  S  R  R
 482 CCCGTGCCTGCTGCGCCTGTGCCCAGCCCGGTGGCCCCGGCCCCAGTGCCATCCAGAAGA

143  N  P  P  G  G  K  S  S  L  V  L  G  *
 542 AATCCCCCTGGCGGCAAGTCCAGCCTCGTCTTGGGTTAGCTCTGACTGTCCTGAACGCTG

602 TCGTTCTGTCTGTTTCCTCCATGCTTGTGAACTGCACAACTTGAGCCTGACTGTACATCT
 662 CTTGGATTTGTTTCATTAAAAAGAAGCACTTTATGTACTGCTGTCTTTTTTTTTTTCTT
 722 TTGAAGAACAGGTTTCTCTCTGTCCTTGACTCTTGGGTCTGTGGGCCATGGCATGAGTGT
 782 TTTCTAGTAGTAGATTGGAGGGAAAGCTTTGTGACACTTAGTACTGTGTTTTTAAGAAGA
 842 AATAATTTGGTTCCAGATGTGTTAGAGGATCTTTTGTACTGAGGTTTTTAACACTTTACT
 902 TGGGTTTACCAAGCCTCAACTGGACAGACCATAAACAGTCCACAGGCACCGTTCCTGCCA
 962 GGCCCCAACCCACAGGGAGTCTCTCCGCAGAGCCTTCTTGGTGTTGCCCTAACTTGCCAG
1022 TGGCCTTTGCTCAGAGCCTCCTCCTGTGACATGTGAACAATGAAGAGGCCTGCGCCTCCT
1082 GCCTTGCCGCCTGCAAAGCAAAGAAACTGCCTTTTATTTTTTAACCCTTAAAAAGTAGCCA
1142 GATAGTAACAAGACTGGCTGGCTGATGAGCAAAGCCTTTGCTCTCACGCAGAGGAAGGCT
1202 TGGATGTACAATGAAACTGCCTGGAACTAAAAGCAGTGAAGCAAGGGAGGCAATCACACT
1262 GAAGCGGGTCTTCCTCCAGGAACGGGGTCCCACAGGCGTGTTGTTTTAAATAACCTGATG
1322 CTGTGTGCATGATGCTGGTGCTTGACCATGAAAGGAAAGTCTCATCCTTAAAAATGTGTT
1382 TACTTCACAATCCTGGACTGTTGCTTCAAGTAAACAATATCCACATTCTAAAAAAAAAAA
1442 AAAAAAAAAAAAAAAAAAAAA
```

Predicted promoter tgaaaaccc[tataa]aggogtcgatcggccggacaggcgg[a]gcggcggct

SSH9 EXON-Intron boundaries;

EXON1  CATGACCACAACCaccaccttcaaggga...  INT1 ...tgccattatttgcagAGTTTTGCGGCCT
EXON2  AAATCAAGCTTCTtgggccaagtcagca...  INT2 ...tattttgattttagGTGCCAAGTCTAG
EXON3  CTTAGATCTGAAGgtcagtgtgacagca...  INT4 ...tttttctttctagGGAGAAG
EXON4  GTGATATTCATGgtaagtacttctgaa...  INT5 ...tccctgttttcatagAAAATGTGGACAC

FIGURE 11C

```
   1 ATGACCGACGCGCTGTTGCCCGCGGCCCCCCAGCCGCTGGAGAAGGAGAACGACGGCTAC
  61 TTTCGGAAGGGCTGTAATCCCCTTGCACAAACCGGCCGGAGTAAATTGCAGAATCAAAGA
 121 GCTGCTTTGAATCAGCAGATCCTGAAAGCCGTGCGGATGAGGACCGGAGCGGAAAACCTT
 181 CTGAAAGTGGCCACAAACTCAAAGGTGCGGGAGCAAGTGCGGCTGGAGCTGAGCTTCGTC
 241 AACTCAGACCTGCAGATGCTCAAGGAAGAGCTGGAGGGGCTGAACATCTCGGTGGGCGTC
 301 TATCAGAACACAGAGGAGGCATTTACGATTCCCCTGATTCCTCTTGGCCTGAAGGAAACG
 361 AAAGACGTCGACTTTGCAGTCGTCCTCAAGGATTTTATCCTGGAACATTACAGTGAAGAT
 421 GGCTATTTATATGAAGATGAAATTGCAGATCTTATGGATCTGAGACAAGCTTGTCGGACG
 481 CCTAGCCGGGATGAGGCCGGGGTGGAACTGCTGATGACATACTTCATCCAGCTGGGCTTT
 541 GTCGAGAGTCGATTCTTCCCGCCCACACGGCAGATGGGACTCCTGTTCACCTGGTATGAC
 601 TCTCTCACTGGGGTTCCGGTCAGCCAGCAGAACCTGCTGCTGGAGAAGGCCAGTGTCCTG
 661 TTCAACACTGGGGCCCTCTACACCCAGATTGGGACCCGGTGCGATCGGCAGACGCAGGCT
 721 GGGCTGGAGAGTGCCATAGATGCCTTTCAGAGAGCCGCAGGGGTTTTAAATTACCTGAAA
 781 GACACATTTACCCATACTCCAAGTTACGACATGAGCCCTGCCATGCTCAGCGTGCTCGTC
 841 AAAATGATGCTTGCACAAGCCCAAGAAAGCGTGTTTGAGAAAATCAGCCTTCCTGGGATC
 901 CGGAATGAATTCTTCATGCTGGTGAAGGTGGCTCAGGAGGCTGCTAAGGTGGGAGAGGTC
 961 TACCAACAGCTACACGCAGCCATGAGCCAGGCGCCGGTGAAAGAGAACATCCCCTACTCC
1021 TGGGCCAGCTTAGCCTGCGTGAAGGCCCACCACTACGCGGCCCTGGCCCACTACTTCACT
1081 GCCATCCTCCTCATCGACCACCAGGTGAAGCCAGGCACGGATCTGGACCACCAGGAGAAG
1141 TGCCTGTCCCAGCTCTACGACCACATGCCAGAGGGGCTGACACCCTTGGCCACACTGAAG
1201 AATGATCAGCAGCGCCGACAGCTGGGGAAGTCCCACTTGCGCAGAGCCATGGCTCATCAC
1261 GAGGAGTCGGTGCGGGAGGCGAGCCTCTGCAAGAAGCTGCGGAGCATTGAGGTGCTACAG
1321 AAGGTGCTGTGTGCCGCACAGGAACGCTCCCGGCTCACGTACGCCCAGCACCAGGAGGAG
1381 GATGACCTGCTGAACCTGATCGACGCCCCAGTGTTGTTGCTAAAACTGAGCAAGAGGTT
1441 GACATTATATTGCCCCAGTTCTCCAAGCTGACAGTCACGGACTTCTTCCAGAAGCTGGGC
1501 CCCTTATCTGTGTTTTCGGCTAACAAGCGGTGGACGCCTCCTCGAAGCATCCGCTTCACT
1561 GCAGAAGAAGGGGACTTGGGGTTCACCTTGAGAGGGAACGCCCCCGTTCAGGTTCACTTC
1621 CTGGATCCTTACTGCTCTGCCTCGGTGGCAGGAGCCCGGGAAGGAGATTATATTGTCTCC
1681 ATTCGCTTGTGATTGTAAGTGGCTGACGCTGAGTGAGGTTATGAAGCTGCTGAAGAGC
1741 TTTGGCGAGGACGAGATCGAGATGAAAGTCGTGAGCCTCCTGGACTCCACATCATCCATG
1801 CATAATAAGAGTGCCACATACTCCGTGGGAATGCAGAAAACGTACTCCATGATCTGCTTA
1861 GCCATTGATGATGACGACAAAACTGATAAAACCAAGAAAATCTCCAAGAAGCTTTCCTTC
1921 CTGAGTTGGGGCACCAACAAGAACAGACAGAAGTCAGCCAGCACCTTGTGCCTCCCATCG
1981 GTCGGGGCTGCACGGCCTCAGGTCAAGAAGAAGCTGCCCTCCCCTTTCAGCCTTCTCAAC
2041 TCAGACAGTTCTTGGTACTAATGTGAGGAAACAAACATGTTCAGGCCCCGAACATTTCCG
2101 GTGCTGACTCGGCCTTAAACGTTTGTGCCATAATGGAAAATATCTATCTATCTGTTCTCA
2161 AATCCTGTTTTTCTCATAGTGTAAACTCACATTTGATGTGTTTTTATGAAGGAAAGTAAC
2221 CAAGAAACCTCTAGGAATTAGTGAAAAAAGAACTTTTTTGAGGTGTGTTACTATACTGCT
2281 GTAAGTTATTTATTATATAAAGTATTGTAAATAGAATAGTGTTGAAGATATGAAATATGG
2341 CTATTTTTAATGGTGACAATTATGACTTTTAGTCACTATTAAATTGGGGTTACCTATATC
2401 AGTACAATTTGTAGTTGTTTCCAGGTTTGGCTAATAATCATTCCTTAACCTAGAATTCAG
2461 ATGATCCTGGAATTAAGGCAGGTCAGAGGACTGTAATGATAGAATTAAATTAGTGTCACT
2521 AAAAACTGTCCCAAAGTGCTGCTTCCTAATAGGAATTCATTAACCTAAAACAAGATGTTA
2581 CTATTATATCGATAGACTATGAATGCTATTTCTAGAAAAAAGTCTAGTGCCAAATTTGTCT
2641 TATTAAATAAAAACAATGTAGGAGCAGCTTTTCTTCTAGTTTGATGTCATTTAAGAATTA
2701 CTAACACAGTGGCAGTGTTAGATGAAGATGCTGTCTACAAGGTAGATAATATACTGTTTG
2761 ATACTCAAAACATTTTTCATTTTGTTTAAAGTAGAAGTTACATAATTCTATATTTTAAGT
2821 CTTGGGTAAAAAAGTAGTTTTACATTTTATAAAGTAAAGATGTAAATGATTCAGGTTTAA
2881 AGCTCTATTTGACTTCCTTTTTTTGTTTGAGATAGCGTCTTGCTGTGTTGCCCAGGCTGG
2941 AGTGCAGTGGTGTGATCTCAGCTCAGTGCAACCTCCGCCCCTGGGATCAAGCGATTCTC
3001 CTACCTCAGCCTCCCAAATAGCTGGGACTACAAGGTGCCCTCCAGCATGCCTGGCTGATT
3061 TTTGTATTTTTAGTTGAGGTGAGGTTTCACCATGTTGGCCAGGCGGGTTTCGAAATCCTG
3121 ACCTCAAATGATCCACCCACCTCAGCCTCCCAAAGTGCTGGGATTACAGGCATGAGCCAC
3181 CACAACCGTCCCACTATTTACTTTTTAAAATGACATTCCTACTGATTGATTTTTATCTT
3241 GCTATAAGTTCGATGACACCGTGAATCTAATAAGGTTCACTGTTGACACAGTACAAGTTA
3301 CATAGCTAAAATACATAGCATTGAAGACTAATTTTAAGGATTGACAAGAGTTTATTTTCT
3361 ATTGTGCAATATCTTAAAGGAAGCAACCACCTTTGGGAAAGTGTATCTGCTGCTCCTAGG
3421 GCCATGCTTGTATACATATTTAAATAAACATATTCATTTACCCGAAAAAAAAAAAAAAAA
3481 AAAAAAAAAAAAAAAAAAAAAAAAAAAAAAAAAAAAAAAAAAAA
```

FIGURE 14A

```
  1  M  T  D  A  L  L  P  A  A  P  Q  P  L  E  K  E  N  D  G  Y
  1  ATGACCGACGCGCTGTTGCCCGCGGCCCCCCAGCCGCTGGAGAAGGAGAACGACGGCTAC

21  F  R  K  G  C  N  P  L  A  Q  T  G  R  S  K  L  Q  N  Q  R
 61  TTTCGGAAGGGCTGTAATCCCCTTGCACAAACCGGCCGGAGTAAATTGCAGAATCAAAGA

41  A  A  L  N  Q  Q  I  L  K  A  V  R  M  R  T  G  A  E  N  L
121  GCTGCTTTGAATCAGCAGATCCTGAAAGCCGTGCGGATGAGGACCGGAGCGGAAAACCTT

61  L  K  V  A' T  N  S  K  V  R  E  Q  V  R  L  E  L  S  F  V
181  CTGAAAGTGGCCACAAACTCAAAGGTGCGGGAGCAAGTGCGGCTGGAGCTGAGCTTCGTC

81  N  S  D  L  Q  M  L  K  E  E  L  E  G  L  N  I  S  V  G  V
241  AACTCAGACCTGCAGATGCTCAAGGAAGAGCTGGAGGGGCTGAACATCTCGGTGGGCGTC

101  Y  Q  N  T  E  E  A  F  T  I  P  L  I  P  L  G  L  K  E  T
301  TATCAGAACACAGAGGAGGCATTTACGATTCCCCTGATTCCTCTTGGCCTGAAGGAAACG

121  K  D  V  D  F  A  V  V  L  K  D  P  I  L  E  H  Y  S  E  D
361  AAAGACGTCGACTTTGCAGTCGTCCTCAAGGATTTTATCCTGGAACATTACAGTGAAGAT

141  G  Y  L  Y  E  D  E  I  A  D  L  M  D  L  R  Q  A  C  R  T
421  GGCTATTTATATGAAGATGAAATTGCAGATCTTATGGATCTGAGACAAGCTTGTCGGACG

161  P  S  R  D  E  A  G  V  E  L  L  M  T  Y  F  I  Q  L  G  F
481  CCTAGCCGGGATGAGGCCGGGGTGGAACTGCTGATGACATACTTCATCCAGCTGGGCTTT

181  V  E  S  R  F  F  P  P  T  R  Q  M  G  L  L  F  T  W  Y  D
541  GTCGAGAGTCGATTCTTCCCGCCCACACGGCAGATGGGACTCCTGTTCACCTGGTATGAC

201  S  L  T  G  V  P  V  S  Q  Q  N  L  L  L  E  K  A  S  V  L
601  TCTCTCACTGGGGTTCCGGTCAGCCAGCAGAACCTGCTGCTGGAGAAGGCCAGTGTCCTG

221  F  N  T  G  A  L  Y  T  Q  I  G  T  R  C  D  R  Q  T  Q  A
661  TTCAACACTGGGGCCCTCTACACCCAGATTGGGACCCGGTGCGATCGGCAGACGCAGGCT

241  G  L  E  S  A  I  D  A  F  Q  R  A  A  G  V  L  N  Y  L  K
721  GGGCTGGAGAGTGCCATAGATGCCTTTCAGAGAGCCGCAGGGGTTTTAAATTACCTGAAA

261  D  T  F  T  H  T  P  S  Y  D  M  S  P  A  M  L  S  V  L  V
781  GACACATTTACCCATACTCCAAGTTACGACATGAGCCCTGCCATGCTCAGCGTGCTCGTC

281  K  M  M  L  A  Q  A  Q  E  S  V  F  E  K  I  S  L  P  G  I
841  AAAATGATGCTTGCACAAGCCCAAGAAAGCGTGTTTGAGAAAATCAGCCTTCCTGGGATC

301  R  N  E  F  F  M  L  V  K  V  A  Q  E  A  A  K  V  G  E  V
901  CGGAATGAATTCTTCATGCTGGTGAAGGTGGCTCAGGAGGCTGCTAAGGTGGGAGAGGTC

321  Y  Q  Q  L  H  A  A  M  S  Q  A  P  V  K  E  N  I  P  Y  S
961  TACCAACAGCTACACGCAGCCATGAGCCAGGCGCCGGTGAAAGAGAACATCCCCTACTCC

341  W  A  S  L  A  C  V  K  A  H  H  Y  A  A  L  A  H  Y  F  T
1021 TGGGCCAGCTTAGCCTGCGTGAAGGCCCACCACTACGCGGCCCTGGCCCACTACTTCACT

361  A  I  L  L  I  D  H  Q  V  K  P  G  T  D  L  D  H  Q  E  K
1081 GCCATCCTCCTCATCGACCACCAGGTGAAGCCAGGCACGGATCTGGACCACCAGGAGAAG
```

```
381  C  L  S  Q  L  Y  D  H  M  P  E  G  L  T  P  L  A  T  L  K
1141 TGCCTGTCCCAGCTCTACGACCACATGCCAGAGGGGCTGACACCCTTGGCCACACTGAAG

401  N  D  Q  Q  R  R  Q  L  G  K  S  ·H  L  R  R  A  M  A  H  H
1201 AATGATCAGCAGCGCCGACAGCTGGGGAAGTCCCACTTGCGCAGAGCCATGGCTCATCAC

421  E  E  S  V  R  E  A  S  L  C  K  K  L  R  S  I  E  V  L  Q
1261 GAGGAGTCGGTGCGGGAGGCGAGCCTCTGCAAGAAGCTGCGGAGCATTGAGGTGCTACAG

441  K  V  L  C  A  A  Q  E  R  S  R  L  T  Y  A  Q  H  Q  E  E
1321 AAGGTGCTGTGTGCCGCACAGGAACGCTCCCGGCTCACGTACGCCCAGCACCAGGAGGAG

461  D  D  L  L  N  L  I  D  A  P  S  V  V  A  K  T  E  Q  E  V
1381 GATGACCTGCTGAACCTGATCGACGCCCCCAGTGTTGTTGCTAAAACTGAGCAAGAGGTT

481  D  I  I  L  P  Q  F  S  K  L  T  V  T  D  F  F  Q  K  L  G
1441 GACATTATATTGCCCCAGTTCTCCAAGCTGACAGTCACGGACTTCTTCCAGAAGCTGGGC

501  P  L  S  V  F  S  A  N  K  R  W  T  P  P  R  S  I  R  F  T
1501 CCCTTATCTGTGTTTTCGGCTAACAAGCGGTGGACGCCTCCTCGAAGCATCCGCTTCACT

521  A  E  E  G  D  L  G  F  T  L  R  G  N  A  P  V  Q  V  H  F
1561 GCAGAAGAAGGGGACTTGGGGTTCACCTTGAGAGGGAACGCCCCCGTTCAGGTTCACTTC

541  L  D  P  Y  C  S  A  S  V  A  G  A  R  E  G  D  Y  I  V  S
1621 CTGGATCCTTACTGCTCTGCCTCGGTGGCAGGAGCCCGGGAAGGAGATTATATTGTCTCC

561  I  Q  L  V  D  C  K  W  L  T  S  E  V  M  K  L  L  K  S
1681 ATTCAGCTTGTGGATTGTAAGTGGCTGACGCTGAGTGAGGTTATGAAGCTGCTGAAGAGC

581  P  G  E  D  E  I  E  M  K  V  V  S  L  L  D  S  T  S  S  M
1741 TTTGGCGAGGACGAGATCGAGATGAAAGTCGTGAGCCTCCTGGACTCCACATCATCCATG

601  H  N  K  S  A  T  Y  S  V  G  M  Q  K  T  Y  S  M  I  C  L
1801 CATAATAAGAGTGCCACATACTCCGTGGGAATGCAGAAAACGTACTCCATGATCTGCTTA

621  A  I  D  D  D  D  K  T  D  K  T  K  K  I  S  K  K  L  S  F
1861 GCCATTGATGATGACGACAAAACTGATAAAACCAAGAAAATCTCCAAGAAGCTTTCCTTC

641  L  S  W  G  T  N  K  N  R  Q  K  S  A  S  T  L  C  L  P  S
1921 CTGAGTTGGGGCACCAACAAGAACAGACAGAAGTCAGCCAGCACCTTGTGCCTCCCATCG

661  V  G  A  A  R  P  Q  V  K  K  K  L  P  S  P  F  S  L  L  N
1981 GTCGGGGCTGCACGGCCTCAGGTCAAGAAGAAGCTGCCCTCCCCTTTCAGCCTTCTCAAC

681  S  D  S  S  W  Y  -
2041 TCAGACAGTTCTTGGTACTAATGTGAGGAAACAAACATGTTCAGGCCCCGAACATTTCCG
```

FIGURE 14B

TATA PROMOTER AND PUTATIVE TRANSCRIPTION START SITE
          AAAAAAAATAAATAAAAAGGCCGGGCGCGTTGGCCCGCGCcTGCAGCCCC

PSL 22_5'UTR
    1 TGCTACTTGGGAGGCTGAGGCTGGAGCATCGCTTGATCCTGGGAGGTCGAGGCTGCAAAG
   61 AGTCGAGATCGCAACACTGCTCTCCAGCCTGGGCGACAGAGCGAGGTCCCATCTCTTAAA
  121 AAAAAGAACTGTGCTCAAGGACATCTGCCGTGTCTGGGGCGCAAAACCCCTCCTGGTCCC
  181 CTCTCTCAGGGCAGTCCGCGAGCCCAGCGGATCCCACTCGTCTTTGCAGCGCGGACAGGG
  241 AATCGGCTGAGTTGATCCATGCCAACAAGCCCGAGTAGTCCGGGCAAGGCGCTCGGCGG
  301 GGCAGTCAACGCTCCCTCCGCCATGGGCTCCCCTCTTGGGAAAAGCTTTTCCAAACCGCC
  361 GGGCCCAGGGCCCAGAGCTCCCGCCGCGCCCTCGACGTGGCGTCGAGTCTGGCCCCTTCC
  421 CCCGCGGCGCACGGGCTTCACCCAGGAGGGACGCGCCTGGATCCACGCCTTCCTCACTGA
  481 CTCCCCGGGCTCCAGGGCAGGGTGCAGGTCCACAGCCAGGGCTTCGCTGCGGCCCCTGAG
  541 ACCCCAGTGCCTTTCCTGCGCTCTCGCGGCACTCGCAAAGTTGAGTCAGCCACGACGCCC
  601 ACAGACAACCCCGAGGCGCCGCGCCCAGGGCGCAGCTCTCCGGGTGACGAGCGCCTCAAG
  661 GGGCGCGGGTTCGGGGCCCGCGACGGGGCGGGGCGCGTCTCCAGGGCTCCAGTGCTCGGC
  721 CTCAGGCGGGGCTAGAAGGGCCGCGGGACGGGGTGGGAGTGGAGGGGCGGGGAAGGGCGG
  781 GGACAGGGGCGGGGCCGACGTCCTCTCGGGCCAGCCTCAGCCGCCGCGCCTCAGTCCGC
  841 CGTCCGCCCTCCGCGCCCGCCGCTAGC

EXON_1 69bp
    1 ATGACCGACGCGCTGTTGCCCGCGGCCCCCCAGCCGCTGGAGAAGGAGAACGACGGCTAC
   61 TTTCGGAAG

EXON_2 117bp
    1 GGCTGTAATCCCCTTGCACAAACCGGCCGGAGTAAATTGCAGAATCAAAGAGCTGCTTTG
   61 AATCAGCAGATCCTGAAAGCCGTGCGGATGAGGACCGGAGCGGAAAACCTTCTGAAA

EXON_3 129bp
    1 GTGGCCACAAACTCAAAGGTGCGGGAGCAAGTGCGGCTGGAGCTGAGCTTCGTCAACTCA
   61 GACCTGCAGATGCTCAAGGAAGAGCTGGAGGGGCTGAACATCTCGGTGGGCGTCTATCAG
  121 AACACAGAG

EXON_4 75bp
    1 GAGGCATTTACGATTCCCCTGATTCCTCTTGGCCTGAAGGAAACGAAAGACGTCGACTTT
   61 GCAGTCGTCCTCAAG

EXON_5 79bp
    1 GATTTTATCCTGGAACATTACAGTGAAGATGGCTATTTATATGAAGATGAAATTGCAGAT
   61 CTTATGGATCTGAGACAAG

EXON_6 124bp
    1 CTTGTCGGACGCCTAGCCGGGATGAGGCCGGGGTGGAACTGCTGATGACATACTTCATCC
   61 AGCTGGGCTTTGTCGAGAGTCGATTCTTCCCGCCCACACGGCAGATGGGACTCCTGTTCA
  121 CCTG

EXON_7 167bp
    1 GTATGACTCTCTCACTGGGGTTCCGGTCAGCCAGCAGAACCTGCTGCTGGAGAAGGCCAG
   61 TGTCCTGTTCAACACTGGGGCCCTCTACACCCAGATTGGGACCCGGTGCGATCGGCAGAC
  121 GCAGGCTGGGCTGGAGAGTGCCATAGATGCCTTTCAGAGAGCCGCAG

EXON_8 188bp
    1 GGGTTTTAAATTACCTGAAAGACACATTTACCCATACTCCAAGTTACGACATGAGCCCTG
   61 CCATGCTCAGCGTGCTCGTCAAAATGATGCTTGCACAAGCCCAAGAAAGCGTGTTTGAGA
  121 AAATCAGCCTTCCTGGGATCCGGAATGAATTCTTCATGCTGGTGAAGGTGGCTCAGGAGG
  181 CTGCTAAG
EXON_9 156bp
    1 GTGGGAGAGGTCTACCAACAGCTACACGCAGCCATGAGCCAGGCGCCGGTGAAAGAGAAC

```
    61  ATCCCCTACTCCTGGGCCAGCTTAGCCTGCGTGAAGGCCCACCACTACGCGGCCCTGGCC
   121  CACTACTTCACTGCCATCCTCCTCATCGACCACCAG

EXON_10 120bp
     1  GTGAAGCCAGGCACGGATCTGGACCACCAGGAGAAGTGCCTGTCCCAGCTCTACGACCAC
    61  ATGCCAGAGGGGCTGACACCCTTGGCCACACTGAAGAATGATCAGCAGCGCCGACAGCTG

EXON_11 196bp
     1  GGGAAGTCCCACTTGCGCAGAGCCATGGCTCATCACGAGGAGTCGGTGCGGGAGGCGAGC
    61  CTCTGCAAGAAGCTGCGGAGCATTGAGGTGCTACAGAAGGTGCTGTGTGCCGCACAGGAA
   121  CGCTCCCGGCTCACGTACGCCCAGCACCAGGAGGAGGATGACCTGCTGAACCTGATCGAC
   181  GCCCCCAGTGTTGTTG

EXON_12 77bp
     1  CTAAAACTGAGCAAGAGGTTGACATTATATTGCCCCAGTTCTCCAAGCTGACAGTCACGG
    61  ACTTCTTCCAGAAGCTG

EXON_13 147bp
     1  GGCCCCTTATCTGTGTTTTCGGCTAACAAGCGGTGGACGCCTCCTCGAAGCATCCGCTTC
    61  ACTGCAGAAGAAGGGGACTTGGGGTTCACCTTGAGAGGGAACGCCCCCGTTCAGGTTCAC
   121  TTCCTGGATCCTTACTGCTCTGCCTCG

EXON_14 156bp
     1  GTGGCAGGAGCCCGGGAAGGAGATTATATTGTCTCCATTCAGCTTGTGGATTGTAAGTGG
    61  CTGACGCTGAGTGAGGTTATGAAGCTGCTGAAGAGCTTTGGCGAGGACGAGATCGAGATG
   121  AAAGTCGTGAGCCTCCTGGACTCCACATCATCCATG

EXON_15 +3'UTR 1664bp+polyA tract
     1  CATAATAAGAGTGCCACATACTCCGTGGGAATGCAGAAAACGTACTCCATGATCTGCTTA
    61  GCCATTGATGATGACGACAAAACTGATAAAACCAAGAAAATCTCCAAGAAGCTTTCCTTC
   121  CTGAGTTGGGGCACCAACAAGAACAGACAGAAGTCAGCCAGCACCTTGTGCCTCCCATCG
   181  GTCGGGGCTGCACGGCCTCAGGTCAAGAAGAAGCTGCCCTCCCCTTTCAGCCTTCTCAAC
   241  TCAGACAGTTCTTGGTACTAATGTGAGGAAACAAACATGTTCAGGCCCCGAACATTTCCG
   301  GTGCTGACTCGGCCTTAAACGTTTGTGCCATAATGGAAAATATCTATCTATCTGTTCTCA
   361  AATCCTGTTTTTCTCATAGTGTAAACTCACATTTGATGTGTTTTTATGAAGGAAAGTAAC
   421  CAAGAAACCTCTAGGAATTAGTGAAAAAAGAACTTTTTTGAGGTGTGTTACTATACTGCT
   481  GTAAGTTATTTATTATATAAAGTATTGTAAATAGAATAGTGTTGAAGATATGAAATATGG
   541  CTATTTTTAATGGTGACAATTATGACTTTTAGTCACTATTAAATTGGGGTTACCTATATC
   601  AGTACAATTTGTAGTTGTTTCCAGGTTTGGCTAATAATCATTCCTTAACCTAGAATTCAG
   661  ATGATCCTGGAATTAAGGCAGGTCAGAGGACTGTAATGATAGAATTAAATTAGTGTCACT
   721  AAAAACTGTCCCAAAGTGCTGCTTCCTAATAGGAATTCATTAACCTAAAACAAGATGTTA
   781  CTATTATATCGATAGACTATGAATGCTATTTCTAGAAAAAGTCTAGTGCCAAATTTGTCT
   841  TATTAAATAAAAACAATGTAGGAGCAGCTTTTCTTCTAGTTTGATGTCATTTAAGAATTA
   901  CTAACACAGTGGCAGTGTTAGATGAAGATGCTGTCTACAAGGTAGATAATATACTGTTTG
   961  ATACTCAAAACATTTTTCATTTTGTTTAAAGTAGAAGTTACATAATTCTATATTTTAAGT
  1021  CTTGGGTAAAAAAGTAGTTTTACATTTTATAAAGTAAAGATGTAAATGATTCAGGTTTAA
  1081  AGCTCTATTTGACTTCCTTTTTTTGTTTGAGATAGCGTCTTGCTGTGTTGCCCAGGCTGG
  1141  AGTGCAGTGGTGTGATCTCAGCTCAGTGCAACCTCCGCCCCTGGGATCAAGCGATTCTC
  1201  CTACCTCAGCCTCCCAAATAGCTGGGACTACAAGGTGCCCTCCAGCATGCCTGGCTGATT
  1261  TTTGTATTTTTAGTTGAGGTGAGGTTTCACCATGTTGGCCAGGCGGGTTTCGAAATCCTG
  1321  ACCTCAAATGATCCACCCACCTCAGCCTCCCAAAGTGCTGGGATTACAGGCATGAGCCAC
  1381  CACAACCGTCCCACTATTTTACTTTTTAAAATGACATTCCTACTGATTGATTTTTATCTT
  1441  GCTATAAGTTCGATGACACCGTGAATCTAATAAGGTTCACTGTTGACACAGTACAAGTTA
  1501  CATAGCTAAAATACATAGCATTGAAGACTAATTTTAAGGATTGACAAGAGTTTATTTTCT
  1561  ATTGTGCAATATCTTAAAGGAAGCAACCACCTTTGGGAAAGTGTATCTGCTGCTCCTAGG
  1621  GCCATGCTTGTATACATATTTaaataaACATATTCATTTACCCGAAAAAAAAAAAAAAAA
  1681  AAAAAAAAAAAAAAAAAAAAAAAAAAAAAAAAAAAAAAAAAAAA
```

FIGURE 14C

SEQUENCE LISTING

<160> NUMBER OF SEQ ID NOS: 73

<210> SEQ ID NO 1

```
<211> LENGTH: 349
<212> TYPE: DNA
<213> ORGANISM: Homo sapiens

<400> SEQUENCE: 1
actaatgtga ggaaacaaac atgttcaggc ctgaacattt ccggtgctga ctcggcctta      60
aacgtttgtg ccataatgga aaatatctat ctatctgttc tcaaatcctg tttttctcat     120
agtgtaaact cacatttgat gtgttttat gaaggaaagt aaccaagaaa cctctaggaa      180
ttaggaaaaa aagaactttt ttgaggtgtg ttactatact gctgtaagtt atttattata     240
taaagtattg taaatagaaa tagtgttgag atatgaaata tggctatttt taatggtgac     300
aattatagac ttttaggtca ctattaaatt ggggttacct atatccagt                349

<210> SEQ ID NO 2
<211> LENGTH: 251
<212> TYPE: DNA
<213> ORGANISM: Homo sapiens

<400> SEQUENCE: 2
acacatccat cattgtgaaa tctctttttcc aacaaacgtc tcttaatga gcacaattca      60 ttaaaatctt tggggactaa gctacgaaca aagttcaact aaactaccta ctgacttcaa     120
aaggaacata tacccaccac gtgtggtagc tcatgactgt aatcccagca ctttgggagg     180
ctgaggcagg aggatcacct gagcccagga gttccagacc agcctaagca acatgccaag     240
accctgtatg t                                                         251

<210> SEQ ID NO 3
<211> LENGTH: 51
<212> TYPE: DNA
<213> ORGANISM: Homo sapiens

<400> SEQUENCE: 3
acaaagacac ccttgtyccc cgggcaaggt cctccagcta caaggggcc a                51

<210> SEQ ID NO 4
<211> LENGTH: 149
<212> TYPE: DNA
<213> ORGANISM: Homo sapiens
<220> FEATURE:
<221> NAME/KEY: misc_feature
<222> LOCATION: 3
<223> OTHER INFORMATION: n = A,T,C or G

<400> SEQUENCE: 4
ccnyacattg tcacagagag gctccaggct taaagttgac ctgcgtagaa agcaagaatg      60
aattgttgga ggaagtaagg agggcgattg aataaagact tttagcagct gggccagctg     120
aaccatccca acccttcaaa tccccttgt                                       149

<210> SEQ ID NO 5
<211> LENGTH: 261
<212> TYPE: DNA
<213> ORGANISM: Homo sapiens

<400> SEQUENCE: 5
accctaactg aacccatttc agccactcag attgataggg tggaaaagac agggcaggtg      60
gtagcagctg tgaagaaaag aggaaagcag aagggtggcc tataatctac aggcatgtag     120
agaggactac ataggcctct gttctttgcc ctcaggagcc ccttcctgt ccctggact       180 cagaatggat ccttccagca cacatggccc aacactgaga gtgcaggaag catgggtagg     240
```

```
ggcctcctgc tgctggtatg t                                             261

<210> SEQ ID NO 6
<211> LENGTH: 121
<212> TYPE: DNA
<213> ORGANISM: Homo sapiens
<220> FEATURE:
<221> NAME/KEY: misc_feature
<222> LOCATION: 4, 7, 13, 22, 24, 29, 30, 34, 36, 40, 46, 111, 112
<223> OTHER INFORMATION: n = A,T,C or G

<400> SEQUENCE: 6
agtntgnggg ganttgaggg cngntacgnn aaangntggn ctactntaga tgctgctcga    60
gcggccgcca gtgtgatgga tacaagcttt cttttttttt tttattttcg nntttttttt   120
c                                                                   121

<210> SEQ ID NO 7
<211> LENGTH: 93
<212> TYPE: DNA
<213> ORGANISM: Homo sapiens

<400> SEQUENCE: 7
actcagtagg gactgagcac taaatgctta ttttaaaaga aatgtaaaga gcagaaagca    60
attcaggcta ccctgccttt tgtgctggct agt                                93

<210> SEQ ID NO 8
<211> LENGTH: 169
<212> TYPE: DNA
<213> ORGANISM: Homo sapiens

<400> SEQUENCE: 8
acacttaaaa tagttaatgt gatacatttt atgttacatg tattttgccc actgaaaaaa    60
taaaaatata taaacacaca gcaaatgatg accaggcctt tgaagaaagc ttataaaaca   120
aaattaagaa gcctggctac agagcgagac tctgtctcaa aaaaaaaa                169

<210> SEQ ID NO 9
<211> LENGTH: 262
<212> TYPE: DNA
<213> ORGANISM: Homo sapiens

<400> SEQUENCE: 9
actttacaag catgaaggat attagggtaa gtggctaatt ataaatctac tctagagaca    60
tataatcata cagattattc ataaaatttt tcagtgctgt ccttccacat ttaattgcat   120
tttgctcaaa ctgtagaatg ccctacattc ccccacccc aatttgctat ttccttatta    180
aaatagaaaa ttataggcaa gatacaatta tatgcgttcc tcttcctgaa attataacat   240
ttctaaactt acccacgtag gt                                            262

<210> SEQ ID NO 10
<211> LENGTH: 175
<212> TYPE: DNA
<213> ORGANISM: Homo sapiens

<400> SEQUENCE: 10
acaggttggc ccttcaccta gttgactcag ccctcgatag tctagagccc accccctcct    60
caggaactca agagctcagc atttataatg agcagttggt aatgagttgc cctatgtgct   120
tgtcgcaagc agtcacagag atgagcccta ttacttgata ttcaggaaca aagt         175
```

<210> SEQ ID NO 11
<211> LENGTH: 331
<212> TYPE: DNA
<213> ORGANISM: Homo sapiens

<400> SEQUENCE: 11

```
acatccaagc cttcctctgc gtgagagcaa aggctttgct catcagccag ccagtcttgt    60
tactatctgg ctactttta aggttaaaaa ataaaaggca gtttctttgc tctgcaggcg   120
gcaaggcagg aggcgcaggc ctcttcattg ttcacatgtc acaggaggag gctctgagca   180
aaggccactg gcaagttagg gcaacaccaa gaaggctctg cggagagact ccctgtgggt   240
tgggggsctg gcaggaacgg tgcctgtgga ctgtttatgg tctgtccagt tgaggcttgg   300
taaacccaag taaagtgtta aaaacctcag t                                  331
```

<210> SEQ ID NO 12
<211> LENGTH: 170
<212> TYPE: DNA
<213> ORGANISM: Homo sapiens

<400> SEQUENCE: 12

```
acgactcatc cacctccggc tgaagctcca ggagctgaag daccccaatg aggatgagcc    60
aaacatccga gtgctccttg agcaccgctt ttacaaggag aagagcaaga gcgtcaagca   120
gacctgtgac aagtgtaaca ccatcatctg ggggctcatt cagacctggt               170
```

<210> SEQ ID NO 13
<211> LENGTH: 88
<212> TYPE: DNA
<213> ORGANISM: Homo sapiens

<400> SEQUENCE: 13

```
acgcggggga tccagcttgg gtaggcgggg aagcagctgg agtgcgaccg ctacggcagc    60
caccctgcaa ccgccagtcg gaggtgca                                       88
```

<210> SEQ ID NO 14
<211> LENGTH: 490
<212> TYPE: PRT
<213> ORGANISM: Homo sapiens

<400> SEQUENCE: 14

Met Glu Ser Ile Ser Met Met Gly Ser Pro Lys Ser Leu Ser Glu Thr
1               5                   10                  15

Cys Leu Pro Asn Gly Ile Asn Gly Ile Lys Asp Ala Arg Lys Val Thr
            20                  25                  30

Val Gly Val Ile Gly Ser Gly Asp Phe Ala Lys Ser Leu Thr Ile Arg
        35                  40                  45

Leu Ile Arg Cys Gly Tyr His Val Val Ile Gly Ser Arg Asn Pro Lys
    50                  55                  60

Phe Ala Ser Glu Phe Phe Pro His Val Val Asp Val Thr His His Glu
65                  70                  75                  80

Asp Ala Leu Thr Lys Thr Asn Ile Ile Phe Val Ala Ile His Arg Glu
                85                  90                  95

His Tyr Thr Ser Leu Trp Asp Leu Arg His Leu Leu Val Gly Lys Ile
            100                 105                 110

Leu Ile Asp Val Ser Asn Asn Met Arg Ile Asn Gln Tyr Pro Glu Ser
        115                 120                 125

Asn Ala Glu Tyr Leu Ala Ser Leu Phe Pro Asp Ser Leu Ile Val Lys

-continued

```
            130                 135                 140
Gly Phe Asn Val Val Ser Ala Trp Ala Leu Gln Leu Gly Pro Lys Asp
145                 150                 155                 160

Ala Ser Arg Gln Val Tyr Ile Cys Ser Asn Asn Ile Gln Ala Arg Gln
                165                 170                 175

Gln Val Ile Glu Leu Ala Arg Gln Leu Asn Phe Ile Pro Ile Asp Leu
            180                 185                 190

Gly Ser Leu Ser Ser Ala Arg Glu Ile Glu Asn Leu Pro Leu Arg Leu
        195                 200                 205

Phe Thr Phe Trp Arg Gly Pro Val Val Ala Ile Ser Leu Ala Thr
210                 215                 220

Phe Phe Phe Leu Tyr Ser Phe Val Arg Asp Val Ile His Pro Tyr Ala
225                 230                 235                 240

Arg Asn Gln Gln Ser Asp Phe Tyr Lys Ile Pro Ile Glu Ile Val Asn
                245                 250                 255

Lys Thr Leu Pro Ile Val Ala Ile Thr Leu Leu Ser Leu Val Tyr Leu
            260                 265                 270

Ala Gly Leu Leu Ala Ala Tyr Gln Leu Tyr Tyr Gly Thr Lys Tyr
        275                 280                 285

Arg Arg Phe Pro Pro Trp Leu Glu Thr Trp Leu Gln Cys Arg Lys Gln
290                 295                 300

Leu Gly Leu Leu Ser Phe Phe Ala Met Val His Val Ala Tyr Ser
305                 310                 315                 320

Leu Cys Leu Pro Met Arg Arg Ser Glu Arg Tyr Leu Phe Leu Asn Met
                325                 330                 335

Ala Tyr Gln Gln Val His Ala Asn Ile Glu Asn Ser Trp Asn Glu Glu
            340                 345                 350

Glu Val Trp Arg Ile Glu Met Tyr Ile Ser Phe Gly Ile Met Ser Leu
        355                 360                 365

Gly Leu Leu Ser Leu Leu Ala Val Thr Ser Ile Pro Ser Val Ser Asn
370                 375                 380

Ala Leu Asn Trp Arg Glu Phe Ser Phe Ile Gln Ser Thr Leu Gly Tyr
385                 390                 395                 400

Val Ala Leu Leu Ile Ser Thr Phe His Val Leu Ile Tyr Gly Trp Lys
                405                 410                 415

Arg Ala Phe Glu Glu Glu Tyr Tyr Arg Phe Tyr Thr Pro Pro Asn Phe
            420                 425                 430

Val Leu Ala Leu Val Leu Pro Ser Ile Val Ile Leu Gly Lys Ile Ile
        435                 440                 445

Leu Phe Leu Pro Cys Ile Ser Arg Lys Leu Lys Arg Ile Lys Lys Gly
450                 455                 460

Trp Glu Lys Ser Gln Phe Leu Glu Glu Gly Ile Gly Gly Thr Ile Pro
465                 470                 475                 480

His Val Ser Pro Glu Arg Val Thr Val Met
                485                 490
```

<210> SEQ ID NO 15
<211> LENGTH: 83
<212> TYPE: DNA
<213> ORGANISM: Homo sapiens

<400> SEQUENCE: 15
acgcggggga tccagcttgg gtaggcgggg aagcagctgg agtgcgaccg ctacggcagc    60
caccctgcaa ccgccagtcg gag                                           83

<210> SEQ ID NO 16
<211> LENGTH: 61
<212> TYPE: DNA
<213> ORGANISM: Homo sapiens

<400> SEQUENCE: 16

```
agctaagggc aagtcctgag gttgggccca ggagaaagaa ggcaaggaga cattgtccca   60
g                                                                  61
```

<210> SEQ ID NO 17
<211> LENGTH: 525
<212> TYPE: DNA
<213> ORGANISM: Homo sapiens

<400> SEQUENCE: 17

```
gatattcttg gtgatcttgg aagtgtccgt atcatggaat caatctctat gatgggaagc   60
cctaagagcc ttagtgaaac ttttttacct aatggcataa atggtatcaa agatgcaagg  120
aaggtcactg taggtgtgat tggaagtgga gattttgcca atccttgac cattcgactt   180
attagatgcg gctatcatgt ggtcatagga agtagaaatc ctaagtttgc ttctgaattt  240
tttcctcatg tggtagatgt cactcatcat gaagatgctc tcacaaaaac aaatataata  300
tttgttgcta tacacagaga acattatacc tccctgtggg acctgagaca tctgcttgtg  360
ggtaaaatcc tgattgatgt gagcaataac atgaggataa accagtaccc agaatccaat  420
gctgaatatt tggcttcatt attcccagat tctttgattg tcaaaggatt taatgttgtc  480
tcagcttggg cacttcagtt aggacctaag gatgccagcc ggcag                  525
```

<210> SEQ ID NO 18
<211> LENGTH: 528
<212> TYPE: DNA
<213> ORGANISM: Homo sapiens

<400> SEQUENCE: 18

```
gtttatatat gcagcaacaa tattcaagcg cgacaacagg ttattgaact tgcccgccag   60
ttgaatttca ttcccattga cttgggatcc ttatcatcag ccagagagat tgaaaattta  120
cccctacgac tctttactct ctggagaggg ccagtggtgg tagctataag cttggccaca  180
tttttttttcc tttattcctt tgtcagagat gtgattcatc catatgctag aaaccaacag  240
agtgactttt acaaaattcc tatagagatt gtgaataaaa ccttacctat agttgccatt  300
actttgctct ccctagtata cctcgcaggt cttctggcag ctgcttatca actttattac  360
ggcaccaagt ataggagatt ccaccttgg ttggaaacct ggttacagtg tagaaaacag  420
cttggattac taagtttttt cttcgctatg gtccatgttg cctacagcct ctgcttaccg  480
atgagaaggt cagagagata tttgtttctc aacatggctt atcagcag               528
```

<210> SEQ ID NO 19
<211> LENGTH: 165
<212> TYPE: DNA
<213> ORGANISM: Homo sapiens

<400> SEQUENCE: 19

```
gttcatgcaa atattgaaaa ctcttggaat gaggaagaag tttggagaat tgaaatgtat   60
atctcctttg gcataatgag ccttggctta cttccctcc tggcagtcac ttctatccct  120
tcagtgagca atgctttaaa ctggagagaa ttcagtttta ttcag                  165
```

<210> SEQ ID NO 20
<211> LENGTH: 148
<212> TYPE: DNA
<213> ORGANISM: Homo sapiens

<400> SEQUENCE: 20

| | | | | | |
|---|---|---|---|---|---|
| tctacacttg | gatatgtcgc | tctgctcata | agtactttcc | atgtttttaat | ttatggatgg | 60 |
| aaacgagctt | ttgaggaaga | gtactacaga | ttttatacac | caccaaactt | tgttcttgct | 120 |
| cttgttttgc | cctcaattgt | aattctgg | | | | 148 |

<210> SEQ ID NO 21
<211> LENGTH: 2381
<212> TYPE: DNA
<213> ORGANISM: Homo sapiens

<400> SEQUENCE: 21

| | | | | | |
|---|---|---|---|---|---|
| gtaagattat | tttattcctt | ccatgtataa | gccgaaagct | aaaacgaatt | aaaaaaggct | 60 |
| gggaaaagag | ccaatttctg | gaagaaggta | ttggaggaac | aattcctcat | gtctccccgg | 120 |
| agagggtcac | agtaatgtga | tgataaatgg | tgttcacagc | tgccatataa | agttctactc | 180 |
| atgccattat | ttttatgact | tctacgttca | gttacaagta | tgctgtcaaa | ttatcgtggg | 240 |
| ttgaaacttg | ttaaatgaga | tttcaactga | cttagtgata | gagttttctt | caagttaatt | 300 |
| ttcacaaatg | tcatgtttgc | caatatgaat | ttttctagtc | aacatattat | tgtaatttag | 360 |
| gtatgttttg | ttttgttttg | cacaactgta | accctgttgt | tactttatat | ttcataatca | 420 |
| gacaaaaata | cttacagtta | ataatataga | tataatgtta | aaaacaattt | gcaaaccagc | 480 |
| agaattttaa | gcttttaaaa | taattcaatg | gatatacatt | tttttctgaa | gattaagatt | 540 |
| ttaattattc | aacttaaaaa | gtagaaatgc | attattatac | attttttaa | gaaaggacac | 600 |
| gttatgttag | catctaggta | aggctgcatg | atagcattcc | tatatttctc | tcataaaata | 660 |
| ggatttgaag | gatgaaatta | attgtatgaa | gcaatgtgat | tatatgaaga | gacacaaatt | 720 |
| aaaaagacaa | attaaacctg | aaattatatt | taaaatatat | ttgagacatg | aaatacatac | 780 |
| tgataataca | tacctcatga | aagattttat | tctttattgt | gttacagagc | agtttcattt | 840 |
| tcatattaat | atactgatca | ggaagaggat | tcagtaacat | ttggcttcca | aaactgctat | 900 |
| ctctaatacg | gtaccaatcc | taggaactgt | atactagttc | ctacttagaa | caaaagtatc | 960 |
| aagtttgcac | acaagtaatc | tgccagctga | cctttgtcgc | accttaacca | gtcaccactt | 1020 |
| gctatggtat | aggattatac | tgatgttctt | tgagggattc | tgatgtgcta | ggcatggttc | 1080 |
| taagtacttt | acttgtatta | tcccatttaa | tacttagaac | aaccccgtga | gataagtagt | 1140 |
| tattatcctc | attttacaca | tgagggaccg | aaggatagaa | aagttatttt | tcaaaggtct | 1200 |
| tgcagttaat | aaatggcaga | gtgagcattc | aagtccaggt | agtcatattc | cagaggccac | 1260 |
| ggttttaacc | actaggctct | agagctcccg | ccgcgcccct | atgcattatg | ttcacaatgc | 1320 |
| caatctagat | gcttcctctt | ttgtataaag | tcactgacat | tctttagagt | gggttgggtg | 1380 |
| catccaaaaa | tgtataaaaa | tattattata | ataaacttat | tactgcttgt | agggtaattc | 1440 |
| acagttactt | accctattct | tgcttggaac | atgagcctgg | agacccatgg | cagtccatat | 1500 |
| gcctccctat | gcagtgaagg | gccctagcag | tgttaacaaa | ttgctgagat | cccacgagt | 1560 |
| ctttcaaaaa | tctctgtaga | gttagtcttc | tccttttctc | ttcctgagaa | gttctcctgc | 1620 |
| ctgcataacc | attcattagg | gagtacttta | caagcatgaa | ggatattagg | gtaagtggct | 1680 |
| aattataaat | ctactctaga | gacatataat | catacagatt | attcataaaa | tttttcagtg | 1740 |

-continued

```
ctgtccttcc acatttaatt gcattttgct caaactgtag aatgccctac attcccccca    1800
ccccaatttg ctatttcctt attaaaatag aaaattatag gcaagataca attatatgcg    1860
ttcctcttcc tgaaattata acatttctaa acttacccac gtagggacta ctgaatccaa    1920
ctgccaacaa taaaaagact tttatttagt agaggctacc tttcccccca gtgactcttt    1980
ttctacaact gccttgtcag tttggtaatt cacttatgat tttctaatgt tctcttggtg    2040
aattttatta tcttggaccc tcttttttt ttttttttaaa gacagagtct tgctctgtca    2100
cccattgctc tcgtttgggc aacaagagtg aaactcttgt ctcaaaaaaa aaaaaaatg     2160 aggtttaaga cagttttgtc attactggtg ggatctggtc acacaagata gcattaaacg    2220
tgacatggca cataaaattg gttaaaaaat tttgttttttt aattgcgtaa tgtaaaagcc    2280
caacaaacac tttatgcaag attggaatgt atcttcaaat tcagatttaa taaacatgta    2340
aagatcctct gtaaaaaaaa aaaaaaaaaa aaaaaaaaa a                         2381
```

<210> SEQ ID NO 22
<211> LENGTH: 4329
<212> TYPE: DNA
<213> ORGANISM: Homo sapiens

<400> SEQUENCE: 22

```
acgcggggga tccagcttgg gtaggcgggg aagcagctgg agtgcgaccg ctacggcagc      60
caccctgcaa ccgccagtcg gagagctaag ggcaagtcct gaggttgggc ccaggagaaa    120
gaaggcaagg agacattgtc ccaggatatt cttggtgatc ttggaagtgt ccgtatcatg    180
gaatcaatct ctatgatggg aagccctaag agccttagtg aaacttgttt acctaatggc    240
ataaatggta tcaaagatgc aaggaaggtc actgtaggtg tgattggaag tggagatttt    300
gccaaatcct tgaccattcg acttattaga tgcggctatc atgtggtcat aggaagtaga    360
aatcctaagt ttgcttctga atttttttcct catgtggtag atgtcactca tcatgaagat    420
gctctcacaa aaacaaatat aatatttgtt gctatacaca gagaacatta tacctccctg    480
tgggacctga gacatctgct tgtgggtaaa atcctgattg atgtgagcaa taacatgagg    540
ataaaccagt acccagaatc caatgctgaa tatttggctt cattattccc agattctttg    600
attgtcaaag gatttaatgt tgtctcagct tgggcacttc agttaggacc taaggatgcc    660
agccggcagg tttatatatg cagcaacaat attcaagcgc gacaacaggt tattgaactt    720
gcccgccagt tgaatttcat tcccattgac ttgggatcct tatcatcagc cagagagatt    780
gaaaatttac ccctacgact ctttactttc tggagagggc cagtggtggt agctataagc    840
ttggccacat tttttttcct ttattccttt gtcagagatg tgattcatcc atatgctaga    900
aaccaacaga gtgactttta caaaattcct atagagattg tgaataaaac cttacctata    960
gttgccatta ctttgctctc cctagtatac cttgcaggtc ttctggcagc tgcttatcaa    1020
ctttattacg gcaccaagta taggagattt ccaccttggt tggaaacctg gttacagtgt    1080
agaaaacagc ttggattact aagttttttttc ttcgctatgg tccatgttgc ctacagcctc    1140
tgcttaccga tgagaaggtc agagagatat ttgtttctca acatggctta tcagcaggtt    1200
catgcaaata ttgaaaactc ttggaatgag gaagaagttt ggagaattga aatgtatatc    1260
tcctttggca taatgagcct tggcttactt tccctcctgg cagtcacttc tatcccttca    1320
gtgagcaatg ccttaaactg gagagaattc agttttattc agtctacact tggatatgtc    1380
gctctgctca taagtacttt ccatgttttta atttatggat ggaaacgagc ttttgaggaa    1440
```

-continued

```
gagtactaca gattttatac accaccaaac tttgttcttg ctcttgtttt gccctcaatt    1500
gtaattctgg gtaagattat tttattcctt ccatgtataa gccgaaagct aaaacgaatt    1560
aaaaaaggct gggaaaagag ccaatttctg gaagaaggta ttggaggaac aattcctcat    1620
gtctccccgg agagggtcac agtaatgtga tgataaatgg tgttcacagc tgccatataa    1680
agttctactc atgccattat ttttatgact tctacgttca gttacaagta tgctgtcaaa    1740
ttatcgtggg ttgaaacttg ttaaatgaga tttcaactga cttagtgata gagttttctt    1800
caagttaatt ttcacaaatg tcatgtttgc caatatgaat ttttctagtc aacatattat    1860
tgtaatttag gtatgttttg ttttgttttg cacaactgta accctgttgt tactttatat    1920
ttcataatca gacaaaaata cttacagtta ataatataga tataatgtta aaaacaattt    1980
gcaaaccagc agaattttaa gctttttaaaa taattcaatg gatatacatt tttttctgaa    2040
gattaagatt ttaattattc aacttaaaaa gtagaaatgc attattatac attttttttaa    2100 gaaaggacac gttatgttag catctaggta aggctgcatg atagcattcc tatatttctc    2160
tcataaaata ggatttgaag gatgaaatta attgtatgaa gcaatgtgat tatatgaaga    2220
gacacaaatt aaaagacaa attaaacctg aaattatatt taaatatat ttgagacatg    2280 aaatacatac tgataataca tacctcatga aagatttat tctttattgt gttacagagc    2340
agtttcattt tcatattaat atactgatca ggaagaggat tcagtaacat ttggcttcca    2400
aaactgctat ctctaatacg gtaccaatcc taggaactgt atactagttc ctacttagaa    2460
caaaagtatc aagtttgcac acaagtaatc tgccagctga cctttgtcgc accttaacca    2520
gtcaccactt gctatggtat aggattatac tgatgttctt tgagggattc tgatgtgcta    2580
ggcatggttc taagtacttt acttgtatta tcccatttaa tacttagaac aaccccgtga    2640
gataagtagt tattatcctc attttacaca tgagggaccg aaggatagaa aagttatttt    2700
tcaaaggtct tgcagttaat aaatggcaga gtgagcattc aagtccaggt agtcatattc    2760
cagaggccac ggttttaacc actaggctct agagctcccg ccgcgcccct atgcattatg    2820
ttcacaatgc caatctagat gcttcctctt ttgtataaag tcactgacat tctttagagt    2880
gggttgggtg catccaaaaa tgtataaaaa tattattata ataaacttat tactgcttgt    2940
agggtaattc acagttactt accctattct tgcttggaac atgagcctgg agacccatgg    3000
cagtccatat gcctccctat gcagtgaagg gccctagcag tgttaacaaa ttgctgagat    3060
cccacggagt ctttcaaaaa tctctgtaga gttagtcttc tccttttctc ttcctgagaa    3120
gttctcctgc ctgcataacc attcattagg gagtacttta caagcatgaa ggatattagg    3180
gtaagtggct aattataaat ctactctaga gacatataat catacagatt attcataaaa    3240
tttttcagtg ctgtccttcc acatttaatt gcattttgct caaactgtag aatgccctac    3300
attcccccca ccccaatttg ctatttcctt attaaaaatg tataaaaata ttattataat    3360
aaacttatta ctgcttgtag ggtaattcac agttacttac cctattcttg cttggaacat    3420
gagcctggag acccatggca gtccatatgc ctccctatgc agtgaagggc cctagcagtg    3480
ttaacaaatt gctgagatcc cacggagtct ttcaaaaatc tctgtagagt tagtcttctc    3540
cttttctctt cctgagaagt tctcctgcct gcataaccat tcattaggga gtactttaca    3600
agcatgaaga tattagggt aagtggctaa ttataaatct actctagaga catataatca    3660
tacagattat tcataaaatt tttcagtgct gtccttccac atttaattgc attttgctca    3720
aactgtagaa tgccctacat tcccccccacc ccaatttgct atttccttat taaaatagaa    3780
aattataggc aagatacaat tatatgcgtt cctcttcctg aaattataac atttctaaac    3840
```

-continued

```
ttacccacgt agggactact gaatccaact gccaacaata aaaagacttt tatttagtag    3900
aggctacctt tccccccagt gactcttttt ctacaactgc cttgtcagtt tggtaattca    3960
cttatgattt tctaatgttc tcttggtgaa ttttattatc ttggaccctc tttttttttt    4020
tttttaaaga cagagtcttg ctctgtcacc cattgctctc gtttgggcaa caagagtgaa    4080
actcttgtct caaaaaaaaa aaaaatgag gtttaagaca gttttgtcat tactggtggg     4140
atctggtcac acaagatagc attaaacgtg acatggcaca taaaattggt taaaaatttt    4200
tgtttttttaa ttgcgtaatg taaaagccca acaaacactt tatgcaagat tggaatgtat   4260
cttcaaattc agatttaata aacatgtaaa gatcctctgt aaaaaaaaaa aaaaaaaaa     4320
aaaaaaaaa                                                            4329
```

<210> SEQ ID NO 23
<211> LENGTH: 1680
<212> TYPE: DNA
<213> ORGANISM: Homo sapiens

<400> SEQUENCE: 23

```
acgcggggga tccagcttgg gtaggcgggg aagcagctgg agtgcgaccg ctacggcagc      60
caccctgcaa ccgccagtcg gagagctaag ggcaagtcct gaggttgggc ccaggagaaa    120
gaaggcaagg agacattgtc ccaggatatt cttggtgatc ttggaagtgt ccgtatcatg    180
gaatcaatct ctatgatggg aagccctaag agccttagtg aaacttgttt acctaatggc    240
ataaatggta tcaaagatgc aaggaaggtc actgtaggtg tgattggaag tggagatttt    300
gccaaatcct tgaccattcg acttattaga tgcggctatc atgtggtcat aggaagtaga    360
aatcctaagt ttgcttctga attttttcct catgtggtag atgtcactca tcatgaagat    420
gctctcacaa aaacaaatat aatatttgtt gctatacaca gagaacatta tacctccctg    480
tgggacctga gacatctgct tgtgggtaaa atcctgattg atgtgagcaa taacatgagg    540
ataaaccagt acccagaatc caatgctgaa tatttggctt cattattccc agattctttg    600
attgtcaaag gatttaatgt tgtctcagct tgggcacttc agttaggacc taaggatgcc    660
agccggcagg tttatatatg cagcaacaat attcaagcgc gacaacaggt tattgaactt    720
gcccgccagt tgaatttcat tcccattgac ttggatcct tatcatcagc cagagagatt     780
gaaaatttac ccctacgact ctttactttc tggagagggc cagtggtggt agctataagc    840
ttggccacat tttttttcct ttattccttt gtcagagatg tgattcatcc atatgctaga    900
aaccaacaga gtgactttta caaaattcct atagagattg tgaataaaac cttacctata    960
gttgccatta ctttgctctc cctagtatac cttgcaggtc ttctggcagc tgcttatcaa   1020
ctttattacg gcaccaagta taggagattt ccaccttggt tggaaacctg gttacagtgt   1080
agaaaacagc ttggattact aagttttttc ttcgctatgg tccatgttgc ctacagcctc   1140
tgcttaccga tgagaaggtc agagagatat tgtttctca acatggctta tcagcaggtt    1200
catgcaaata ttgaaaactc ttggaatgag gaagaagttt ggagaattga atgtatatc    1260
tcctttggca taatgagcct tggcttactt tccctcctgg cagtcacttc tatcccttca   1320
gtgagcaatg ccttaaactg gagagaattc agtttttatt cagtctacact tggatatgtc   1380
gctctgctca aagtactttt ccatgttttta atttatggat ggaaacgagc ttttgaggaa   1440
gagtactaca gatttatac accaccaaac tttgttcttg ctcttgtttt gccctcaatt    1500
gtaattctgg gtaagattat tttattcctt ccatgtataa gccgaaagct aaaacgaatt   1560
```

```
aaaaaaggct gggaaaagag ccaatttctg gaagaaggta ttggaggaac aattcctcat    1620
gtctccccgg agagggtcac agtaatgtga tgataaatgg tgttcacagc tgccatataa    1680

<210> SEQ ID NO 24
<211> LENGTH: 75
<212> TYPE: DNA
<213> ORGANISM: Homo sapiens

<400> SEQUENCE: 24
gatccagctt gggtaggcgg ggaagcagct ggagtgcgac cgccgcggca gccaccctgc      60
aaccgccagt cggag                                                      75

<210> SEQ ID NO 25
<211> LENGTH: 79
<212> TYPE: DNA
<213> ORGANISM: Homo sapiens

<400> SEQUENCE: 25
agagctaagg gcaagtcctg aggttgggcc caggagaaag aaggcaagga gacattgtcc      60
caggtaggat gtgtcccag                                                  79

<210> SEQ ID NO 26
<211> LENGTH: 718
<212> TYPE: DNA
<213> ORGANISM: Homo sapiens

<400> SEQUENCE: 26
atcttttgca gctttgcaga tacccagact gagctggaac tggaatttgt cttcctattg      60
actctacttc tttaaaagcg gctgcccatt acattcctca gctgtccttg cagttaggtg     120
tacatgtgac tgagtgttgg ccagtgagat gaagtctcct caaaggaagg cagcatgtgt     180 ccttttttcat cccttcatct tgctgctggg attgtggata taacaggagc cctggcagct     240
gtctccagag gatcaaagcc acacccaaag agtaaggcag attagagacc agaaagacct     300
tgactacttc cctacttcca ctgctttttc ctgcatttaa gccattgtaa atctgggtgt     360
gttacatgaa gtgaaaatta attctttctg cccttcagtt ctttatcctg ataccattta     420
acactgtctg aattaactag actgcaataa ttctttcttt tgaaagcttt taaaggataa     480
tgtgcaattc acattaaaat tgattttcca ttgtcaatta gttatactca ttttcctgcc     540
ttgatctttc attagatatt ttgtatctgc ttggaatata ttatcttctt tttaactgtg     600
taattggtaa ttactaaaac tctgtaatct ccaaaatatt gctatcaaat tacacaccat     660
gttttctatc attctcatag atctgcctta taaacattta ataaaaagt actattta       718

<210> SEQ ID NO 27
<211> LENGTH: 2238
<212> TYPE: DNA
<213> ORGANISM: Homo sapiens

<400> SEQUENCE: 27
gatccagctt gggtaggcgg ggaagcagct ggagtgcgac cgccgcggca gccaccctgc      60
aaccgccagt cggagagagc taagggcaag tcctgaggtt gggcccagga gaaagaaggc     120
aaggagacat tgtcccaggt aggatgtgtc ccaggatatt cttggtgatc ttggaagtgt     180
ccgtatcatg gaatcaatct ctatgatggg aagccctaag agccttagtg aaacttttt      240 acctaatggc ataatggta tcaaagatgc aaggaaggtc actgtaggtg tgattggaag     300
tggagatttt gccaaatcct tgaccattcg acttattaga tgcggctatc atgtggtcat     360
```

-continued

| | | | | | |
|---|---|---|---|---|---|
| aggaagtaga | aatcctaagt | ttgcttctga | atttttcct | catgtggtag | atgtcactca | 420 |
| tcatgaagat | gctctcacaa | aaacaaatat | aatatttgtt | gctatacaca | gagaacatta | 480 |
| tacctccctg | tgggacctga | gacatctgct | tgtgggtaaa | atcctgattg | atgtgagcaa | 540 |
| taacatgagg | ataaaccagt | acccagaatc | caatgctgaa | tatttggctt | cattattccc | 600 |
| agattctttg | attgtcaaag | gatttaatgt | tgtctcagct | tgggcacttc | agttaggacc | 660 |
| taaggatgcc | agccggcagg | tttatatatg | cagcaacaat | attcaagcgc | gacaacaggt | 720 |
| tattgaactt | gcccgccagt | tgaatttcat | tcccattgac | ttgggatcct | tatcatcagc | 780 |
| cagagagatt | gaaaatttac | ccctacgact | ctttactctc | tggagagggc | cagtggtggt | 840 |
| agctataagc | ttggccacat | tttttttcct | ttattccttt | gtcagagatg | tgattcatcc | 900 |
| atatgctaga | aaccaacaga | gtgactttta | caaaattcct | atagagattg | tgaataaaac | 960 |
| cttacctata | gttgccatta | ctttgctctc | cctagtatac | ctcgcaggtc | ttctggcagc | 1020 |
| tgcttatcaa | ctttattacg | gcaccaagta | taggagattt | ccaccttggt | tggaaacctg | 1080 |
| gttacagtgt | agaaaacagc | ttggattact | aagtttttc | ttcgctatgg | tccatgttgc | 1140 |
| ctacagcctc | tgcttaccga | tgagaaggtc | agagagatat | ttgtttctca | acatggctta | 1200 |
| tcagcaggtt | catgcaaata | ttgaaaactc | ttggaatgag | gaagaagttt | ggagaattga | 1260 |
| aatgtatatc | tcctttggca | taatgagcct | tggcttactt | tccctcctgg | cagtcacttc | 1320 |
| tatcccttca | gtgagcaatg | ctttaaactg | gagagaattc | agttttattc | agtctacact | 1380 |
| tggatatgtc | gctctgctca | taagtacttt | ccatgtttta | atttatggat | ggaaacgagc | 1440 |
| ttttgaggaa | gagtactaca | gattttatac | accaccaaac | tttgttcttg | ctcttgtttt | 1500 |
| gccctcaatt | gtaattctgg | atcttttgca | gctttgcaga | tacccagact | gagctggaac | 1560 |
| tggaatttgt | cttcctattg | actctacttc | tttaaaagcg | gctgcccatt | acattcctca | 1620 |
| gctgtccttg | cagttaggtg | tacatgtgac | tgagtgttgg | ccagtgagat | gaagtctcct | 1680 |
| caaaggaagg | cagcatgtgt | ccttttcat | ccttcatct | tgctgctggg | attgtggata | 1740 |
| taacaggagc | cctggcagct | gtctccagag | gatcaaagcc | acacccaaag | agtaaggcag | 1800 |
| attagagacc | agaaagacct | tgactacttc | cctacttcca | ctgcttttc | ctgcatttaa | 1860 |
| gccattgtaa | atctgggtgt | gttacatgaa | gtgaaaatta | attctttctg | cccttcagtt | 1920 |
| ctttatcctg | ataccatta | acactgtctg | aattaactag | actgcaataa | ttctttcttt | 1980 |
| tgaaagcttt | taaaggataa | tgtgcaattc | acattaaaat | tgattttcca | ttgtcaatta | 2040 |
| gttatactca | ttttcctgcc | ttgatctttc | attagatatt | ttgtatctgc | ttggaatata | 2100 |
| ttatcttctt | tttaactgtg | taattggtaa | ttactaaaac | tctgtaatct | ccaaaatatt | 2160 |
| gctatcaaat | tacacaccat | gttttctatc | attctcatag | atctgcctta | taaacattta | 2220 |
| aataaaaagt | actattta | | | | | 2238 |

<210> SEQ ID NO 28
<211> LENGTH: 1561
<212> TYPE: DNA
<213> ORGANISM: Homo sapiens

<400> SEQUENCE: 28

| | | | | | |
|---|---|---|---|---|---|
| gatccagctt | gggtaggcgg | ggaagcagct | ggagtgcgac | cgccgcggca | gccaccctgc | 60 |
| aaccgccagt | cggagagagc | taagggcaag | tcctgaggtt | gggcccagga | gaaagaaggc | 120 |
| aaggagacat | tgtcccaggt | aggatgtgtc | ccaggatatt | cttggtgatc | ttggaagtgt | 180 |

-continued

```
ccgtatcatg gaatcaatct ctatgatggg aagccctaag agccttagtg aaacttgttt      240
acctaatggc ataaatggta tcaaagatgc aaggaaggtc actgtaggtg tgattggaag      300
tggagatttt gccaaatcct tgaccattcg acttattaga tgcggctatc atgtggtcat      360
aggaagtaga atcctaagt ttgcttctga atttttcct catgtggtag atgtcactca        420
tcatgaagat gctctcacaa aaacaaatat aatatttgtt gctatacaca gagaacatta      480
tacctccctg tgggacctga cacatctgct tgtgggtaaa atcctgattg atgtgagcaa      540
taacatgagg ataaaccagt acccagaatc caatgctgaa tatttggctt cattattccc      600
agattctttg attgtcaaag gatttaatgt tgtctcagct tgggcacttc agttaggacc      660
taaggatgcc agccggcagg tttatatatg cagcaacaat attcaagcgc gacaacaggt      720
tattgaactt gcccgccagt tgaatttcat tcccattgac ttgggatcct tatcatcagc      780
cagagagatt gaaaatttac ccctacgact ctttactctc tggagagggc cagtggtggt      840
agctataagc ttggccacat ttttttttcct ttattccttt gtcagagatg tgattcatcc     900
atatgctaga aaccaacaga gtgacttta caaaattcct atagagattg tgaataaaac       960
cttacctata gttgccatta ctttgctctc cctagtatac ctcgcaggtc ttctggcagc     1020
tgcttatcaa ctttattacg gcaccaagta taggagattt ccaccttggt tggaaacctg     1080
gttacagtgt agaaaacagc ttggattact aagtttttc ttcgctatgg tccatgttgc      1140
ctacagcctc tgcttaccga tgagaaggtc agagagatat ttgtttctca acatggctta    1200
tcagcaggtt catgcaaata ttgaaaactc ttggaatgag gaagaagttt ggagaattga    1260
aatgtatatc tcctttggca taatgagcct tggcttactt tccctcctgg cagtcacttc    1320
tatcccttca gtgagcaatg ctttaaactg gagagaattc agttttattc agtctacact    1380
tggatatgtc gctctgctca taagtacttt ccatgtttta atttatggat ggaaacgagc    1440
ttttgaggaa gagtactaca gattttatac accaccaaac tttgttcttg ctcttgtttt    1500
gccctcaatt gtaattctgg atcttttgca gctttgcaga tacccagact gagctggaac    1560
t                                                                     1561
```

<210> SEQ ID NO 29
<211> LENGTH: 454
<212> TYPE: PRT
<213> ORGANISM: Homo sapiens

<400> SEQUENCE: 29

```
Met Glu Ser Ile Ser Met Met Gly Ser Pro Lys Ser Leu Ser Glu Thr
  1               5                  10                  15

Cys Leu Pro Asn Gly Ile Asn Gly Ile Lys Asp Ala Arg Lys Val Thr
             20                  25                  30

Val Gly Val Ile Gly Ser Gly Asp Phe Ala Lys Ser Leu Thr Ile Arg
         35                  40                  45

Leu Ile Arg Cys Gly Tyr His Val Val Ile Gly Ser Arg Asn Pro Lys
     50                  55                  60

Phe Ala Ser Glu Phe Phe Pro His Val Val Asp Val Thr His His Glu
 65                  70                  75                  80

Asp Ala Leu Thr Lys Thr Asn Ile Ile Phe Val Ala Ile His Arg Glu
                 85                  90                  95

His Tyr Thr Ser Leu Trp Asp Leu Arg His Leu Leu Val Gly Lys Ile
            100                 105                 110

Leu Ile Asp Val Ser Asn Asn Met Arg Ile Asn Gln Tyr Pro Glu Ser
        115                 120                 125
```

-continued

```
Asn Ala Glu Tyr Leu Ala Ser Leu Phe Pro Asp Ser Leu Ile Val Lys
    130                 135                 140

Gly Phe Asn Val Val Ser Ala Trp Ala Leu Gln Leu Gly Pro Lys Asp
145                 150                 155                 160

Ala Ser Arg Gln Val Tyr Ile Cys Ser Asn Asn Ile Gln Ala Arg Gln
                165                 170                 175

Gln Val Ile Glu Leu Ala Arg Gln Leu Asn Phe Ile Pro Ile Asp Leu
            180                 185                 190

Gly Ser Leu Ser Ser Ala Arg Glu Ile Glu Asn Leu Pro Leu Arg Leu
        195                 200                 205

Phe Thr Leu Trp Arg Gly Pro Val Val Ala Ile Ser Leu Ala Thr
    210                 215                 220

Phe Phe Phe Leu Tyr Ser Phe Val Arg Asp Val Ile His Pro Tyr Ala
225                 230                 235                 240

Arg Asn Gln Gln Ser Asp Phe Tyr Lys Ile Pro Ile Glu Ile Val Asn
                245                 250                 255

Lys Thr Leu Pro Ile Val Ala Ile Thr Leu Leu Ser Leu Val Tyr Leu
            260                 265                 270

Ala Gly Leu Leu Ala Ala Ala Tyr Gln Leu Tyr Tyr Gly Thr Lys Tyr
        275                 280                 285

Arg Arg Phe Pro Pro Trp Leu Glu Thr Trp Leu Gln Cys Arg Lys Gln
    290                 295                 300

Leu Gly Leu Leu Ser Phe Phe Ala Met Val His Val Ala Tyr Ser
305                 310                 315                 320

Leu Cys Leu Pro Met Arg Arg Ser Glu Arg Tyr Leu Phe Leu Asn Met
                325                 330                 335

Ala Tyr Gln Gln Val His Ala Asn Ile Glu Asn Ser Trp Asn Glu Glu
            340                 345                 350

Glu Val Trp Arg Ile Glu Met Tyr Ile Ser Phe Gly Ile Met Ser Leu
        355                 360                 365

Gly Leu Leu Ser Leu Leu Ala Val Thr Ser Ile Pro Ser Val Ser Asn
    370                 375                 380

Ala Leu Asn Trp Arg Glu Phe Ser Phe Ile Gln Ser Thr Leu Gly Tyr
385                 390                 395                 400

Val Ala Leu Leu Ile Ser Thr Phe His Val Leu Ile Tyr Gly Trp Lys
                405                 410                 415

Arg Ala Phe Glu Glu Glu Tyr Tyr Arg Phe Tyr Thr Pro Pro Asn Phe
            420                 425                 430

Val Leu Ala Leu Val Leu Pro Ser Ile Val Ile Leu Asp Leu Leu Gln
        435                 440                 445

Leu Cys Arg Tyr Pro Asp
    450
```

<210> SEQ ID NO 30
<211> LENGTH: 2102
<212> TYPE: DNA
<213> ORGANISM: Homo sapiens

<400> SEQUENCE: 30

```
ggatccagct tgggtaggcg gggaagcagc tggagtgcga ccgctacggc agccaccctg      60
caaccgccag tcggagagct aagggcaagt cctgaggttg ggcccaggag aaagaaggca     120
aggagacatt gtcccaggat attcttggtg atcttggaag tgtccgtatc atggaatcaa     180
tctctatgat gggaagccct aagagcctta gtgaaacttg tttacctaat ggcataaatg     240
```

-continued

```
gtatcaaaga tgcaaggaag gtcactgtag gtgtgattgg aagtggagat tttgccaaat      300
ccttgaccat tcgacttatt agatgcggct atcatgtggt cataggaagt agaaatccta      360
agtttgcttc tgaatttttt cctcatgtgg tagatgtcac tcatcatgaa gatgctctca      420
caaaaacaaa tataatattt gttgctatac acagagaaca ttatacctcc ctgtgggacc      480
tgagacatct gcttgtgggt aaaatcctga ttgatgtgag caataacatg aggataaacc      540
agtacccaga atccaatgct gaatatttgg cttcattatt cccagattct tgattgtca      600 aaggatttaa tgttgtctca gcttgggcac ttcagttagg acctaaggat gccagccggc      660
aggtttatat atgcagcaac aatattcaag cgcgacaaca ggttattgaa cttgcccgcc      720
agttgaattt cattcccatt gacttgggat cctatcatc agccagagag attgaaaatt      780
taccgctacg actctttact ttctggagag ggccagtggt ggtagctata agcttggcca      840 cattttttt cctttattcc tttgtcagag atgtgattca tccatatgct agaaaccaac      900
agagtgactt ttacaaaatt cctatagaga ttgtgaataa aaccttacct atagttgcca      960
ttactttgct ctccctagta taccttgcag gtcttctggc agctgcttat caactttatt     1020
acggcaccaa gtataggaga tttccacctt ggttggaaac ctggttacag tgtagaaaac     1080
agcttggatt actaagtttt ttcttcgcta tggtccatgt tgcctacagc ctctgcttac     1140
cgatgagaag gtcagagaga tatttgtttc tcaacatggc ttatcagcag gttcatgcaa     1200
atattgaaaa ctcttggaat gaggaagaag tttggagaat tgaaatgtat atctcctttg     1260
gcataatgag ccttggctta ctttccctcc tggcagtcac ttctatccct tcggtgagca     1320
atgctttaaa ctggagagaa ttcagtttta ttcagatctt ttgcagcttt gcagatccc      1380 agactgagct ggaactggaa tttgtcttcc tattgactct acttctttaa aagcggctgc     1440
ccattacatt cctcagctgt ccttgcagtt aggtgtacat gtgactgagt gttggccagt     1500
gagatgaagt ctcctcaaag gaaggcagca tgtgtccttt ttcatccctt catcttgctg     1560
ctgggattgt ggatataaca ggagccctgg cagctgctcc agaggatcaa agccacaccc     1620
aaagagtaag gcagattaga gaccagaaag accttgacta cttccctact tccactgctt     1680
tttcctgcat ttaagccatt gtaaatctgg gtgtgttaca tgaagtgaaa attaattctt     1740
tctgcccttc agttctttat cctgatacca tttaacactg tctgaattaa ctagactgca     1800
ataattcttt cttttgaaag cttttaaagg ataatgtgca attcacatta aaattgattt     1860
tccattgtca attagttata ctcatttttcc tgccttgatc tttcattaga tattttgtat     1920
ctgcttggaa tatattatct tcttttttaac tgtgtaattg gtaattacta aaactctgta     1980
atctccaaaa tattgctatc aaattacaca ccatgtttc tatcattctc atagatctgc     2040
cttataaaca tttaaataaa agtactatt taccaaaaaa aaaaaaaaa aaaaaaaaa      2100 aa                                                                    2102
```

<210> SEQ ID NO 31
<211> LENGTH: 2102
<212> TYPE: DNA
<213> ORGANISM: Homo sapiens

<400> SEQUENCE: 31

```
ggatccagct tgggtaggcg gggaagcagc tggagtgcga ccgctacggc agccaccctg       60
caaccgccag tcggagagct aagggcaagt cctgaggttg ggcccaggag aaagaaggca      120
aggagacatt gtcccaggat attcttggtg atcttggaag tgtccgtatc atggaatcaa      180
```

-continued

```
tctctatgat gggaagccct aagagcctta gtgaaacttg tttacctaat ggcataaatg      240
gtatcaaaga tgcaaggaag gtcactgtag gtgtgattgg aagtggagat tttgccaaat      300
ccttgaccat tcgacttatt agatgcggct atcatgtggt cataggaagt agaaatccta      360
agtttgcttc tgaattttt cctcatgtgg tagatgtcac tcatcatgaa gatgctctca      420
caaaaacaaa tataatattt gttgctatac acagagaaca ttatacctcc ctgtgggacc      480
tgagacatct gcttgtgggt aaaatcctga ttgatgtgag caataacatg aggataaacc      540
agtacccaga tccaatgct gaatatttgg cttcattatt cccagattct ttgattgtca      600
aaggatttaa tgttgtctca gcttgggcac ttcagttagg acctaaggat gccagccggc      660
aggtttatat atgcagcaac aatattcaag cgcgacaaca ggttattgaa cttgcccgcc      720
agttgaattt cattcccatt gacttgggat cctatcatc agccagagag attgaaaatt      780 taccctacg actctttact ttctggagag ggccagtggt ggtagctata agcttggcca      840 cattttttt cctttattcc tttgtcagag atgtgattca tccatatgct agaaaccaac      900
agagtgactt ttacaaaatt cctatagaga ttgtgaataa aaccttacct atagttgcca      960
ttactttgct ctccctagta taccttgcag gtcttctggc agctgcttat caactttatt     1020
acggcaccaa gtataggaga tttccacctt ggttggaaac ctggttacag tgtagaaaac     1080
agcttggatt actaagtttt ttcttcgcta tggtccatgt tgcctacagc ctctgcttac     1140
cgatgagaag gtcagagaga tatttgtttc tcaacatggc ttatcagcag gttcatgcaa     1200
atattgaaaa ctcttggaat gaggaagaag tttggagaat tgaaatgtat atctcctttg     1260
gcataatgag ccttggctta ctttccctcc tggcagtcac ttctatccct tcggtgagca     1320
atgctttaaa ctggagagaa ttcagtttta ttcagatctt ttgcagcttt gcagataccc     1380
agactgagct ggaactggaa tttgtcttcc tattgactct acttctttaa aagcggctgc     1440
ccattacatt cctcagctgt ccttgcagtt aggtgtacat gtgactgagt gttggccagt     1500
gagatgaagt ctcctcaaag gaaggcagca tgtgtccttt ttcatccctt catcttgctg     1560
ctgggattgt ggatataaca ggagccctgg cagctgctcc agaggatcaa agccacaccc     1620
aaagagtaag gcagattaga gaccagaaag accttgacta cttccctact tccactgctt     1680
tttcctgcat ttaagccatt gtaaatctgg gtgtgttaca tgaagtgaaa attaattctt     1740
tctgcccttc agttctttat cctgatacca tttaacactg tctgaattaa ctagactgca     1800
ataattcttt cttttgaaag cttttaaagg ataatgtgca attcacatta aaattgattt     1860
tccattgtca attagttata ctcattttcc tgccttgatc tttcattaga tattttgtat     1920
ctgcttggaa tatattatct tcttttaac tgtgtaattg gtaattacta aaactctgta     1980
atctccaaaa tattgctatc aaattacaca ccatgttttc tatcattctc atagatctgc     2040
cttataaaca tttaaataaa aagtactatt taccaaaaaa aaaaaaaaaa aaaaaaaaa      2100 aa                                                                    2102
```

<210> SEQ ID NO 32
<211> LENGTH: 419
<212> TYPE: PRT
<213> ORGANISM: Homo sapiens

<400> SEQUENCE: 32

Met Glu Ser Ile Ser Met Met Gly Ser Pro Lys Ser Leu Ser Glu Thr
1               5                   10                  15

Cys Leu Pro Asn Gly Ile Asn Gly Ile Lys Asp Ala Arg Lys Val Thr
            20                  25                  30

-continued

Val Gly Val Ile Gly Ser Gly Asp Phe Ala Lys Ser Leu Thr Ile Arg
        35                  40                  45

Leu Ile Arg Cys Gly Tyr His Val Ile Gly Ser Arg Asn Pro Lys
 50                  55                  60

Phe Ala Ser Glu Phe Phe Pro His Val Val Asp Val Thr His His Glu
65                   70                  75                  80

Asp Ala Leu Thr Lys Thr Asn Ile Ile Phe Val Ala Ile His Arg Glu
                85                  90                  95

His Tyr Thr Ser Leu Trp Asp Leu Arg His Leu Leu Val Gly Lys Ile
            100                 105                 110

Leu Ile Asp Val Ser Asn Asn Met Arg Ile Asn Gln Tyr Pro Glu Ser
            115                 120                 125

Asn Ala Glu Tyr Leu Ala Ser Leu Phe Pro Asp Ser Leu Ile Val Lys
        130                 135                 140

Gly Phe Asn Val Val Ser Ala Trp Ala Leu Gln Leu Gly Pro Lys Asp
145                 150                 155                 160

Ala Ser Arg Gln Val Tyr Ile Cys Ser Asn Asn Ile Gln Ala Arg Gln
                165                 170                 175

Gln Val Ile Glu Leu Ala Arg Gln Leu Asn Phe Ile Pro Ile Asp Leu
            180                 185                 190

Gly Ser Leu Ser Ser Ala Arg Glu Ile Glu Asn Leu Pro Leu Arg Leu
        195                 200                 205

Phe Thr Phe Trp Arg Gly Pro Val Val Ala Ile Ser Leu Ala Thr
210                 215                 220

Phe Phe Phe Leu Tyr Ser Phe Val Arg Asp Val Ile His Pro Tyr Ala
225                 230                 235                 240

Arg Asn Gln Gln Ser Asp Phe Tyr Lys Ile Pro Glu Ile Val Asn
                245                 250                 255

Lys Thr Leu Pro Ile Val Ala Ile Thr Leu Leu Ser Leu Val Tyr Leu
            260                 265                 270

Ala Gly Leu Leu Ala Ala Ala Tyr Gln Leu Tyr Tyr Gly Thr Lys Tyr
        275                 280                 285

Arg Arg Phe Pro Pro Trp Leu Glu Thr Trp Leu Gln Cys Arg Lys Gln
290                 295                 300

Leu Gly Leu Leu Ser Phe Phe Ala Met Val His Val Ala Tyr Ser
305                 310                 315                 320

Leu Cys Leu Pro Met Arg Arg Ser Glu Arg Tyr Leu Phe Leu Asn Met
                325                 330                 335

Ala Tyr Gln Gln Val His Ala Asn Ile Glu Asn Ser Trp Asn Glu Glu
            340                 345                 350

Glu Val Trp Arg Ile Glu Met Tyr Ile Ser Phe Gly Ile Met Ser Leu
        355                 360                 365

Gly Leu Leu Ser Leu Leu Ala Val Thr Ser Ile Pro Ser Val Ser Asn
370                 375                 380

Ala Leu Asn Trp Arg Glu Phe Ser Phe Ile Gln Ile Phe Cys Ser Phe
385                 390                 395                 400

Ala Asp Thr Gln Thr Glu Leu Glu Leu Glu Phe Val Phe Leu Leu Thr
                405                 410                 415

Leu Leu Leu

<210> SEQ ID NO 33
<211> LENGTH: 1396
<212> TYPE: DNA

<213> ORGANISM: Homo sapiens

<400> SEQUENCE: 33

```
acagatctat ggagaaaact tgtatagatg cacttcctct tactatgaat tcttcagaaa      60
agcaagagac tgtatgtatt tttggaactg gtgattttgg aagatcactg ggattgaaaa    120
tgctccagtg tggttattct gttgtttttg gaagtcgaaa cccccagaag accaccctac    180
tgcccagtgg tgcagaagtc ttgagctatt cagaagcagc caagaagtct gacatcataa    240
tcatagcaat ccacagagag cattatgatt ttctcacaga attaactgag gttctcaatg    300
gaaaatatt ggtagacatc agcaacaacc tcaaaatcaa tcaatatcca gaatctaatg    360
cagagtacct tgctcatttg gtgccaggag cccacgtggt aaaagcattt aacaccatct    420
cagcctgggc tctccagtca ggagcactgg atgcaagtcg gcaggtgttt gtgtgtggaa    480
atgacagcaa agccaagcaa agagtgatgg atattgttcg taatcttgga cttactccaa    540
tggatcaagg atcactcatg gcagccaaag aaattgaaaa gtaccccctg cagctatttc    600
caatgtggag gttcccctc tatttgtctg ctgtgctgtg tgtcttcttg tttttctatt    660
gtgttataag agacgtaatc taccettatg tttatgaaaa gaaagataat acatttcgta    720
tggctatttc cattccaaat cgtatctttc caataacagc acttacactg cttgctttgg    780
tttacctccc tggtgttatt gctgccattc tacaactgta ccgaggcaca aaataccgtc    840
gattcccaga ctggcttgac cactggatgc tttgccgaaa gcagcttggc ttggtagctc    900
tgggatttgc cttccttcat gtcctctaca cacttgtgat tcctattcga tattatgtac    960
gatggagatt gggaaactta accgttaccc aggcaatacc caagaaggag aatccattta   1020
gcacctcctc agcctggctc agtgattcat atgtggcttt gggaatactt gggttttttc   1080
tgtttgtact cttgggaatc acttctttgc catctgttag caatgcagtc aactggagag   1140
agttccgatt tgtccagtcc aaactgggtt atttgaccct gatcttgtgt acagcccaca   1200
ccctggtgta cggtgggaag agattcctca gcccttcaaa tctcagatgg tatcttcctg   1260
cagcctacgt gttagggctt atcattcctt gcactgtgct ggtgatcaag tttgtcctaa   1320
tcatgccatg tgtagacaac acccttacaa ggatccgcca gggctgggaa aggaactcaa   1380
aacactagct cgaggt                                                    1396
```

<210> SEQ ID NO 34
<211> LENGTH: 461
<212> TYPE: PRT
<213> ORGANISM: Homo sapiens

<400> SEQUENCE: 34

```
Met Glu Lys Thr Cys Ile Asp Ala Leu Pro Leu Thr Met Asn Ser Ser
  1               5                  10                  15

Glu Lys Gln Glu Thr Val Cys Ile Phe Gly Thr Gly Asp Phe Gly Arg
             20                  25                  30

Ser Leu Gly Leu Lys Met Leu Gln Cys Gly Tyr Ser Val Val Phe Gly
         35                  40                  45

Ser Arg Asn Pro Gln Lys Thr Thr Leu Leu Pro Ser Gly Ala Glu Val
     50                  55                  60

Leu Ser Tyr Ser Glu Ala Ala Lys Lys Ser Asp Ile Ile Ile Ala
 65                  70                  75                  80

Ile His Arg Glu His Tyr Asp Phe Leu Thr Glu Leu Thr Glu Val Leu
                 85                  90                  95

Asn Gly Lys Ile Leu Val Asp Ile Ser Asn Asn Leu Lys Ile Asn Gln
```

```
                    100                 105                 110
Tyr Pro Glu Ser Asn Ala Glu Tyr Leu Ala Thr His Leu Val Pro Gly
            115                 120                 125

Ala His Val Val Lys Ala Phe Asn Thr Ile Ser Ala Trp Ala Leu Gln
        130                 135                 140

Ser Gly Ala Leu Asp Ala Ser Arg Gln Val Phe Val Cys Gly Asn Asp
145                 150                 155                 160

Ser Lys Ala Lys Gln Arg Val Met Asp Ile Val Arg Asn Leu Gly Leu
                165                 170                 175

Thr Pro Met Asp Gln Gly Ser Leu Met Ala Ala Lys Glu Ile Glu Lys
            180                 185                 190

Tyr Pro Leu Gln Leu Phe Pro Met Trp Arg Phe Pro Phe Tyr Leu Ser
        195                 200                 205

Ala Val Leu Cys Val Phe Leu Phe Phe Tyr Cys Val Ile Arg Asp Val
210                 215                 220

Ile Tyr Pro Tyr Val Tyr Glu Lys Lys Asp Asn Thr Phe Arg Met Ala
225                 230                 235                 240

Ile Ser Ile Pro Asn Arg Ile Phe Pro Ile Thr Ala Leu Thr Leu Leu
                245                 250                 255

Ala Leu Val Tyr Leu Pro Gly Val Ile Ala Ala Ile Leu Gln Leu Tyr
            260                 265                 270

Arg Gly Thr Lys Tyr Arg Arg Phe Pro Asp Trp Leu Asp His Trp Met
        275                 280                 285

Leu Cys Arg Lys Gln Leu Gly Leu Val Ala Leu Gly Phe Ala Phe Leu
290                 295                 300

His Val Leu Tyr Thr Leu Val Ile Pro Ile Arg Tyr Tyr Val Arg Trp
305                 310                 315                 320

Arg Leu Gly Asn Leu Thr Val Thr Gln Ala Ile Pro Leu Lys Lys Glu
                325                 330                 335

Asn Pro Phe Ser Thr Ser Ser Ala Trp Leu Ser Asp Ser Tyr Val Ala
            340                 345                 350

Leu Gly Ile Leu Gly Phe Phe Leu Phe Val Leu Leu Gly Ile Thr Ser
        355                 360                 365

Leu Pro Ser Val Ser Asn Ala Val Asn Trp Arg Glu Phe Arg Phe Val
370                 375                 380

Gln Ser Lys Leu Gly Tyr Leu Thr Leu Ile Leu Cys Thr Ala His Thr
385                 390                 395                 400

Leu Val Tyr Gly Gly Lys Arg Phe Leu Ser Pro Ser Asn Leu Arg Trp
                405                 410                 415

Tyr Leu Pro Ala Ala Tyr Val Leu Gly Leu Ile Ile Pro Cys Thr Val
            420                 425                 430

Leu Val Ile Lys Phe Val Leu Ile Met Pro Cys Val Asp Asn Thr Leu
        435                 440                 445

Thr Arg Ile Arg Gln Gly Trp Glu Arg Asn Ser Lys His
450                 455                 460

<210> SEQ ID NO 35
<211> LENGTH: 3910
<212> TYPE: DNA
<213> ORGANISM: Homo sapiens

<400> SEQUENCE: 35
acccttcgcc gcggaccttc agctgccgcg gtcgctccga gcggcgggcc gcagaggttc      60
aagcgattct cctgcttcag cctccggagt agctgggatt acaggcacgt gccaacacac    120
```

-continued

```
ccagccacca aaatgccaga agagatggac aagccactga tcagcctcca cctggtggac    180
agcgatagta gccttgccaa ggtccccgat gaggccccca aagtgggcat cctgggtagc    240
ggggactttg cccgctccct ggccacacgc ctggtgggct ctggcttcaa agtggtggtg    300
gggagccgca accccaaacg cacagccagg ctgtatccct cagcggccca agtgactttc    360
caagaggagg cagtgagctc cccggaggtc atctttgtgg ctgtgttccg ggagcactac    420
tcttcactgt gcagtctcag tgaccagctg gcgggcaaga tcctggtgga tgtgagcaac    480
cctacagagc aagagcacct tcagcatcgt gagtccaatg ctgagtacct ggcctccctc    540
ttccccactt gcacagtggt caaggccttc aatgtcatct ctgcctggac cctgcaggct    600
ggcccaaggg atggtaacag gcaggtgccc atctgcggtg accagccaga agccaagcgt    660
gctgtctcgg agatggcgct cgccatgggc ttcatgcccg tggacatggg atccctggcg    720
tcagcctggg aggtggaggc catgcccctg cgcctcctcc cggcctggaa ggtgcccacc    780
ctgctggccc tggggctctt cgtctgcttc tatgcctaca acttcgtccg ggacgttctg    840
cagccctatg tgcaggaaag ccagaacaag ttcttcaagc tgcccgtgtc cgtggtcaac    900
accacactgc cgtgcgtggc ctacgtgctg ctgtcactcg tgtacttgcc cggcgtgctg    960
gcggctgccc tgcagctgcg gcgcggcacc aagtaccagc gcttccccga ctggctggac    1020
cactggctac agcaccgcaa gcagatcggg ctgctcagct tcttctgcgc cgccctgcac    1080
gccctctaca gcttctgctt gccgctgcgc cgcgcccacc gctacgacct ggtcaacctg    1140
gcagtcaagc aggtcttggc caacaagagc cacctctggg tggaggagga ggtctggcgg    1200
atggagatct acctctcccct gggagtgctg gccctcggca cgttgtccct gctggccgtg    1260
acctcactgc cgtccattgc aaactcgctc aactggaggg agttcagctt cgttcagtcc    1320
tcactgggct tgtgggccct cgtgctgagc acactgcaca cgctcaccta cggctggacc    1380
cgcgccttcg aggagagccg ctacaagttc tacctgcctc ccaccttcac gctcacgctg    1440
ctggtgccct gcgtcgtcat cctggccaaa gccctgtttc tcctgccctg catcagccgc    1500
agactcgcca ggatccggag aggctgggag agggagagca ccatcaagtt cacgctgccc    1560
acagaccacg ccctggccga aagacgagc cacgtatgag gtgcctgccc tgggctctgg    1620
accccgggca cacgagggac ggtgccctga gcccgttagg ttttcttttc ttggtggtgc    1680
aaagtggtat aactgtgtgc aaataggagg tttgaggtcc aaattcctgg gactcaaatg    1740
tatgcagtac tattcagaat gatatacaca catatgtgta tatgtattta catatattcc    1800
acatatataa caggatttgc aattatacat agctagctaa aaagttgggt ctctgagatt    1860
tcaacttgta gatttaaaaa caagtgccgt acgttaagag aagagcagat catgctattg    1920
tgacatttgc agagatatac acacactttt tgtacagaag aggcttgtgc tgtggtgggt    1980
tcgatttatc cctgcccacc ccatccccac aacttcccctt tgctacttc cccaaggctc    2040 ttgcagagct agggctctga aggggaggga aggcaacggc tctgcccaga gccatccctg    2100
gagcatgtga gcagcggctg gtctcttccc tccacctggg gcagcagcag gaggcctggg    2160
ggggaggaaa atcaggcagt cggcctggag tctgtgcctg gtcctttgcc cggtggtggg    2220
aggatggagg gattgggctg aagctgctcc acctcatcct tgctgagtgg gggagacatt    2280
ttccctgaaa gtcagaagtc accatagagc ctgcaaatgg atcctcctgt gagagtgacg    2340
tcacctcctt tccagagcca ttagtgagcc tggcttggga acaagtgtaa tttccttccc    2400
tcctttaacc tggcgatgag cgtcctttaa accactgtgc cttctcaccc tttccatctt    2460
```

```
cagtttgaac gactcccagg aaggcctaga gcagacccct tagaaatcag cccaaggggg    2520
agagcaagag aaaacactct agggagtaaa gctccccggg cgtcagagtt gagccctgcc    2580
tgggctgaag gactgtcttc acgaagtcag tcctgaggaa aaatattggg gactccaaat    2640
gtcctctggc agaggaccca gaaaaccaca ctggctccaa cttcctcctc atggggcatt    2700
acacttcaaa acagtgggga gcaacttttc caccaaagct acaaacctaa aatgctgctg    2760
ccccaaagca caagagggaa gagcaccgcc ggggccacag gacgtctgtc ctccagtcac    2820
aggccatcct tgctgctccc tactgactct agcttacttc ccctgtgaag aaacaggtgt    2880
tctcggctga gcccccaacc ctctgcagaa ccaggttgat ctgccacaga aaaagcatct    2940
ttgaagacaa agagggtgag gtcttcatga gtctcctggg cccaaagcca tcttctgatg    3000
gaaggaagag agtagggcca gtgaaggctg cccagagaga atgtcacaga tgaggctgcc    3060
cctgccccct ccccgccagg gaggtttcat gagctcatgt ctatgcagca cataagggtt    3120
cttcagtgaa aagcaggaga agagcccact gcaaggatag ctcattaggc acatgaccga    3180
tgcagggaag gccatgccgg ggaagctctt cctgcaggta ttttccatct gctgtgccaa    3240
ggctgagcgg cagaaacttg tctcataaat tggcactgat ggagcatcag ctgtggccca    3300
cagagagcct tgctgagaag ggggcaggta agcagagat tttagcattg ccttggcata    3360
acaagggccc atcgattccc tactaatgag aggcagggag agcatgggca atggagaccc    3420
accaatgatc cccaaccccg gtgggtactg gctgcctgcc ctgggccagg gaatggctcc    3480
ttataccaaa gatgctggca catagcagaa cccagtgcac gtcctcccct tcccacccac    3540
ctctggctga aggtgctcaa gagggaagca attataaggt gggtggcagg agggaacagg    3600
tgccacctgc tggacaatca cacgaaaggc aggcgggctg tgtactgggc cctgactgtg    3660
cgtccactgc tgtcttccct acctcaccag gctactggca gcagcatccc gagagcacat    3720
catctccaca gcctggtaaa ttccatgtgc ctctgggtac aaaagtgcct caacgacatg    3780
ctctggaaat cccaaatgcc acagtctgag gttgatatct aaaatctatg ccttcaaaag    3840
agtctctgtt ttttttttt aacctggtag acggtataaa agcagtgcaa ataaacacct    3900
aaccttctgc                                                           3910
```

<210> SEQ ID NO 36
<211> LENGTH: 488
<212> TYPE: PRT
<213> ORGANISM: Homo sapiens

<400> SEQUENCE: 36

```
Met Pro Glu Glu Met Asp Lys Pro Leu Ile Ser Leu His Leu Val Asp
 1               5                  10                  15

Ser Asp Ser Ser Leu Ala Lys Val Pro Asp Glu Ala Pro Lys Val Gly
                20                  25                  30

Ile Leu Gly Ser Gly Asp Phe Ala Arg Ser Leu Ala Thr Arg Leu Val
            35                  40                  45

Gly Ser Gly Phe Lys Val Val Val Gly Ser Arg Asn Pro Lys Arg Thr
        50                  55                  60

Ala Arg Leu Tyr Pro Ser Ala Ala Gln Val Thr Phe Gln Glu Glu Ala
65                  70                  75                  80

Val Ser Ser Pro Glu Val Ile Phe Val Ala Val Phe Arg Glu His Tyr
                85                  90                  95

Ser Ser Leu Cys Ser Leu Ser Asp Gln Leu Ala Gly Lys Ile Leu Val
                100                 105                 110
```

-continued

```
Asp Val Ser Asn Pro Thr Glu Gln Glu His Leu Gln His Arg Glu Ser
        115                 120                 125
Asn Ala Glu Tyr Leu Ala Ser Leu Phe Pro Thr Cys Thr Val Val Lys
    130                 135                 140
Ala Phe Asn Val Ile Ser Ala Trp Thr Leu Gln Ala Gly Pro Arg Asp
145                 150                 155                 160
Gly Asn Arg Gln Val Pro Ile Cys Gly Asp Gln Pro Glu Ala Lys Arg
                165                 170                 175
Ala Val Ser Glu Met Ala Leu Ala Met Gly Phe Met Pro Val Asp Met
            180                 185                 190
Gly Ser Leu Ala Ser Ala Trp Glu Val Glu Ala Met Pro Leu Arg Leu
        195                 200                 205
Leu Pro Ala Trp Lys Val Pro Thr Leu Leu Ala Leu Gly Leu Phe Val
    210                 215                 220
Cys Phe Tyr Ala Tyr Asn Phe Val Arg Asp Val Leu Gln Pro Tyr Val
225                 230                 235                 240
Gln Glu Ser Gln Asn Lys Phe Lys Leu Pro Val Ser Val Val Asn
                245                 250                 255
Thr Thr Leu Pro Cys Val Ala Tyr Val Leu Leu Ser Leu Val Tyr Leu
            260                 265                 270
Pro Gly Val Leu Ala Ala Leu Gln Leu Arg Arg Gly Thr Lys Tyr
        275                 280                 285
Gln Arg Phe Pro Asp Trp Leu Asp His Trp Leu Gln His Arg Lys Gln
    290                 295                 300
Ile Gly Leu Leu Ser Phe Cys Ala Ala Leu His Ala Leu Tyr Ser
305                 310                 315                 320
Phe Cys Leu Pro Leu Arg Arg Ala His Arg Tyr Asp Leu Val Asn Leu
                325                 330                 335
Ala Val Lys Gln Val Leu Ala Asn Lys Ser His Leu Trp Val Glu Glu
            340                 345                 350
Glu Val Trp Arg Met Glu Ile Tyr Leu Ser Leu Gly Val Leu Ala Leu
        355                 360                 365
Gly Thr Leu Ser Leu Leu Ala Val Thr Ser Leu Pro Ser Ile Ala Asn
    370                 375                 380
Ser Leu Asn Trp Arg Glu Phe Ser Phe Val Gln Ser Ser Leu Gly Phe
385                 390                 395                 400
Val Ala Leu Val Leu Ser Thr Leu His Thr Leu Thr Tyr Gly Trp Thr
                405                 410                 415
Arg Ala Phe Glu Glu Ser Arg Tyr Lys Phe Tyr Leu Pro Pro Thr Phe
            420                 425                 430
Thr Leu Thr Leu Leu Val Pro Cys Val Val Ile Leu Ala Lys Ala Leu
        435                 440                 445
Phe Leu Leu Pro Cys Ile Ser Arg Arg Leu Ala Arg Ile Arg Arg Gly
    450                 455                 460
Trp Glu Arg Glu Ser Thr Ile Lys Phe Thr Leu Pro Thr Asp His Ala
465                 470                 475                 480
Leu Ala Glu Lys Thr Ser His Val
                485

<210> SEQ ID NO 37
<211> LENGTH: 339
<212> TYPE: PRT
<213> ORGANISM: Homo sapiens

<400> SEQUENCE: 37
```

Met Glu Ser Arg Lys Asp Ile Thr Asn Gln Glu Leu Trp Lys Met
1               5                  10                 15

Lys Pro Arg Arg Asn Leu Glu Glu Asp Asp Tyr Leu His Lys Asp Thr
            20                  25                 30

Gly Glu Thr Ser Met Leu Lys Arg Pro Val Leu Leu His Leu His Gln
        35                  40                  45

Thr Ala His Ala Asp Glu Phe Asp Cys Pro Ser Glu Leu Gln His Thr
50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Arg Glu Val Ile His
                85                  90                  95

Pro Leu Ala Thr Ser His Gln Gln Tyr Phe Tyr Lys Ile Pro Ile Leu
                100                 105                 110

Val Ile Asn Lys Val Leu Pro Met Val Ser Ile Thr Leu Leu Ala Leu
            115                 120                 125

Val Tyr Leu Pro Gly Val Ile Ala Ala Ile Val Gln Leu His Asn Gly
    130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
        195                 200                 205

Ile Glu His Asp Val Trp Arg Met Glu Ile Tyr Val Ser Leu Gly Ile
    210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Ser Lys
                245                 250                 255

Leu Gly Ile Val Ser Leu Leu Leu Gly Thr Ile His Ala Leu Ile Phe
            260                 265                 270

Ala Trp Asn Lys Trp Ile Asp Ile Lys Gln Phe Val Trp Tyr Thr Pro
        275                 280                 285

Pro Thr Phe Met Ile Ala Val Phe Leu Pro Ile Val Val Leu Ile Phe
    290                 295                 300

Lys Ser Ile Leu Phe Leu Pro Cys Leu Arg Lys Lys Ile Leu Lys Ile
305                 310                 315                 320

Arg His Gly Trp Glu Asp Val Thr Lys Ile Asn Lys Thr Glu Ile Cys
                325                 330                 335

Ser Gln Leu

<210> SEQ ID NO 38
<211> LENGTH: 488
<212> TYPE: PRT
<213> ORGANISM: Homo sapiens

<400> SEQUENCE: 38

Met Pro Glu Glu Met Asp Lys Pro Leu Ile Ser Leu His Leu Val Asp
1               5                   10                  15

Ser Asp Ser Ser Leu Ala Lys Val Pro Asp Glu Ala Pro Lys Val Gly
            20                  25                  30

-continued

```
Ile Leu Gly Ser Gly Asp Phe Ala Arg Ser Leu Ala Thr Arg Leu Val
         35                  40                  45
Gly Ser Gly Phe Lys Val Val Gly Ser Arg Asn Pro Lys Arg Thr
 50                  55                  60
Ala Arg Leu Tyr Pro Ser Ala Ala Gln Val Thr Phe Gln Glu Glu Ala
 65                  70                  75                  80
Val Ser Ser Pro Glu Val Ile Phe Val Ala Val Phe Arg Glu His Tyr
                 85                  90                  95
Ser Ser Leu Cys Ser Leu Ser Asp Gln Leu Ala Gly Lys Ile Leu Val
                100                 105                 110
Asp Val Ser Asn Pro Thr Glu Gln Glu His Leu Gln His Arg Glu Ser
            115                 120                 125
Asn Ala Glu Tyr Leu Ala Ser Leu Phe Pro Thr Cys Thr Val Val Lys
        130                 135                 140
Ala Phe Asn Val Ile Ser Ala Trp Thr Leu Gln Ala Gly Pro Arg Asp
145                 150                 155                 160
Gly Asn Arg Gln Val Pro Ile Cys Gly Asp Gln Pro Glu Ala Lys Arg
                165                 170                 175
Ala Val Ser Glu Met Ala Leu Ala Met Gly Phe Met Pro Val Asp Met
            180                 185                 190
Gly Ser Leu Ala Ser Ala Trp Glu Val Glu Ala Met Pro Leu Arg Leu
        195                 200                 205
Leu Pro Ala Trp Lys Val Pro Thr Leu Leu Ala Leu Gly Leu Phe Val
210                 215                 220
Cys Phe Tyr Ala Tyr Asn Phe Val Arg Asp Val Leu Gln Pro Tyr Val
225                 230                 235                 240
Gln Glu Ser Gln Asn Lys Phe Phe Lys Leu Pro Val Ser Val Val Asn
                245                 250                 255
Thr Thr Leu Pro Cys Val Ala Tyr Val Leu Leu Ser Leu Val Tyr Leu
            260                 265                 270
Pro Gly Val Leu Ala Ala Ala Leu Gln Leu Arg Arg Gly Thr Lys Tyr
        275                 280                 285
Gln Arg Phe Pro Asp Trp Leu Asp His Trp Leu Gln His Arg Lys Gln
290                 295                 300
Ile Gly Leu Leu Ser Phe Phe Cys Ala Ala Leu His Ala Leu Tyr Ser
305                 310                 315                 320
Phe Cys Leu Pro Leu Arg Arg Ala His Arg Tyr Asp Leu Val Asn Leu
                325                 330                 335
Ala Val Lys Gln Val Leu Ala Asn Lys Ser His Leu Trp Val Glu Glu
            340                 345                 350
Glu Val Trp Arg Met Glu Ile Tyr Leu Ser Leu Gly Val Leu Ala Leu
        355                 360                 365
Gly Thr Leu Ser Leu Leu Ala Val Thr Ser Leu Pro Ser Ile Ala Asn
370                 375                 380
Ser Leu Asn Trp Arg Glu Phe Ser Phe Val Gln Ser Ser Leu Gly Phe
385                 390                 395                 400
Val Ala Leu Val Leu Ser Thr Leu His Thr Leu Thr Tyr Gly Trp Thr
                405                 410                 415
Arg Ala Phe Glu Glu Ser Arg Tyr Lys Phe Tyr Leu Pro Pro Thr Phe
            420                 425                 430
Thr Leu Thr Leu Leu Val Pro Cys Val Val Ile Leu Ala Lys Ala Leu
        435                 440                 445
```

```
Phe Leu Leu Pro Cys Ile Ser Arg Arg Leu Ala Arg Ile Arg Arg Gly
    450                 455                 460

Trp Glu Arg Glu Ser Thr Ile Lys Phe Thr Leu Pro Thr Asp His Ala
465                 470                 475                 480

Leu Ala Glu Lys Thr Ser His Val
                485

<210> SEQ ID NO 39
<211> LENGTH: 283
<212> TYPE: PRT
<213> ORGANISM: Homo sapiens

<400> SEQUENCE: 39

Met Glu Lys Thr Cys Ile Asp Ala Leu Pro Leu Thr Met Asn Ser Ser
  1               5                  10                  15

Glu Lys Gln Glu Thr Val Cys Ile Phe Gly Thr Gly Asp Phe Gly Arg
             20                  25                  30

Ser Leu Gly Leu Lys Met Leu Gln Cys Gly Tyr Ser Val Phe Gly
         35                  40                  45

Ser Arg Asn Pro Gln Lys Thr Thr Leu Leu Pro Ser Gly Ala Glu Val
 50                  55                  60

Leu Ser Tyr Ser Glu Ala Ala Lys Lys Ser Asp Ile Ile Ile Ala
65                  70                  75                  80

Ile His Arg Glu His Tyr Asp Phe Leu Thr Glu Leu Thr Glu Val Leu
                 85                  90                  95

Asn Gly Lys Ile Leu Val Asp Ile Ser Asn Asn Leu Lys Ile Asn Gln
            100                 105                 110

Tyr Pro Glu Ser Asn Ala Glu Tyr Leu Ala His Leu Val Pro Gly Ala
        115                 120                 125

His Val Val Lys Ala Phe Asn Thr Ile Ser Ala Trp Ala Leu Gln Ser
    130                 135                 140

Gly Ala Leu Asp Ala Ser Arg Gln Val Phe Val Cys Gly Asn Asp Ser
145                 150                 155                 160

Lys Ala Lys Gln Arg Val Met Asp Ile Val Arg Asn Leu Gly Leu Thr
                165                 170                 175

Pro Met Asp Gln Gly Ser Leu Met Ala Ala Lys Glu Ile Glu Lys Tyr
            180                 185                 190

Pro Leu Gln Leu Phe Pro Met Trp Arg Phe Pro Phe Tyr Leu Ser Ala
        195                 200                 205

Val Leu Cys Val Phe Leu Phe Phe Tyr Cys Val Ile Arg Asp Val Ile
    210                 215                 220

Tyr Pro Tyr Val Tyr Glu Lys Lys Asp Asn Thr Phe Arg Met Ala Ile
225                 230                 235                 240

Ser Ile Pro Asn Arg Ile Phe Pro Ile Thr Ala Pro Tyr Thr Ala Cys
                245                 250                 255

Phe Gly Leu Pro Pro Trp Cys Tyr Cys His Ser Thr Thr Val Pro
            260                 265                 270

Arg His Lys Ile Pro Ser Ile Pro Arg Leu Ala
        275                 280

<210> SEQ ID NO 40
<211> LENGTH: 1461
<212> TYPE: DNA
<213> ORGANISM: Homo sapiens

<400> SEQUENCE: 40
```

```
agcggcggct cctgcagcgg tggtcggctg ttgggtgtgg agtttcccag cgcccctcgg      60
gtccgaccct ttgagcgttc tgctccggcg ccagcctacc tcgctcctcg gcgccatgac     120
cacaaccacc accttcaagg gagtcgaccc caacagcagg aatagctccc gagttttgcg     180
gcctccaggt ggtggatcca attttcatt aggttttgat gaaccaacag aacaacctgt     240
gaggaagaac aaaatggcct ctaatatctt tgggacacct gaagaaaatc aagcttcttg     300
ggccaagtca gcaggtgcca agtctagtgg tggcagggaa gacttggagt catctggact     360
gcagagaagg aactcctctg aagcaagctc cggagacttc ttagatctga agggagaagg     420
tgatattcat gaaaatgtgg acacagactt gccaggcagc ctggggcaga gtgaagagaa     480
gcccgtgcct gctgcgcctg tgcccagccc ggtggccccg ccccagtgc catccagaag      540
aaatccccct ggcggcaagt ccagcctcgt cttgggttag ctctgactgt cctgaacgct     600
gtcgttctgt ctgtttcctc catgcttgtg aactgcacaa cttgagcctg actgtacatc     660
tcttggattt gtttcattaa aagaagcac tttatgtact gctgtctttt ttttttttct      720
tttgaagaac aggtttctct ctgtccttga ctcttgggtc tgtgggccat ggcatgagtg     780
ttttctagta gtagattgga gggaaagctt tgtgacactt agtactgtgt ttttaagaag     840
aaataatttg gttccagatg tgttagagga tcttttgtac tgaggttttt aacactttac     900
ttgggtttac caagcctcaa ctggacagac cataaacagt ccacaggcac cgttcctgcc     960
aggccccaac ccacagggag tctctccgca gagccttctt ggtgttgccc taacttgcca    1020
gtggcctttg ctcagagcct cctcctgtga catgtgaaca atgaagaggc ctgcgcctcc    1080
tgccttgccg cctgcaaagc aaagaaactg ccttttattt tttaaccta aaaagtagcc     1140
agatagtaac aagactggct ggctgatgag caaagccttt gctctcacgc agaggaaggc    1200
ttggatgtac aatgaaactg cctggaacta aaagcagtga agcaagggag gcaatcacac    1260
tgaagcgggt cttcctccag gaacggggtc ccacaggcgt gttgttttaa ataacctgat    1320
gctgtgtgca tgatgctggt gcttgaccat gaaaggaaag tctcatcctt aaaatgtgtt    1380
gtacttcaca atcctggact gttgcttcaa gtaaacaata tccacattct aaaaaaaaaa    1440
aaaaaaaaaa aaaaaaaaa a                                               1461

<210> SEQ ID NO 41
<211> LENGTH: 154
<212> TYPE: PRT
<213> ORGANISM: Homo sapiens

<400> SEQUENCE: 41

Met Thr Thr Thr Thr Thr Phe Lys Gly Val Asp Pro Asn Ser Arg Asn
 1               5                  10                  15

Ser Ser Arg Val Leu Arg Pro Pro Gly Gly Ser Asn Phe Ser Leu
                20                  25                  30

Gly Phe Asp Glu Pro Thr Glu Gln Pro Val Arg Lys Asn Lys Met Ala
             35                  40                  45

Ser Asn Ile Phe Gly Thr Pro Glu Glu Asn Gln Ala Ser Trp Ala Lys
         50                  55                  60

Ser Ala Gly Ala Lys Ser Ser Gly Gly Arg Glu Asp Leu Glu Ser Ser
65                  70                  75                  80

Gly Leu Gln Arg Arg Asn Ser Ser Glu Ala Ser Ser Gly Asp Phe Leu
                85                  90                  95

Asp Leu Lys Gly Glu Gly Asp Ile His Glu Asn Val Asp Thr Asp Leu
            100                 105                 110
```

```
Pro Gly Ser Leu Gly Gln Ser Glu Glu Lys Pro Val Pro Ala Ala Pro
        115                 120                 125

Val Pro Ser Pro Val Ala Pro Ala Pro Val Pro Ser Arg Arg Asn Pro
    130                 135                 140

Pro Gly Gly Lys Ser Ser Leu Val Leu Gly
145                 150

<210> SEQ ID NO 42
<211> LENGTH: 50
<212> TYPE: DNA
<213> ORGANISM: Homo sapiens

<400> SEQUENCE: 42
tgaaaaccct ataaaggcgt cgatcggccg gacaggcggc agcggcggct          50

<210> SEQ ID NO 43
<211> LENGTH: 28
<212> TYPE: DNA
<213> ORGANISM: Homo sapiens

<400> SEQUENCE: 43
catgaccaca accaccacct tcaaggga                                  28

<210> SEQ ID NO 44
<211> LENGTH: 28
<212> TYPE: DNA
<213> ORGANISM: Homo sapiens

<400> SEQUENCE: 44
tgccattatt tgcagagttt tgcggcct                                  28

<210> SEQ ID NO 45
<211> LENGTH: 28
<212> TYPE: DNA
<213> ORGANISM: Homo sapiens

<400> SEQUENCE: 45
aaatcaagct tcttgggcca agtcagca                                  28

<210> SEQ ID NO 46
<211> LENGTH: 28
<212> TYPE: DNA
<213> ORGANISM: Homo sapiens

<400> SEQUENCE: 46
tattttgatt tttaggtgcc aagtctag                                  28

<210> SEQ ID NO 47
<211> LENGTH: 28
<212> TYPE: DNA
<213> ORGANISM: Homo sapiens

<400> SEQUENCE: 47
cttagatctg aaggtcagtg tgacagca                                  28

<210> SEQ ID NO 48
<211> LENGTH: 22
<212> TYPE: DNA
<213> ORGANISM: Homo sapiens

<400> SEQUENCE: 48
tttttctttt tctaggagaa ag                                        22
```

<210> SEQ ID NO 49
<211> LENGTH: 27
<212> TYPE: DNA
<213> ORGANISM: Homo sapiens

<400> SEQUENCE: 49
gtgatattca tggtaagtac ttctgaa                                27

<210> SEQ ID NO 50
<211> LENGTH: 28
<212> TYPE: DNA
<213> ORGANISM: Homo sapiens

<400> SEQUENCE: 50
tccctgtttt catagaaaat gtggacac                               28

<210> SEQ ID NO 51
<211> LENGTH: 3526
<212> TYPE: DNA
<213> ORGANISM: Homo sapiens

<400> SEQUENCE: 51

| | |
|---|---|
| atgaccgacg cgctgttgcc cgcggccccc cagccgctgg agaaggagaa cgacggctac | 60 |
| tttcggaagg gctgtaatcc ccttgcacaa accggccgga gtaaattgca gaatcaaaga | 120 |
| gctgctttga atcagcagat cctgaaagcc gtgcggatga ggaccggagc ggaaaacctt | 180 |
| ctgaaagtgg ccacaaactc aaaggtgcgg gagcaagtgc ggctgagct gagcttcgtc | 240 |
| aactcagacc tgcagatgct caaggaagag ctggaggggc tgaacatctc ggtgggcgtc | 300 |
| tatcagaaca cagaggaggc atttacgatt cccctgattc ctcttggcct gaaggaaacg | 360 |
| aaagacgtcg actttgcagt cgtcctcaag gattttatcc tggaacatta cagtgaagat | 420 |
| ggctatttat atgaagatga aattgcagat cttatggatc tgagacaagc ttgtcggacg | 480 |
| cctagccggg atgaggccgg ggtggaactg ctgatgacat acttcatcca gctgggcttt | 540 |
| gtcgagagtc gattcttccc gcccacacgg cagatgggac tcctgttcac ctggtatgac | 600 |
| tctctcactg gggttccggt cagccagcag aacctgctgc tggagaaggc cagtgtcctg | 660 |
| ttcaacactg gggccctcta cacccagatt gggacccggt gcgatcggca gacgcaggct | 720 |
| gggctggaga gtgccataga tgcctttcag agagccgcag gggttttaaa ttacctgaaa | 780 |
| gacacattta cccatactcc aagttacgac atgagccctg ccatgctcag cgtgctcgtc | 840 |
| aaaatgatgc ttgcacaagc ccaagaaagc gtgtttgaga aaatcagcct tcctgggatc | 900 |
| cggaatgaat tcttcatgct ggtgaaggtg gctcaggagg ctgctaaggt gggagaggtc | 960 |
| taccaacagc tacacgcagc catgagccag gcgccggtga agagaacat cccctactcc | 1020 |
| tgggccagct tagcctgcgt gaaggcccac cactacgcgg ccctggccca ctacttcact | 1080 |
| gccatcctcc tcatcgacca ccaggtgaag ccaggcacgg atctggacca ccaggagaag | 1140 |
| tgcctgtccc agctctacga ccacatgcca gaggggctga cacccttggc cacactgaag | 1200 |
| aatgatcagc agcgccgaca gctggggaag tcccacttgc gcagagccat ggctcatcac | 1260 |
| gaggagtcgg tgcgggaggc gagcctctgc aagaagctgc ggagcattga ggtgctacag | 1320 |
| aagtgctgt gtgccgcaca ggaacgctcc cggctcacgt acgcccagca ccaggaggag | 1380 |
| gatgacctg tgaacctgat cgacgccccc agtgttgttg ctaaaactga gcaagaggtt | 1440 |
| gacattatat tgccccagtt ctccaagctg acagtcacgg acttcttcca gaagctgggc | 1500 |
| cccttatctg tgttttcggc taacaagcgg tggacgcctc ctcgaagcat ccgcttcact | 1560 |

-continued

```
gcagaagaag gggacttggg gttcaccttg agagggaacg cccccgttca ggttcacttc      1620
ctggatcctt actgctctgc ctcggtggca ggagcccggg aaggagatta tattgtctcc      1680
attcagcttg tggattgtaa gtggctgacg ctgagtgagg ttatgaagct gctgaagagc      1740
tttggcgagg acgagatcga gatgaaagtc gtgagcctcc tggactccac atcatccatg      1800
cataataaga gtgccacata ctccgtggga atgcagaaaa cgtactccat gatctgctta      1860
gccattgatg atgacgacaa aactgataaa accaagaaaa tctccaagaa gctttccttc      1920
ctgagttggg gcaccaacaa gaacagacag aagtcagcca gcaccttgtg cctcccatcg      1980 gtcgggctg cacggcctca ggtcaagaag aagctgccct cccctttcag ccttctcaac       2040
tcagacagtt cttggtacta atgtgaggaa acaaacatgt tcaggccccg aacatttccg      2100
gtgctgactc ggccttaaac gtttgtgcca taatggaaaa tatctatcta tctgttctca     2160
aatcctgttt ttctcatagt gtaaactcac atttgatgtg tttttatgaa ggaaagtaac     2220
caagaaacct ctaggaatta gtgaaaaaag aacttttttg aggtgtgtta ctatactgct     2280
gtaagttatt tattatataa agtattgtaa atagaatagt gttgaagata tgaaatatgg     2340 ctattttttaa tggtgacaat tatgactttt agtcactatt aaattggggt tacctatatc    2400
agtacaattt gtagttgttt ccaggtttgg ctaataatca ttccttaacc tagaattcag     2460
atgatcctgg aattaaggca ggtcagagga ctgtaatgat agaattaaat tagtgtcact    2520
aaaaactgtc ccaaagtgct gcttcctaat aggaattcat taacctaaaa caagatgtta    2580
ctattatatc gatagactat gaatgctatt tctagaaaaa gtctagtgcc aaatttgtct    2640
tattaaataa aaacaatgta ggagcagctt ttcttctagt ttgatgtcat ttaagaatta    2700
ctaacacagt ggcagtgtta gatgaagatg ctgtctacaa ggtagataat atactgtttg    2760
atactcaaaa cattttttcat tttgtttaaa gtagaagtta cataattcta tattttaagt    2820
cttgggtaaa aaagtagttt tacattttat aaagtaaaga tgtaaatgat tcaggtttaa    2880
agctctattt gacttccttt ttttgtttga gatagcgtct tgctgtgttg cccaggctgg    2940
agtgcagtgg tgtgatctca gctcagtgca acctccgccc cctgggatca agcgattctc    3000
ctacctcagc ctcccaaata gctgggacta caaggtgccc tccagcatgc ctggctgatt    3060
tttgtatttt tagttgaggt gaggtttcac catgttggcc aggcgggttt cgaaatcctg    3120
acctcaaatg atccacccac ctcagcctcc caaagtgctg ggattacagg catgagccac    3180
cacaaccgtc ccactatttt acttttaaa atgacattcc tactgattga tttttatctt      3240
gctataagtt cgatgacacc gtgaatctaa taaggttcac tgttgacaca gtacaagtta    3300
catagctaaa atcatagca ttgaagacta attttaagga ttgacaagag tttattttct     3360
attgtgcaat atcttaaagg aagcaaccac ctttgggaaa gtgtatctgc tgctcctagg    3420
gccatgcttg tatacatatt taaataaaca tattcattta cccgaaaaaa aaaaaaaaa     3480 aaaaaaaaa aaaaaaaa aaaaaaaaa aaaaaaaaa aaaaa                          3526
```

<210> SEQ ID NO 52
<211> LENGTH: 2100
<212> TYPE: DNA
<213> ORGANISM: Homo sapiens

<400> SEQUENCE: 52

```
atgaccgacg cgctgttgcc cgcggccccc cagccgctgg agaaggagaa cgacggctac       60
tttcggaagg gctgtaatcc ccttgcacaa accggccgga gtaaattgca gaatcaaaga      120
```

```
gctgctttga atcagcagat cctgaaagcc gtgcggatga ggaccggagc ggaaaacctt    180
ctgaaagtgg ccacaaactc aaggtgcgg  gagcaagtgc ggctggagct gagcttcgtc    240
aactcagacc tgcagatgct caaggaagag ctggaggggc tgaacatctc ggtgggcgtc    300
tatcagaaca cagaggaggc atttacgatt cccctgattc ctcttggcct gaaggaaacg    360
aaagacgtcg actttgcagt cgtcctcaag gattttatcc tggaacatta cagtgaagat    420
ggctatttat atgaagatga aattgcagat cttatggatc tgagacaagc ttgtcggacg    480
cctagccggg atgaggccgg ggtggaactg ctgatgacat acttcatcca gctgggcttt    540
gtcgagagtc gattcttccc gcccacacgg cagatggact cctgttcac  ctggtatgac    600 tctctcactg gggttccggt cagccagcag aacctgctgc tggagaaggc cagtgtcctg    660
ttcaacactg gggccctcta cacccagatt gggacccgt  gcgatcggca gacgcaggct    720
gggctggaga gtgccataga tgcctttcag agagccgcag gggttttaaa ttacctgaaa    780
gacacattta cccatactcc aagttacgac atgagccctg ccatgctcag cgtgctcgtc    840
aaaatgatgc ttgcacaagc ccaagaaagc gtgtttgaga aaatcagcct tcctgggatc    900
cggaatgaat tcttcatgct ggtgaaggtg gctcaggagg ctgctaaggt gggagaggtc    960
taccaacagc tacacgcagc catgagccag gcgccggtga agagaacat  cccctactcc   1020 tgggccagct agcctgcgt  gaaggcccac cactacgcgg ccctggccca ctacttcact   1080
gccatcctcc tcatcgacca ccaggtgaag ccaggcacgg atctggacca ccaggagaag   1140
tgcctgtccc agctctacga ccacatgcca gaggggctga cacccttggc cacactgaag   1200
aatgatcagc agcgccgaca gctggggaag tcccacttgc gcagagccat ggctcatcac   1260
gaggagtcgg tgcgggaggc gagcctctgc aagaagctgc ggagcattga ggtgctacag   1320
aaggtgctgt gtgccgcaca ggaacgctcc cggctcacgt acgcccagca ccaggaggag   1380
gatgacctgc tgaacctgat cgacgccccc agtgttgttg ctaaaactga gcaagaggtt   1440
gacattatat tgccccagtt ctccaagctg acagtcacgg acttcttcca gaagctgggc   1500
cccttatctg tgttttcggc taacaagcgg tggacgcctc ctcgaagcat ccgcttcact   1560
gcagaagaag gggacttggg gttcaccttg agagggaacg ccccgttca  ggttcacttc   1620 ctggatcctt actgctctgc ctcggtggca ggagcccggg aaggagatta tattgtctcc   1680
attcagcttg tggattgtaa gtggctgacg ctgagtgagg ttatgaagct gctgaagagc   1740
tttggcgagg acgagatcga gatgaaagtc gtgagcctcc tggactccac atcatccatg   1800
cataataaga gtgccacata ctccgtggga atgcagaaaa cgtactccat gatctgctta   1860
gccattgatg atgacgacaa aactgataaa accaagaaaa tctccaagaa gctttccttc   1920
ctgagttggg gcaccaacaa gaacagacag aagtcagcca gcaccttgtg cctcccatcg   1980
gtcggggctg cacggcctca ggtcaagaag aagctgccct cccctttcag ccttctcaac   2040
tcagacagtt cttggtacta atgtgaggaa acaaacatgt tcaggccccg aacatttccg   2100
```

<210> SEQ ID NO 53  
<211> LENGTH: 686  
<212> TYPE: PRT  
<213> ORGANISM: Homo sapiens

<400> SEQUENCE: 53

Met Thr Asp Ala Leu Leu Pro Ala Ala Pro Gln Pro Leu Glu Lys Glu
1               5                   10                  15

Asn Asp Gly Tyr Phe Arg Lys Gly Cys Asn Pro Leu Ala Gln Thr Gly
            20                  25                  30

-continued

```
Arg Ser Lys Leu Gln Asn Gln Arg Ala Ala Leu Asn Gln Gln Ile Leu
        35                  40                  45

Lys Ala Val Arg Met Arg Thr Gly Ala Glu Asn Leu Leu Lys Val Ala
 50                  55                  60

Thr Asn Ser Lys Val Arg Glu Gln Val Arg Leu Glu Leu Ser Phe Val
 65                  70                  75                  80

Asn Ser Asp Leu Gln Met Leu Lys Glu Leu Glu Gly Leu Asn Ile
                     85                  90                  95

Ser Val Gly Val Tyr Gln Asn Thr Glu Glu Ala Phe Thr Ile Pro Leu
                100                 105                 110

Ile Pro Leu Gly Leu Lys Glu Thr Lys Asp Val Asp Phe Ala Val Val
            115                 120                 125

Leu Lys Asp Phe Ile Leu Glu His Tyr Ser Glu Asp Gly Tyr Leu Tyr
130                 135                 140

Glu Asp Glu Ile Ala Asp Leu Met Asp Leu Arg Gln Ala Cys Arg Thr
145                 150                 155                 160

Pro Ser Arg Asp Glu Ala Gly Val Glu Leu Leu Met Thr Tyr Phe Ile
                165                 170                 175

Gln Leu Gly Phe Val Glu Ser Arg Phe Phe Pro Thr Arg Gln Met
            180                 185                 190

Gly Leu Leu Phe Thr Trp Tyr Asp Ser Leu Thr Gly Val Pro Val Ser
            195                 200                 205

Gln Gln Asn Leu Leu Glu Lys Ala Ser Val Leu Phe Asn Thr Gly
            210                 215                 220

Ala Leu Tyr Thr Gln Ile Gly Thr Arg Cys Asp Arg Gln Thr Gln Ala
225                 230                 235                 240

Gly Leu Glu Ser Ala Ile Asp Ala Phe Gln Arg Ala Gly Val Leu
                245                 250                 255

Asn Tyr Leu Lys Asp Thr Phe Thr His Thr Pro Ser Tyr Asp Met Ser
                260                 265                 270

Pro Ala Met Leu Ser Val Leu Val Lys Met Met Leu Ala Gln Ala Gln
            275                 280                 285

Glu Ser Val Phe Glu Lys Ile Ser Leu Pro Gly Ile Arg Asn Glu Phe
290                 295                 300

Phe Met Leu Val Lys Val Ala Gln Glu Ala Lys Val Gly Glu Val
305                 310                 315                 320

Tyr Gln Gln Leu His Ala Ala Met Ser Gln Ala Pro Val Lys Glu Asn
                325                 330                 335

Ile Pro Tyr Ser Trp Ala Ser Leu Ala Cys Val Lys Ala His His Tyr
            340                 345                 350

Ala Ala Leu Ala His Tyr Phe Thr Ala Ile Leu Leu Ile Asp His Gln
            355                 360                 365

Val Lys Pro Gly Thr Asp Leu Asp His Gln Glu Lys Cys Leu Ser Gln
370                 375                 380

Leu Tyr Asp His Met Pro Glu Gly Leu Thr Pro Leu Ala Thr Leu Lys
385                 390                 395                 400

Asn Asp Gln Gln Arg Gln Leu Gly Lys Ser His Leu Arg Arg Ala
                405                 410                 415

Met Ala His His Glu Glu Ser Val Arg Glu Ala Ser Leu Cys Lys Lys
            420                 425                 430

Leu Arg Ser Ile Glu Val Leu Gln Lys Val Leu Cys Ala Ala Gln Glu
435                 440                 445
```

```
Arg Ser Arg Leu Thr Tyr Ala Gln His Gln Glu Asp Leu Leu
    450                 455                 460

Asn Leu Ile Asp Ala Pro Ser Val Val Ala Lys Thr Glu Gln Glu Val
465                 470                 475                 480

Asp Ile Ile Leu Pro Gln Phe Ser Lys Leu Thr Val Thr Asp Phe Phe
                485                 490                 495

Gln Lys Leu Gly Pro Leu Ser Val Phe Ser Ala Asn Lys Arg Trp Thr
                500                 505                 510

Pro Pro Arg Ser Ile Arg Phe Thr Ala Glu Glu Gly Asp Leu Gly Phe
            515                 520                 525

Thr Leu Arg Gly Asn Ala Pro Val Gln Val His Phe Leu Asp Pro Tyr
    530                 535                 540

Cys Ser Ala Ser Val Ala Gly Ala Arg Glu Gly Asp Tyr Ile Val Ser
545                 550                 555                 560

Ile Gln Leu Val Asp Cys Lys Trp Leu Thr Leu Ser Glu Val Met Lys
                565                 570                 575

Leu Leu Lys Ser Phe Gly Glu Asp Glu Ile Glu Met Lys Val Val Ser
                580                 585                 590

Leu Leu Asp Ser Thr Ser Met His Asn Lys Ser Ala Thr Tyr Ser
                595                 600                 605

Val Gly Met Gln Lys Thr Tyr Ser Met Ile Cys Leu Ala Ile Asp Asp
    610                 615                 620

Asp Asp Lys Thr Asp Lys Thr Lys Ile Ser Lys Lys Leu Ser Phe
625                 630                 635                 640

Leu Ser Trp Gly Thr Asn Lys Asn Arg Gln Lys Ser Ala Ser Thr Leu
                645                 650                 655

Cys Leu Pro Ser Val Gly Ala Ala Arg Pro Gln Val Lys Lys Lys Leu
                660                 665                 670

Pro Ser Pro Phe Ser Leu Leu Asn Ser Asp Ser Ser Trp Tyr
            675                 680                 685

<210> SEQ ID NO 54
<211> LENGTH: 50
<212> TYPE: DNA
<213> ORGANISM: Homo sapiens

<400> SEQUENCE: 54
aaaaaaaata aataaaaagg ccgggcgcgt tggcccgcgc ctgcagcccc              50

<210> SEQ ID NO 55
<211> LENGTH: 869
<212> TYPE: DNA
<213> ORGANISM: Homo sapiens

<400> SEQUENCE: 55
tgctacttgg gaggctgagg ctggagcatc gcttgatcct gggaggtcga ggctgcaaag    60
agtcgagatc gcaacactgc tctccagcct gggcgacaga gcgaggtccc atctcttaaa   120
aaaaagaact gtgctcaagg acatctgccg tgtctggggc gcaaaacccc tcctggtccc   180
ctctctcagg gcagtccgcg agcccagcgg atcccactcg tctttgcagc gcggacaggg   240
aatcggctga gttgatccca tgccaacaag cccgagtagt ccgggcaagg cgctcggcgg   300
ggcagtcaac gctccctccg ccatgggctc ccctcttggg aaaagctttt ccaaaccgcc   360
gggcccaggg cccagagctc ccgccgcgcc ctcgacgtgg cgtcgagtct ggcccccttcc  420 cccgcggcgc acgggcttca cccaggaggg acgcgcctgg atccacgcct tcctcactga   480
```

```
ctccccgggc tccagggcag ggtgcaggtc cacagccagg gcttcgctgc ggccctgag       540 accccagtgc ctttcctgcg ctctcgcggc actcgcaaag ttgagtcagc cacgacgccc      600
acagacaacc ccgaggcgcc cgcccaggg cgcagctctc cgggtgacga gcgcctcaag       660
gggcgcgggt tcggggcccg cgacggggcg gggcgcgtct ccaggctcc agtgctcggc       720 ctcaggcggg gctagaaggg ccgcgggacg ggtgggagt ggaggggcgg ggaaggggcgg      780 ggacaggggc ggggccgcac gtcctctcgg gccagcctca ccgccgcgc ctcagtccgc       840 cgtccgccct ccgcgcccgc gccgctagc                                        869
```

<210> SEQ ID NO 56
<211> LENGTH: 69
<212> TYPE: DNA
<213> ORGANISM: Homo sapiens

<400> SEQUENCE: 56

```
atgaccgacg cgctgttgcc cgcggccccc cagccgctgg agaaggagaa cgacggctac       60
tttcggaag                                                              69
```

<210> SEQ ID NO 57
<211> LENGTH: 117
<212> TYPE: DNA
<213> ORGANISM: Homo sapiens

<400> SEQUENCE: 57

```
ggctgtaatc cccttgcaca aaccggccgg agtaaattgc agaatcaaag agctgctttg       60
aatcagcaga tcctgaaagc cgtgcggatg aggaccggag cggaaaacct tctgaaa         117
```

<210> SEQ ID NO 58
<211> LENGTH: 129
<212> TYPE: DNA
<213> ORGANISM: Homo sapiens

<400> SEQUENCE: 58

```
gtggccacaa actcaaaggt gcgggagcaa gtgcggctgg agctgagctt cgtcaactca       60
gacctgcaga tgctcaagga agagctggag gggctgaaca tctcggtggg cgtctatcag      120
aacacagag                                                              129
```

<210> SEQ ID NO 59
<211> LENGTH: 75
<212> TYPE: DNA
<213> ORGANISM: Homo sapiens

<400> SEQUENCE: 59

```
gaggcattta cgattcccct gattcctctt ggcctgaagg aaacgaaaga cgtcgacttt       60
gcagtcgtcc tcaag                                                       75
```

<210> SEQ ID NO 60
<211> LENGTH: 79
<212> TYPE: DNA
<213> ORGANISM: Homo sapiens

<400> SEQUENCE: 60

```
gattttatcc tggaacatta cagtgaagat ggctatttat atgaagatga aattgcagat       60
cttatggatc tgagacaag                                                   79
```

<210> SEQ ID NO 61
<211> LENGTH: 124

```
<212> TYPE: DNA
<213> ORGANISM: Homo sapiens

<400> SEQUENCE: 61
cttgtcggac gcctagccgg gatgaggccg gggtggaact gctgatgaca tacttcatcc        60
agctgggctt tgtcgagagt cgattcttcc cgcccacacg gcagatggga ctcctgttca       120
cctg                                                                    124

<210> SEQ ID NO 62
<211> LENGTH: 167
<212> TYPE: DNA
<213> ORGANISM: Homo sapiens

<400> SEQUENCE: 62
gtatgactct ctcactgggg ttccggtcag ccagcagaac ctgctgctgg agaaggccag        60
tgtcctgttc aacactgggg ccctctacac ccagattggg accggtgcg atcggcagac        120
gcaggctggg ctggagagtg ccatagatgc ctttcagaga gccgcag                     167

<210> SEQ ID NO 63
<211> LENGTH: 188
<212> TYPE: DNA
<213> ORGANISM: Homo sapiens

<400> SEQUENCE: 63
gggttttaaa ttacctgaaa gacacattta cccatactcc aagttacgac atgagccctg        60
ccatgctcag cgtgctcgtc aaaatgatgc ttgcacaagc ccaagaaagc gtgtttgaga       120
aaatcagcct tcctgggatc cggaatgaat tcttcatgct ggtgaaggtg gctcaggagg       180
ctgctaag                                                                188

<210> SEQ ID NO 64
<211> LENGTH: 156
<212> TYPE: DNA
<213> ORGANISM: Homo sapiens

<400> SEQUENCE: 64
gtgggagagg tctaccaaca gctacacgca gccatgagcc aggcgccggt gaaagagaac        60
atcccctact cctgggccag cttagcctgc gtgaaggccc accactacgc ggccctggcc       120
cactacttca ctgccatcct cctcatcgac caccag                                 156

<210> SEQ ID NO 65
<211> LENGTH: 120
<212> TYPE: DNA
<213> ORGANISM: Homo sapiens

<400> SEQUENCE: 65
gtgaagccag gcacggatct ggaccaccag gagaagtgcc tgtcccagct ctacgaccac        60
atgccagagg ggctgacacc cttggccaca ctgaagaatg atcagcagcg ccgacagctg       120

<210> SEQ ID NO 66
<211> LENGTH: 196
<212> TYPE: DNA
<213> ORGANISM: Homo sapiens

<400> SEQUENCE: 66
gggaagtccc acttgcgcag agccatggct catcacgagg agtcggtgcg ggaggcgagc        60
ctctgcaaga agctgcggag cattgaggtg ctacagaagg tgctgtgtgc cgcacaggaa       120
```

```
cgctcccggc tcacgtacgc ccagcaccag gaggaggatg acctgctgaa cctgatcgac      180
gcccccagtg ttgttg                                                     196

<210> SEQ ID NO 67
<211> LENGTH: 77
<212> TYPE: DNA
<213> ORGANISM: Homo sapiens

<400> SEQUENCE: 67
ctaaaactga gcaagaggtt gacattatat tgccccagtt ctccaagctg acagtcacgg       60
acttcttcca gaagctg                                                    77

<210> SEQ ID NO 68
<211> LENGTH: 147
<212> TYPE: DNA
<213> ORGANISM: Homo sapiens

<400> SEQUENCE: 68
ggccccttat ctgtgttttc ggctaacaag cggtggacgc tcctcgaag catccgcttc       60 actgcagaag aagggacttt ggggttcacc ttgagaggga acgcccccgt tcaggttcac     120
ttcctggatc cttactgctc tgcctcg                                        147

<210> SEQ ID NO 69
<211> LENGTH: 156
<212> TYPE: DNA
<213> ORGANISM: Homo sapiens

<400> SEQUENCE: 69
gtggcaggag cccgggaagg agattatatt gtctccattc agcttgtgga ttgtaagtgg      60
ctgacgctga gtgaggttat gaagctgctg aagagctttg gcgaggacga gatcgagatg    120
aaagtcgtga gcctcctgga ctccacatca tccatg                              156

<210> SEQ ID NO 70
<211> LENGTH: 1726
<212> TYPE: DNA
<213> ORGANISM: Homo sapiens

<400> SEQUENCE: 70
cataataaga gtgccacata ctccgtggga atgcagaaaa cgtactccat gatctgctta      60
gccattgatg atgacgacaa aactgataaa accaagaaaa tctccaagaa gctttccttc    120
ctgagttggg gcaccaacaa gaacagacag aagtcagcca gcaccttgtg cctcccatcg    180 gtcgggctg cacggcctca ggtcaagaag aagctgcccct cccctttcag ccttctcaac    240
tcagacagtt cttggtacta atgtgaggaa acaaacatgt tcaggccccg aacatttccg    300
gtgctgactc ggcctaaaac gtttgtgcca taatggaaaa tatctatcta tctgttctca    360
aatcctgttt ttctcatagt gtaaactcac atttgatgtg ttttatgaa ggaaagtaac     420 caagaaacct ctaggaatta gtgaaaaaag aacttttttg aggtgtgtta ctatactgct    480
gtaagttatt tattatataa agtattgtaa atagaatagt gttgaagata tgaaatatgg    540 ctattttaa tggtgacaat tatgactttt agtcactatt aaattggggt tacctatatc     600
agtacaattt gtagttgttt ccaggtttgg ctaataatca ttccttaacc tagaattcag    660
atgatcctgg aattaaggca ggtcagagga ctgtaatgat agaattaaat tagtgtcact    720
aaaaactgtc ccaaagtgct gcttcctaat aggaattcat taacctaaaa caagatgtta    780
ctattatatc gatagactat gaatgctatt tctagaaaaa gtctagtgcc aaatttgtct    840
```

| | | |
|---|---|---|
| tattaaataa aaacaatgta ggagcagctt tcttctagt ttgatgtcat ttaagaatta | 900 |
| ctaacacagt ggcagtgtta gatgaagatg ctgtctacaa ggtagataat atactgtttg | 960 |
| atactcaaaa cattttcat tttgtttaaa gtagaagtta cataattcta tattttaagt | 1020 |
| cttgggtaaa aaagtagttt tacatttat aaagtaaaga tgtaaatgat tcaggtttaa | 1080 |
| agctctattt gacttccttt ttttgtttga gatagcgtct tgctgtgttg cccaggctgg | 1140 |
| agtgcagtgg tgtgatctca gctcagtgca acctccgccc cctgggatca agcgattctc | 1200 |
| ctacctcagc ctcccaaata gctgggacta caaggtgccc tccagcatgc ctggctgatt | 1260 |
| tttgtatttt tagttgaggt gaggtttcac catgttggcc aggcgggttt cgaaatcctg | 1320 |
| acctcaaatg atccacccac ctcagcctcc caaagtgctg ggattacagg catgagccac | 1380 |
| cacaaccgtc ccactatttt acttttaaa atgacattcc tactgattga tttttatctt | 1440 |
| gctataagtt cgatgacacc gtgaatctaa taaggttcac tgttgacaca gtacaagtta | 1500 |
| catagctaaa atacatagca ttgaagacta atttaagga ttgacaagag tttattttct | 1560 |
| attgtgcaat atcttaaagg aagcaaccac ctttgggaaa gtgtatctgc tgctcctagg | 1620 |
| gccatgcttg tatacatatt taaataaaca tattcattta cccgaaaaaa aaaaaaaaa | 1680 |
| aaaaaaaaaa aaaaaaaaaa aaaaaaaaaa aaaaaaaaaa aaaaaa | 1726 |

<210> SEQ ID NO 71
<211> LENGTH: 643
<212> TYPE: PRT
<213> ORGANISM: Mus musculus

<400> SEQUENCE: 71

```
Met Ile Leu Glu Glu Arg Pro Asp Gly Gln Gly Thr Gly Glu Glu Ser
 1               5                  10                  15

Ser Arg Pro Gln Asp Asp Gly Ser Ile Arg Lys Gly Tyr Gly Ser Phe
            20                  25                  30

Val Gln Asn Gln Pro Gly Gln Leu Gln Ser His Arg Ala Arg Leu His
        35                  40                  45

Gln Gln Ile Ser Lys Glu Leu Arg Met Arg Thr Gly Ala Glu Asn Leu
    50                  55                  60

Tyr Arg Ala Thr Ser Asn Thr Trp Val Arg Glu Thr Val Ala Leu Glu
65                  70                  75                  80

Leu Ser Tyr Val Asn Ser Asn Leu Gln Leu Leu Lys Glu Glu Leu Ala
                85                  90                  95

Glu Leu Ser Thr Ser Val Asp Val Asp Gln Pro Glu Gly Glu Gly Ile
            100                 105                 110

Thr Ile Pro Met Ile Pro Leu Gly Leu Lys Glu Thr Lys Glu Leu Asp
        115                 120                 125

Trp Ala Thr Pro Leu Lys Glu Leu Ile Ser Glu His Phe Gly Glu Asp
    130                 135                 140

Gly Thr Ser Phe Glu Thr Glu Ile Gln Glu Leu Glu Asp Leu Arg Gln
145                 150                 155                 160

Ala Thr Arg Thr Pro Ser Arg Asp Glu Ala Gly Leu Asp Leu Leu Ala
                165                 170                 175

Ala Tyr Tyr Ser Gln Leu Cys Phe Leu Asp Ala Arg Phe Phe Ser Pro
            180                 185                 190

Ser Arg Ser Pro Gly Leu Leu Phe His Trp Tyr Asp Ser Leu Thr Gly
        195                 200                 205

Val Pro Ala Gln Gln Arg Ala Leu Ala Phe Glu Lys Gly Ser Val Leu
```

-continued

```
            210                 215                 220
Phe Asn Ile Gly Ala Leu His Thr Gln Ile Gly Ala Arg Gln Asp Cys
225                 230                 235                 240

Ser Cys Thr Glu Gly Thr Asn His Ala Ala Glu Ala Phe Gln Arg Ala
                245                 250                 255

Ala Gly Ala Phe Arg Leu Leu Arg Glu Asn Phe Ser His Ala Pro Ser
                260                 265                 270

Pro Asp Met Ser Ala Ala Ser Leu Ser Met Leu Glu Gln Leu Met Ile
                275                 280                 285

Ala Gln Ala Gln Glu Cys Ile Phe Lys Gly Leu Leu Leu Pro Ala Ser
290                 295                 300

Ala Thr Pro Asp Ile Cys Pro Asp Gln Leu Gln Leu Ala Gln Glu Ala
305                 310                 315                 320

Ala Gln Val Ala Thr Glu Tyr Gly Leu Val His Arg Ala Met Ala Gln
                325                 330                 335

Pro Pro Val Arg Asp Tyr Leu Pro Ala Ser Trp Thr Asn Leu Ala His
                340                 345                 350

Val Lys Ala Glu His Phe Cys Ala Leu Ala His Tyr His Ala Ala Met
                355                 360                 365

Ala Leu Cys Glu Ser His Pro Ala Lys Gly Glu Leu Ala Arg Gln Glu
                370                 375                 380

His Val Phe Gln Pro Ser Thr Pro His Glu Pro Leu Gly Pro Thr Leu
385                 390                 395                 400

Pro Gln His Pro Glu Asp Arg Arg Lys Leu Ala Lys Ala His Leu Lys
                405                 410                 415

Arg Ala Ile Leu Gly Gln Glu Ala Leu Arg Leu His Thr Leu Cys
                420                 425                 430

Arg Val Leu Arg Lys Val Asp Leu Leu Gln Val Val Thr Gln Ala
                435                 440                 445

Leu Arg Arg Ser Leu Ala Lys Tyr Ser Gln Leu Glu Arg Glu Asp Asp
                450                 455                 460

Phe Phe Glu Ala Thr Glu Ala Pro Asp Ile Gln Pro Lys Thr His Gln
465                 470                 475                 480

Thr Pro Glu Gly Pro Leu Ser Val Phe Ser Thr Lys Asn Arg Trp Gln
                485                 490                 495

Leu Val Gly Pro Val His Met Thr Arg Gly Glu Gly Phe Gly Phe
                500                 505                 510

Thr Leu Arg Gly Asp Ser Pro Val Leu Ile Ala Ala Val Val Pro Gly
                515                 520                 525

Gly Gln Ala Glu Ser Ala Gly Leu Lys Glu Gly Asp Tyr Ile Val Ser
                530                 535                 540

Val Asn Gly Gln Pro Cys Lys Trp Trp Lys His Leu Glu Val Val Thr
545                 550                 555                 560

Gln Leu Arg Ser Met Gly Glu Glu Gly Val Ser Leu Gln Val Val Ser
                565                 570                 575

Leu Leu Pro Ser Pro Glu Pro Arg Gly Thr Gly Pro Arg Arg Ala Ala
                580                 585                 590

Leu Leu Trp Asn Gln Arg Glu Cys Gly Phe Glu Thr Pro Met Pro Thr
                595                 600                 605

Arg Thr Arg Pro Trp Pro Ile Leu Gly Trp Ser Arg Lys Asn Lys Gln
                610                 615                 620

Gly Lys Thr Gly Ser His Pro Asp Pro Cys Thr Asn Arg Asn Cys Val
625                 630                 635                 640
```

Thr Cys Pro

<210> SEQ ID NO 72
<211> LENGTH: 718
<212> TYPE: PRT
<213> ORGANISM: Drosophila melanogaster

<400> SEQUENCE: 72

```
Met Asp Glu Lys Glu His Glu Leu Ser Thr Arg Val Val Lys Asn Glu
 1               5                  10                  15

Glu Asn Glu Asp Asp Glu Lys Leu Asn Glu Leu Ser Phe Cys Phe Val
            20                  25                  30

Arg Gly Ser Asp Pro Arg Ala Ala Thr Cys Arg Ser Lys Leu Gln Asn
        35                  40                  45

Arg Arg Cys Lys Leu Asn Lys Glu Ile Asn Lys Glu Leu Arg Leu Arg
    50                  55                  60

Ala Gly Ala Glu Asn Leu Tyr Lys Ala Thr Ser Asn Arg Lys Leu Arg
65                  70                  75                  80

Asp Thr Val Ala Leu Glu Leu Ser Phe Val Asn Ser Asn Leu Gln Leu
                85                  90                  95

Leu Lys Glu Gln Leu Ala Glu Leu Asn Ser Ser Val Glu Ile Tyr Gln
            100                 105                 110

Ser Glu Ser His Asn Gly Ile Met Pro Met Ile Pro Leu Gly Leu Lys
        115                 120                 125

Glu Thr Lys Glu Ile Asn Phe Met Glu Pro Phe Ser Asp Phe Ile Leu
    130                 135                 140

Glu His Tyr Ser Glu Glu Pro Ser Met Tyr Ile Asp Ala Ile Ala Asp
145                 150                 155                 160

Met Thr Asp Thr Arg Gln Ala Ser Lys Thr Pro Ser Arg Asp Ala Leu
                165                 170                 175

Gly Val Ala Leu Leu Phe Arg Tyr Tyr Asn Thr Leu Tyr Tyr Val Glu
            180                 185                 190

Arg Arg Phe Phe Pro Pro Asp Arg Asn Leu Gly Val Tyr Phe Glu Trp
        195                 200                 205

Tyr Asp Ser Leu Thr Gly Val Pro Ser Cys Gln Arg Thr Ile Ala Phe
    210                 215                 220

Glu Lys Ala Cys Thr Leu Phe Asn Leu Gly Gly Ile Tyr Thr Gln Ile
225                 230                 235                 240

Gly Ala Arg His Asp Arg Thr Thr Glu Arg Gly Leu Asp Leu Ala Val
                245                 250                 255

Asp Ser Phe Leu Arg Ala Ala Gly Val Phe Arg His Ile Tyr Asp Thr
            260                 265                 270

Phe Thr Asn Ala Pro Ser Met Asp Leu Lys Pro Gln Val Leu Asp Val
        275                 280                 285

Leu Val Ser Leu Met Leu Ser Gln Ala Arg Glu Cys Leu Phe Glu Lys
    290                 295                 300

Leu Gln Leu Gln Ile Glu Ala Met Ser His Asp Cys Gln Ala Phe Arg
305                 310                 315                 320

Asp Leu Ala Gly Glu Ala Ala Gln Ile Ser His Glu Tyr Asn Glu Met
                325                 330                 335

His Lys Asn Ile Gln Ala Asn Asp Thr His Thr Tyr Leu Pro Glu Cys
            340                 345                 350

Trp Ala Gly Leu Val Pro Val Lys Ala Glu Leu Tyr Lys Ala Phe Ala
        355                 360                 365
```

```
His Phe Tyr Lys Ala Arg Ser Ile Asp Ala Thr Asp Glu Leu Lys Ala
        370                 375                 380

Ser Lys Ser Ser Gln Lys Asn Gln Glu Ser Phe Ile Gly Asn Ser Gln
385                 390                 395                 400

Glu Val Glu Arg Ile Thr Thr Ala Asp Tyr Gly Ala Ser Asp Glu Ala
                405                 410                 415

Ser Thr Ser Ile Ala Asn Lys Leu Ala His Leu Lys Glu Ala Leu Ala
            420                 425                 430

Ser Ile Glu Glu Ala Gln Arg Leu Gln Arg Met Cys Arg Phe Leu Lys
        435                 440                 445

Asn Lys Ala Ser Leu Thr Glu Val Met Lys Glu Val His Ser Lys Ser
450                 455                 460

Gln Glu Glu Leu Glu Lys Phe Arg Leu Gln Ala Ser Ala Lys Asn Ile
465                 470                 475                 480

Glu Asp Gly Asp Leu Leu Glu Arg Ser Val Glu Ala Ser Ser Lys Phe
                485                 490                 495

Thr Leu Ser Leu Thr Gly Pro Asp Phe Thr Ser His Lys Val Lys Asp
            500                 505                 510

Pro Phe Lys Arg Leu Gly Pro Ile Ala Ile Phe Ser Ala Arg Arg His
        515                 520                 525

Trp Thr Ala Pro Arg Cys Val Arg Leu Gln Lys Gly Ser Ser Leu Tyr
530                 535                 540

His Ser Val Pro Ser Asn Asp Asn Lys Cys Pro Leu Asp Asn Asp Asp
545                 550                 555                 560

Asp Glu Glu His Asp Gly Gly Tyr Asn Leu Tyr Lys Glu Glu Phe Glu
                565                 570                 575

Asn Phe Gly Phe His Val Arg Gly Asp Ala Pro Val Ile Ile Ala His
            580                 585                 590

Val Glu Ile Asn Ser Leu Ala Asp Leu Gly Gly Ile Lys Glu Gly Asp
        595                 600                 605

Phe Ile Val Glu Ile Ala Gly Val Asp Val Lys Trp Tyr Ser His Gln
610                 615                 620

Gln Val Val Gln Leu Ile Gln Ser Cys Gly Ser Thr Leu Glu Leu Arg
625                 630                 635                 640

Val Ile Thr Pro Met Asp Arg Asn Tyr Leu Lys Pro Leu Ser Ser Lys
                645                 650                 655

Gly Ser Leu Ser Thr Leu Ser Ala Ala Ser Ser Gly Ile Ser Ser
            660                 665                 670

Gly Phe Pro Ser Pro Thr Ser Ile Ala Ala Lys Pro Lys Leu His Leu
        675                 680                 685

Lys Thr Ser Ser Ser Arg Pro Ala Gly Ser Val Ser Ser Ser Ser
690                 695                 700

Trp Asn Pro Phe Arg Arg Thr Pro Ser Leu Ala Lys Ile Phe
705                 710                 715

<210> SEQ ID NO 73
<211> LENGTH: 686
<212> TYPE: PRT
<213> ORGANISM: Mus musculus

<400> SEQUENCE: 73

Met Thr Asp Thr Leu Leu Pro Ala Ala Pro Gln Pro Leu Glu Lys Glu
1               5                   10                  15

Gly Asp Asp Tyr Phe Arg Lys Gly Cys Asn Pro Leu Ala Gln Thr Gly
```

-continued

```
                 20                  25                  30
Arg Ser Lys Leu Gln Asn Gln Arg Ala Ala Leu Asn Gln Gln Ile Leu
             35                  40                  45
Lys Ala Val Arg Met Arg Thr Gly Ala Glu Asn Leu Leu Lys Val Ala
 50                  55                  60
Thr Asn Gln Lys Val Arg Glu Gln Val Arg Leu Glu Leu Ser Phe Val
 65                  70                  75                  80
Asn Ser Asp Leu Gln Met Leu Lys Glu Glu Leu Glu Gly Leu Asn Ile
                 85                  90                  95
Ser Val Gly Val Tyr Gln Gly Thr Glu Glu Ala Phe Thr Ile Pro Leu
             100                 105                 110
Ile Pro Leu Gly Leu Lys Glu Thr Lys Glu Val Asp Phe Ser Ile Val
             115                 120                 125
Phe Lys Asp Phe Ile Leu Glu His Tyr Ser Glu Asp Ser Tyr Leu Tyr
             130                 135                 140
Glu Asp Asp Ile Ala Asp Leu Met Asp Leu Arg Gln Ala Cys Arg Thr
145                 150                 155                 160
Pro Ser Arg Asp Glu Ala Gly Val Glu Leu Leu Met Ser Tyr Phe Ile
                 165                 170                 175
Gln Leu Gly Phe Val Glu Ser Arg Phe Phe Pro Thr Arg His Met
             180                 185                 190
Gly Leu Leu Phe Thr Trp Tyr Asp Ser Phe Thr Gly Val Pro Val Ser
             195                 200                 205
Gln Gln Thr Leu Leu Glu Lys Ala Ser Val Leu Phe Asn Ile Gly
             210                 215                 220
Ala Leu Tyr Thr Gln Ile Gly Thr Arg Cys Asn Arg Gln Thr Gln Ala
225                 230                 235                 240
Gly Leu Glu Ser Ala Val Asp Ala Phe Gln Arg Ala Ala Gly Val Leu
                 245                 250                 255
Asn Tyr Leu Lys Glu Thr Phe Thr His Thr Pro Ser Tyr Asp Met Ser
             260                 265                 270
Pro Ala Met Leu Ser Val Leu Val Lys Met Met Leu Ala Gln Ala Gln
             275                 280                 285
Glu Ser Val Phe Glu Lys Val Cys Leu Pro Gly Ile Gln Asn Glu Phe
             290                 295                 300
Phe Val Leu Val Lys Val Ala Gln Glu Ala Ala Lys Val Ala Glu Ala
305                 310                 315                 320
Tyr Arg Gln Leu His Ala Ala Met Ser Gln Glu Pro Val Lys Glu Asn
                 325                 330                 335
Ile Pro Tyr Ser Trp Ala Ser Val Ala Tyr Val Lys Ala Tyr His Tyr
             340                 345                 350
Gly Ala Leu Ala His Tyr Phe Ala Ala Thr Leu Leu Ile Asp His Gln
             355                 360                 365
Leu Lys Pro Gly Ala Asp Glu Asp His Gln Glu Lys Cys Leu Ser Gln
             370                 375                 380
Leu Tyr Asp Arg Met Pro Glu Gly Met Thr Pro Leu Ala Thr Leu Lys
385                 390                 395                 400
Asn Ala Gly Gln Arg Val Leu Gly Lys Gly His Leu His Arg Ala
                 405                 410                 415
Ile Gly Phe His Glu Glu Ser Leu Arg Glu Ala Asn Leu Cys Lys Lys
             420                 425                 430
Leu Arg Asp Ile Gln Val Leu Arg Asp Val Leu Ser Ala Ala His Gln
             435                 440                 445
```

```
Arg Thr Gln Leu Lys His Thr Gln His Arg Glu Asp Asp Leu Leu
    450                 455                 460

Asn Leu Ile Asp Ala Pro Asp Val Leu Pro Lys Thr Glu Arg Glu Val
465                 470                 475                 480

Lys Ile Thr Phe Pro Asp Phe Ser Lys Val Thr Val Thr Asp Phe Phe
                485                 490                 495

Gln Lys Leu Gly Pro Leu Ser Val Phe Ser Ala Ser Lys Arg Trp Ser
            500                 505                 510

Pro Pro Arg Gly Ile His Phe Thr Val Glu Glu Gly Asp Leu Gly Phe
        515                 520                 525

Thr Leu Arg Gly Asn Thr Pro Val Gln Val His Phe Leu Asp Pro His
    530                 535                 540

Cys Ser Ala Ser Leu Ala Gly Ala Lys Glu Gly Asp Tyr Ile Val Ser
545                 550                 555                 560

Ile Gln Gly Val Asp Cys Lys Trp Leu Thr Val Ser Glu Val Met Lys
                565                 570                 575

Leu Leu Lys Ser Phe Gly Gly Glu Glu Val Glu Met Lys Val Val Ser
            580                 585                 590

Leu Leu Asp Ser Thr Ser Ser Met His Asn Lys Cys Ala Thr Tyr Ser
        595                 600                 605

Val Gly Met Gln Lys Thr Tyr Ser Met Ile Cys Leu Ser Met Asp Asp
    610                 615                 620

Asp Asp Lys Ala Asp Lys Thr Lys Lys Ile Ser Lys Lys Leu Ser Phe
625                 630                 635                 640

Leu Ser Trp Gly Thr Ser Lys Asn Arg Gln Lys Ser Ala Ser Thr Leu
                645                 650                 655

Cys Leu Pro Glu Val Gly Leu Ala Arg Ser Gln Asn Lys Lys Lys Leu
            660                 665                 670

Pro Thr Pro Phe Ser Leu Leu Asn Ser Asp Ser Ser Leu Tyr
        675                 680                 685
```

PROSTATE-SPECIFIC OR TESTIS-SPECIFIC NUCLEIC ACID MOLECULES, POLYPEPTIDES, AND DIAGNOSTIC AND THERAPEUTIC METHODS

CROSS-REFERENCE TO RELATED APPLICATION

This application claims priority from copending PCT Application No. PCT/US01/09410, filed Mar. 23, 2001, which claims priority from U.S. Provisional Application Ser. No. 60/191,929, filed Mar. 24, 2000 (now abandoned).

FIELD OF THE INVENTION

The invention generally relates to the treatment of disorders associated with prostate and testis dysfunction and cell proliferation, and specifically relates to the identification and use of novel genes for diagnosis and treatment of such disorders.

BACKGROUND OF THE INVENTION

Genitourinary disorders are often difficult to diagnose and treat effectively because they are present non-specifically. Two causes of genitourinary disorders are disorders of the prostate gland and the testis.

The prostate is a variable sized gland located in the male pelvis, and is made up of several different cell types, including epithelial cells and stromal cells. Prostate-associated disorders include prostate cancer, benign prostatic hyperplasia, and prostatitis. The male hormone testosterone and other androgen related hormones have major roles in the growth and function of the prostate. The testis is also subject to many defects, including developmental anomalies, inflammation, and cancer.

In men, prostate cancer is the most commonly diagnosed cancer and the second leading cause of cancer mortality following skin cancer. In the initial stages, prostate cancer is dependent on androgens for growth, and this dependence is the basis for androgen ablation therapy. In most cases, however, prostate cancer progresses to an androgen-independent phenotype for which there is no effective therapy available at present.

Currently, there is limited information regarding the molecular details of prostate cancer progression. Several independent approaches resulted in the identification of a few highly prostate-enriched genes that may have unique roles in this process. The first such gene discovered was Prostate Specific Antigen (PSA), the detection of which is currently used as a diagnostic tool and also as a marker for the progression of prostate cancer, albeit with significant limitations. More recently, several additional prostate-enriched genes were identified including prostate-specific membrane antigen (PSMA), prostate carcinoma tumor antigen 1 (PCTA-1), NKX3.1, prostate stem cell antigen (PSCA), DD3, and PCGEM1.

It would be beneficial to provide reagents useful for the diagnosis and therapy of disorders associated with the prostate and the testis, as well as other tissues.

SUMMARY OF THE INVENTION

The invention provides, in general, a novel prostate-specific or testis-specific nucleic acid molecules, polypeptides, antibodies, and modulatory compounds for use in methods of diagnosing, treating, and preventing diseases and conditions of the prostate and testis, such as cancer.

In a first aspect the invention provides a substantially pure prostate-specific or testis-specific polypeptide, including a sequence substantially identical to the sequence of any of SEQ ID NOS: 14, 29, 32, 34, 36, 41, or 53. In a preferred embodiment of the first aspect, the substantially pure prostate-specific or testis-specific polypeptide includes the sequence of any of SEQ ID NOS: 14, 29, 32, 34, 36, 41, or 53. In another preferred embodiment, the invention provides an isolated nucleic acid molecule encoding a polypeptide of the first aspect, for example a nucleic acid molecule including the sequence of any of SEQ ID NOS: 23, 28, 31, 33, 35, 40, or 52. Preferably, the polypeptide is derived from a mammal, e.g., a human.

In a second aspect, the invention provides an isolated prostate-specific or testis-specific nucleic acid molecule including a sequence substantially identical to SEQ ID NOS: 1–12, 22, 27, 30, and 51.

In a third aspect, the invention provides an isolated prostate-specific or testis-specific nucleic acid molecule consisting essentially of SEQ ID NOS: 15–21, 24–26, 42–50, and 54–70.

In preferred embodiments of some of the above aspects, the invention provides a vector, a cell, a cell including the vector, and a non-human transgenic animal including the isolated nucleic acid molecules.

In a fourth aspect, the invention provides an isolated nucleic acid molecule that hybridizes under high stringency conditions to the complement of any of the sequences set forth in SEQ ID NOS: 1–12, 15–28, 30, 31, 33, 35, 40, 42–50, 51, 52, or 54–70, where the isolated nucleic acid molecule encodes a prostate-specific or testis-specific polypeptide.

In a fifth aspect, the invention provides an isolated nucleic acid molecule, where the nucleic acid molecule includes a sequence that is antisense to the coding strand of any of the prostate-specific or testis-specific nucleic acid molecules set forth in SEQ ID NOS: 1–12, 15–28, 30, 31, 33, 35, 40, 42–50, 51, 52, or 54–70, or a fragment thereof.

In a sixth aspect, the invention provides a probe for analyzing a prostate-specific or testis-specific gene or homolog or fragment thereof, the probe having greater than 55% nucleotide sequence identity to a sequence encoding any of SEQ ID NOS: 1–12, 15–28, 30, 31, 33, 35, 40, 42–50, 51, 52, or 54–70, or fragment thereof, where the fragment includes at least six amino acids, and the probe hybridizes under high stringency conditions to at least a portion of a prostate-specific or testis-specific nucleic acid molecule. In a preferred embodiment of this aspect, the probe has 100% complementarity to a nucleic acid molecule encoding any of SEQ ID NOS: 1–12, 15–28, 30, 31, 33, 35, 40, 42–50, 51, 52, or 54–70, or fragment thereof, where the fragment comprises at least six amino acids, and said probe hybridizes under high stringency conditions to at least a portion of a prostate-specific or testis-specific nucleic acid molecule.

In a seventh aspect, the invention provides an antibody that specifically binds to a prostate-specific or testis-specific polypeptide that includes an amino acid sequence that is substantially identical to the amino acid sequence of any of SEQ ID NOS: 14, 29, 32, 34, 36, 41, or 53.

In an eighth aspect, the invention provides a method of detecting a prostate-specific or testis-specific gene or fragment thereof in a cell, the method including contacting the nucleic acid molecule of any of SEQ ID NOS: 1–12, 15–28, 30, 31, 33, 35, 40, 42–50, 51, 52, or 54–70, or a fragment thereof, where the fragment is greater than about 18 nucleotides in length, with a preparation of genomic DNA from the cell, under high stringency hybridization conditions, and detecting DNA sequences having about 55% or greater nucleotide sequence identity to any of SEQ ID NOS: 1–12, 15–28, 30, 31, 33, 35, 40, 42–50, 51, 52, or 54–70, thus identifying a prostate-specific or testis-specific gene or fragment thereof. Nucleotides encoding the polypeptides of SEQ ID NOS: 38, 39, or 71–73 can also be used in an embodiment of this aspect. In a preferred embodiment of this aspect, the method includes detecting a neoplastic or cancer cell in a patient predisposed to or at risk for cancer, for example, for prostate cancer.

In a ninth aspect, the invention provides a method for identifying a test compound that modulates the expression or activity of a prostate-specific or testis-specific polypeptide, the method including contacting the prostate-specific or testis-specific polypeptide with the test compound, and determining the effect of the test compound on the prostate-specific or testis-specific polypeptide expression or activity. In a preferred embodiments of this aspect, the prostate-specific or testis-specific polypeptide includes an amino acid sequence substantially identical to the amino acid sequence of SEQ ID NOS: 14, 29, 32, 34, 36, 38, 39, 41, 53, or 71–73, and fragments and analogs thereof.

In a tenth aspect, the invention provides a method of treating a mammal having a disorder of the prostate or testis, the method including administering to the mammal a therapeutically effective amount of a compound that modulates the activity or expression of a prostate-specific or testis-specific polypeptide, where the compound has a beneficial effect on the disorder in the mammal. In preferred embodiments of this aspect, the disorder is prostate cancer, the mammal is a human, or the prostate-specific or testis-specific polypeptide includes an amino acid sequence substantially identical to the amino acid sequence of SEQ ID NOS: 14, 29, 32, 34, 36, 38, 39, 41, 53, or 71–73, and fragments and analogs thereof.

In an eleventh aspect, the invention provides a pharmaceutical composition including at least one dose of a therapeutically effective amount of a prostate-specific or testis-specific polypeptide or fragment thereof, in a pharmaceutically acceptable carrier, the composition being formulated for the treatment of a disorder of the prostate or testis.

In a twelfth aspect, the invention provides a kit for the analysis of a prostate-specific or testis-specific nucleic acid molecule, the kit including a nucleic acid molecule probe for analyzing a prostate-specific or testis-specific nucleic acid molecule present in a test subject.

In a thirteenth aspect, the invention provides a kit for the analysis of a prostate-specific or testis-specific polypeptide, the kit including an antibody for analyzing a prostate-specific or testis-specific polypeptide present in a test subject.

As used herein, by "polypeptide," "protein," or "polypeptide fragment" is meant a chain of two or more amino acids, regardless of any post-translational modification (e.g., glycosylation or phosphorylation), constituting all or part of a naturally or non-naturally occurring polypeptide. By "post-translational modification" is meant any change to a polypeptide or polypeptide fragment during or after synthesis. Post-translational modifications can be produced naturally (such as during synthesis within a cell) or generated artificially (such as by recombinant or chemical means). A protein can be made up of one or more polypeptides.

By "substantially pure polypeptide" or "substantially pure and isolated polypeptide" is meant a polypeptide (or a fragment thereof) that has been separated from components that naturally accompany it Typically, the polypeptide is substantially pure when it is at least 60%, by weight, free from the proteins and naturally occurring organic molecules with which it is naturally associated. Preferably, the polypeptide is a prostate-specific or a testis-specific polypeptide that is at least 75%, more preferably at least 90%, and most preferably at least 99%, by weight, pure. A substantially pure prostate-specific or a testis-specific polypeptide may be obtained by standard techniques, for example, by extraction from a natural source (e.g., prostate or testis tissue or cell lines), by expression of a recombinant nucleic acid encoding a prostate-specific or a testis-specific polypeptide, or by chemically synthesizing the polypeptide. Purity can be measured by any appropriate method, e.g., by column chromatography, polyacrylamide gel electrophoresis, or HPLC analysis.

A protein or polypeptide is substantially free of naturally associated components when it is separated from those contaminants that accompany it in its natural state. Thus, a protein that is chemically synthesized or produced in a cellular system different from the cell from which it naturally originates will be substantially free from its naturally associated components. Accordingly, substantially pure polypeptides not only include those derived from eukaryotic organisms but also those synthesized in *E. coli* or other prokaryotes.

The term "identity" is used herein to describe the relationship of the sequence of a particular nucleic acid molecule or polypeptide to the sequence of a reference molecule of the same type. For example, if a polypeptide or nucleic acid molecule has the same amino acid or nucleotide residue at a given position, compared to a reference molecule to which it is aligned, there is said to be "identity" at that position.

The level of sequence identity of a nucleic acid molecule or a polypeptide to a reference molecule is typically measured using sequence analysis software with the default parameters specified therein, such as the introduction of gaps to achieve an optimal alignment. The "identity" of two or more nucleic acid or polypeptide sequences can therefore be readily calculated by known methods, including but not limited to those described in *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, Academic Press, 1987; and *Sequence Analysis Primer*, Gribskov, and Devereux, eds., M. Stockton Press, New York, 1991; and Carillo and Lipman, SIAM J. Applied Math. 48:1073, 1988.

Methods to determine identity are available in publicly available computer programs. Computer program methods to determine identity between two sequences include, but are not limited to, the GCG program package (Devereux et al., Nucleic Acids Research 12(1): 387, 1984), BLASTP, BLASTN, and FASTA (Altschul et al., J. Mol. Biol. 215: 403 (1990). The well known Smith Waterman algorithm may also be used to determine identity. The BLAST program is publicly available from NCBI and other sources (*BLAST Manual*, Altschul, et al., NCBI NLM NIH Bethesda, Md. 20894). Searches can be performed in URLs such as the following http://www.ncbi.nlm.nih.gov/BLAST/unfinishedgenome.html; or http://www.tigr.org/cgi-bin/Blast-Search/blast.cgi. These software programs match similar sequences by assigning degrees of homology to various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

A nucleic acid molecule or polypeptide is said to be "substantially identical" to a reference molecule if it exhibits, over its entire length, at least 50%, 60%, or 70%, preferably at least 80% or 90%, more preferably at least 95%, and most preferably at least 99% identity to the sequence of the reference molecule. For polypeptides, the length of comparison sequences is at least 16 amino acids, preferably at least 20 amino acids or at least 25 amino acids, more preferably at least 35 amino acids, and most preferably, the full-length polypeptide. For nucleic acid molecules, the length of comparison sequences is at least 50 nucleotides, preferably at least 60 nucleotides, more preferably at least 75 nucleotides or at least 110 nucleotides, and most preferably, the full-length nucleic acid molecule. Alternatively, or additionally, two nucleic acid sequences are "substantially identical" if they hybridize under high stringency conditions.

By "isolated nucleic acid molecule," "substantially pure nucleic acid molecule," or "substantially pure and isolated nucleic acid molecule" is meant a nucleic acid molecule (for example, DNA) that is free of the genes that, in the naturally occurring genome of the organism from which the nucleic acid molecule of the invention is derived, flank the nucleic acid. The term includes, for example, a recombinant DNA that is incorporated into a vector; into an autonomously replicating plasmid or virus; or into the genomic DNA of a prokaryote or eukaryote; or that exists as a separate molecule (e.g., a cDNA or a genomic or cDNA fragment produced by PCR or restriction endonuclease digestion) independent of other sequences. It also includes a recombinant DNA that is part of a hybrid gene encoding additional polypeptide sequence.

By "antisense," as used herein in reference to nucleic acid molecules, is meant a molecule having a nucleic acid sequence, regardless of length, that is complementary to at least 75 nucleotides, and preferably at least 100, 150, or 200 nucleotides, of the coding strand of a nucleic acid molecule encoding a prostate-specific or a testis-specific polypeptide, as described herein. An antisense molecule may also include regulatory sequences such as transcription enhancers, hormone responsive elements, ribosomal- and RNA polymerase binding sites, etc., which may be located upstream or downstream of the coding region, and may have a distance of several ten base pairs to several ten thousand base pairs. An antisense nucleic acid molecule can be, for example, capable of preferentially lowering the production or expression of a prostate-specific or a testis-specific polypeptide encoded by a prostate-specific or a testis-specific nucleic acid molecule.

By "prostate-specific" or "testis-specific" nucleic acid molecule is meant a nucleic acid molecule, such as a genomic DNA, cDNA, or RNA (e.g., mRNA) molecule, having at least 50, 60, or 75%, more preferably at least 80, 85, or 95%, and most preferably at least 99% amino acid identity to the nucleic acid molecules described herein, for example, in FIGS. 4, 11, and 14. In addition, a nucleic acid molecule having at least 50, 60, or 75%, more preferably at least 80, 85, or 95%, and most preferably at least 99% nucleotide identity to a nucleotide sequence encoding amino acids 1–200 of STMP1 (SEQ ID NO: 14), preferably encoding amino acids 40–150 of STMP1, can be considered a prostate-specific or testis-specific nucleic acid molecule. Specifically excluded from this definition is STEAP (AF186249) (Hubert, R. S. et al., *Proc Natl Acad Sci USA* 96, 14523–14528, 1999) and nucleic acid molecule sequences set forth in or encoding ESTs AF132025, AF177862, BAB23615, BAA91839, BAB15559, and NP_032190.

A preferred prostate-specific nucleic acid molecule may be preferentially expressed in prostate tissue at a level that is at least 5-fold higher, preferably at least 10-fold higher, more preferably at least 15-fold higher, and most preferably at least 20-fold higher than the level of the same nucleic acid molecule in at least one non-prostate tissue, preferably in all other non-prostate tissues. A prostate-specific nucleic acid molecule can also be expressed at high levels in a non-prostate tissue although, generally, the level of expression will be the highest in the prostate. Occasionally, as described herein, a prostate-specific nucleic acid molecule will be expressed at higher levels in non-prostate tissue (e.g., placenta, lung, or liver) than in the prostate.

A preferred testis-specific nucleic acid molecule may be preferentially expressed in testis tissue at a level that is at least 5-fold higher, preferably at least 10-fold higher, more preferably at least 15-fold higher, and most preferably at least 20-fold higher than the level of the same nucleic acid molecule in at least one non-testis tissue, preferably in all other non-testis tissues. A testis-specific nucleic acid molecule can also be expressed at high levels in a non-testis tissue although, generally, the level of expression will be the highest in the testis. Occasionally, as described herein, a testis-specific nucleic acid molecule will be expressed at higher levels in non-testis tissue (e.g., placenta, lung, or liver) than in the testis.

By "prostate-specific" or a "testis-specific" polypeptide or "prostate-specific" or a "testis-specific" protein is meant a polypeptide that is encoded by a prostate-specific or a testis-specific nucleic acid molecule. A prostate-specific or testis-specific polypeptide may also be defined as a polypeptide having at least 50, 60, or 75%, more preferably at least 80, 85, or 95%, and most preferably at least 99% amino acid identity to the polypeptides described herein, for example, in FIGS. 4, 11, and 14. Specifically excluded from this definition is STEAP (AF186249) (Hubert, R. S. et al., *Proc Natl Acad Sci USA* 96, 14523–14528, 1999) and polypeptide sequences set forth in or encoded by ESTs AF132025, AF177862, BAB23615, BAA91839, BAB15559, and NP_032190. In addition, a polypeptide having at least 50, 60, or 75%, more preferably at least 80, 85, or 95%, and most preferably at least 99% amino acid identity to amino acids 1–200 of STMP1 (SEQ ID NO: 14), preferably amino acids 40–150 of STMP1, can be considered a prostate-specific or testis-specific polypeptide.

A preferred prostate-specific polypeptide is preferentially expressed in prostate tissue at a level that is at least 5-fold higher, preferably at least 10-fold higher, more preferably at least 15-fold higher, and most preferably at least 20-fold higher than the level of the same polypeptide in at least one non-prostate tissue, preferably in all other non-prostate tissues. A prostate-specific polypeptide can also be expressed at high levels in a non-prostate tissue although, generally, the level of expression will be the highest in the prostate. Occasionally, as described herein, a prostate-specific polypeptide will be expressed at higher levels in non-prostate (e.g., placenta, lung, liver) than in the prostate.

A preferred testis-specific polypeptide is preferentially expressed in testis tissue at a level that is at least 5-fold higher, preferably at least 10-fold higher, more preferably at least 15-fold higher, and most preferably at least 20-fold higher than the level of the same polypeptide in at least one non- testis tissue, preferably in all other non-testis tissues. A testis-specific polypeptide can also be expressed at high levels in a non-testis tissue although, generally, the level of expression will be the highest in the testis. Occasionally, as described herein, a testis-specific polypeptide will be expressed at higher levels in non-testis (e.g., placenta, lung, liver) than in the testis.

The term prostate-specific or testis-specific polypeptide includes homologs, analogs, fragments, and isoforms, e.g., alternatively spliced isoforms, of the sequences described herein. By "biologically active fragment" is meant a polypeptide fragment of a prostate-specific or testis-specific polypeptide that exhibits, for example, extracellular trafficking, cell signaling, or other properties that are at least 30%, preferably at least 50%, more preferably at least 75%, and most preferably at least 100%, compared with the properties of a full length prostate-specific or testis-specific polypeptide. By "analog" is meant any substitution, addition, or deletion in the amino acid sequence of a prostate-specific or testis-specific polypeptide that exhibits properties that are at least 30%, preferably at least 50%, more preferably at least 75%, and most preferably at least 100%, compared with the extracellular trafficking or cell signaling properties of the polypeptide from which it is derived. Fragments, homologs, and analogs can be generated using standard techniques, for example, solid phase peptide synthesis or polymerase chain reaction. For example, point mutations may arise at any position of the sequence from an apurinic, apyrimidinic, or otherwise structurally impaired site within the cDNA. Alternatively, point mutations may be introduced by random or site-directed mutagenesis procedures (e.g., oligonucleotide assisted or by error prone PCR). Likewise, deletions and/or insertions may be introduced into the sequences, and preferred insertions comprise 5'- and/or 3'-fusions with a polynucleotide that encodes a reporter moiety or an affinity moiety. Other preferred insertions comprise a nucleic acid that further includes functional elements such as a promoter, enhancer, hormone responsive element, origin of replication, transcription and translation initiation sites, etc. It should be appreciated that where insertions with one or more functional elements are present, the resulting nucleic acid may be linear or circular (e.g., transcription or expression cassettes, plasmids, etc.).

For use in the methods of the invention, the terms "prostate-specific" or "testis-specific" polypeptide further include the polypeptide sequences set forth in or encoded by ESTs AF132025, AF177862, BAB23615, BAA91839, BAB15559, and NP_032190, but does not include STEAP, and a prostate-specific or testis-specific nucleic acid molecule includes the nucleotide sequences set forth in or encoding ESTs AF132025, AF177862, BAB23615, BAA91839, BAB15559, and NP_032190, but does not include STEAP.

By "prostate-specific or a testis-specific gene or homolog or fragment thereof" is meant a gene, or homolog of a gene, that encodes a prostate-specific or testis-specific polypeptide.

By "specifically binds" is meant a compound, e.g., an antibody, that recognizes and binds a protein or polypeptide, for example, a prostate-specific or a testis-specific polypeptide, and that when detectably labeled can be competed away for binding to that protein or polypeptide by an excess of compound that is not detectably labeled. A compound that non-specifically binds is not competed away by excess detectably labeled compound. A preferred antibody binds to any prostate-specific or a testis-specific polypeptide sequence that is substantially identical to any of the polypeptide sequences set forth in FIGS. 4, 11, and 14, or encoded by any of the nucleotide sequences set forth in FIGS. 3, 4, 11, and 14, or portions thereof.

By a "compound," "test compound," or "candidate compound" is meant a molecule, be it naturally-occurring or artificially-derived, and includes, for example, peptides, proteins, synthetic organic molecules, naturally-occurring organic molecules, nucleic acid molecules, and components thereof.

By "high stringency conditions" is meant conditions that allow hybridization comparable with the hybridization that occurs using a DNA probe of at least 500 nucleotides in length, in a buffer containing 0.5 M $NaHPO_4$, pH 7.2, 7% SDS, 1 mM EDTA, and 1% BSA (fraction V), at a temperature of 65° C., or a buffer containing 48% formamide, 4.8×SSC, 0.2 M Tris-Cl, pH 7.6, 1× Denhardt's solution, 10% dextran sulfate, and 0.1% SDS, at a temperature of 42° C. (these are typical conditions for high stringency Northern or Southern hybridizations). High stringency hybridization is also relied upon for the success of numerous techniques routinely performed by molecular biologists, such as high stringency PCR, DNA sequencing, single strand conformational polymorphism analysis, and in situ hybridization. In contrast to Northern and Southern hybridizations, these techniques are usually performed with relatively short probes (e.g., usually 16 nucleotides or longer for PCR or sequencing, and 40 nucleotides or longer for in situ hybridization). The high stringency conditions used in these techniques are well known to those skilled in the art of molecular biology, and may be found, for example, in Ausubel et al., *Current Protocols in Molecular Biology*, John Wiley & Sons, New York, N.Y., 1998, hereby incorporated by reference.

By "probe" or "primer" is meant a single-stranded DNA or RNA molecule of defined sequence that can base pair to a second DNA or RNA molecule that contains a complementary sequence ("target"). The stability of the resulting hybrid depends upon the extent of the base pairing that occurs. This stability is affected by parameters such as the degree of complementarity between the probe and target molecule, and the degree of stringency of the hybridization conditions. The degree of hybridization stringency is affected by parameters such as the temperature, salt concentration, and concentration of organic molecules, such as formamide, and is determined by methods that are well known to those skilled in the art. Probes or primers specific for prostate-specific or a testis-specific nucleic acid molecules, preferably, have greater than 45% sequence identity, more preferably at least 55–75% sequence identity, still more preferably at least 75–85% sequence identity, yet more preferably at least 85–99% sequence identity, and most preferably 100% sequence identity to the nucleic acid sequences encoding the amino acid sequences described herein. Probes can be detectably-labeled, either radioactively or non-radioactively, by methods that are well-known to those skilled in the art. Probes can be used for methods involving nucleic acid hybridization, such as nucleic acid sequencing, nucleic acid amplification by the polymerase chain reaction, single stranded conformational polymorphism (SSCP) analysis, restriction fragment polymorphism (RFLP) analysis, Southern hybridization, northern hybridization, in situ hybridization, electrophoretic mobility shift assay (EMSA), and other methods that are well known to those skilled in the art.

A molecule, e.g., an oligonucleotide probe or primer, a gene or fragment thereof, a cDNA molecule, a polypeptide, or an antibody, can be said to be "detectably-labeled" if it is marked in such a way that its presence can be directly identified in a sample. Methods for detectably-labeling molecules are well known in the art and include, without limitation, radioactive labeling (e.g., with an isotope, such as $^{32}P$ or $^{35}S$) and nonradioactive labeling (e.g., with a fluorescent label, such as fluorescein, or by generating a construct containing green fluorescent protein (GFP)).

By "transgenic" is meant any cell that includes a DNA sequence or transgene that is inserted by artifice into a cell and becomes part of the genome of the organism that develops from that cell. As used herein, the transgenic organisms are generally transgenic mammals (e.g., mice, rats, and goats) and the DNA (transgene) is inserted by artifice into the nuclear genome. By "transgene" is meant any piece of DNA that is inserted by artifice into a cell, and becomes part of the genome of the organism that develops from that cell. Such a transgene may include a gene that is partly or entirely heterologous (i.e., foreign) to the transgenic organism, or may represent a gene homologous to an endogenous gene of the organism. By "knockout mutation" is meant an artificially induced alteration in the nucleic acid sequence (created via recombinant DNA technology or deliberate exposure to a mutagen) that reduces the biological activity of the polypeptide normally encoded therefrom by at least 80% relative to the unmutated gene. The mutation may, without limitation, be an insertion, deletion, frameshift mutation, or a missense mutation. The knockout mutation can be in a cell ex vivo (e.g., a tissue culture cell or a primary cell) or in vivo. A "knockout animal" is a mammal, preferably, a mouse, containing a knockout mutation as defined above.

By "sample" is meant a tissue biopsy, cells, blood, serum, urine, stool, or other specimen obtained from a patient or test subject. The sample is analyzed to detect a mutation in a gene encoding a prostate-specific or a testis-specific polypeptide, or expression levels of a gene encoding a prostate-specific or a testis-specific polypeptide, as for example, an indication of the progression of cancer, by methods that are known in the art or described herein. For example, methods such as sequencing, single-strand conformational polymorphism (SSCP) analysis, or restriction fragment length polymorphism (RFLP) analysis of PCR products derived from a patient sample may be used to detect a mutation in a gene encoding a prostate-specific or a testis-specific polypeptide; ELISA may be used to measure levels of a prostate-specific or a testis-specific polypeptide; and PCR may be used to measure the level of nucleic acids encoding a prostate-specific or a testis-specific polypeptide.

By "pharmaceutically acceptable carrier" is meant a carrier that is physiologically acceptable to the treated mammal while retaining the therapeutic properties of the compound with which it is administered. One exemplary pharmaceutically acceptable carrier is physiological saline solution. Other physiologically acceptable carriers and their formulations are known to one skilled in the art and described, for example, in *Remington: The Science and Practice of Pharmacy*, ($19^{th}$ edition), ed. A. Gennaro, 1995, Mack Publishing Company, Easton, Pa.

"Therapeutically effective amount" as used herein in reference to dosage of a medication, refers to the administration of a specific amount of a pharmacologically active agent (e.g., a prostate-specific or a testis-specific polypeptide, nucleic acid molecule, or modulatory compound) tailored to each individual patient manifesting symptoms characteristic of a specific disorder. For example, a patient receiving the treatment of the present invention might have prostate cancer. A person skilled in the art will recognize that the optimal dose of a pharmaceutical agent to be administered will vary from one individual to another. Dosage in individual patients should take into account the patients height, weight, rate of absorption and metabolism of the medication in question, the stage of the disorder to be treated, and what other pharmacological agents are administered concurrently.

By "treating" or "treatment" is meant the medical management of a patient with the intent to cure, ameliorate, stabilize, or prevent a disease, pathological condition, or disorder. This term includes active treatment, that is, treatment directed specifically toward the improvement or associated with the cure of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. The phrase "treatment" also includes symptomatic treatment, that is, treatment directed toward constitutional symptoms of the associated disease, pathological condition, or disorder.

By "disorder of the prostate or testis" is meant a disturbance of function and/or structure of the prostate or testis in a living organism, resulting from an external source, a genetic predisposition, a physical or chemical trauma, or a combination of the above. Such disorders include the proliferation of prostate or testicular cells. By "cell proliferation" is meant the growth or reproduction of similar cells, and the invention provides reagents for inhibiting proliferation and stimulating proliferation. By "inhibiting proliferation" is meant the decrease in the number of similar cells by at least 10%, more preferably by at least 20%, and most preferably by at least 50%. By "stimulating proliferation" is meant an increase in the number of similar cells by at least 10%, more preferably by at least 20%, and most preferably by at least 50%.

The reagents described herein, for example, vectors expressing antisense, antagonists, or inhibitors of prostate-specific or testis-specific polypeptides or nucleic acid molecules may be used, for example, to suppress the excessive proliferation of prostate or testicular cells. Blocking prostate-specific or testis-specific polypeptide or nucleic acid molecule expression or activity in prostate or testicular cells can alter molecular pathways within cancerous cells and thus trigger apoptosis, i.e., the process of cell death where a dying cell displays a set of well-characterized biochemical hallmarks which include cytolemmal blebbing, cell soma shrinkage, chromatin condensation, and DNA laddering.

Disorders of the prostate or testis include prostate cancer, benign prostatic hyperplasia, acute prostatitis, testicular cancer, developmental defects of the prostate or testis (such as cryptorchidism or undescended testis, and retractile, ascending, or vanished testis).

By "proliferative disease" is meant a disease that is caused by or results in inappropriately high levels of cell division, inappropriately low levels of apoptosis, or both. For example, cancers such as prostate cancer, testicular cancer, lymphoma, leukemia, melanoma, ovarian cancer, breast cancer, pancreatic cancer, liver cancer, and lung cancer are all examples of proliferative disease.

By "modulate" or "modulating" is meant changing, either by decrease or increase, the expression or biological activity of a prostate-specific or testis-specific nucleic acid molecule or polypeptide, as described herein. It will be appreciated that the degree of modulation provided by a modulating compound in a given assay will vary, but that one skilled in the art can determine the statistically significant change in the level of biological activity that identifies a compound that modulates a prostate-specific or testis-specific nucleic acid molecule or polypeptide.

The invention provides several advantages. For example, it provides methods and reagents that can be used in the diagnosis and treatment of prostate and testis associated diseases, as well as other disorders and conditions that are sensitive to the bioactivities of the reagents (e.g., polypeptides, nucleic acid molecules, antibodies) described herein. Since the prostate-specific or testis-specific polypeptides of the invention have been found to be highly expressed in the prostate and testis, these polypeptides can also be used in screens for therapeutics to treat disorders associated with the prostate and testis. These polypeptides are also expressed in other tissues, and can be used as therapeutics and diagnostics for cell proliferative disorders.

Other features and advantages of the invention will be apparent from the detailed description of the invention, the drawings, and the claims.

BRIEF DESCRIPTION OF THE DRAWINGS

FIG. 3 is a table showing the nucleotide sequences of twelve clones (SEQ ID NOs: 1–12) isolated from prostate tissue and LNCaP cells.

FIG. 4B shows the nucleotide sequence, including the intron junction sequences (SEQ ID NO: 13), and predicted amino acid sequence (SEQ ID NO: 14) of STMP1.

FIG. 4C shows the nucleotide sequences of the exons and 3' UTR of STMP1 (SEQ ID NOs: 15–21).

FIG. 4D shows the nucleotide sequence of the ORF of STMP1 (SEQ ID NO: 22).

FIG. 4E shows the shows the cDNA sequence (SEQ ID NO: 23), and predicted amino acid sequence (SEQ ID NO:14) of STMP1.

FIG. 4F shows the nucleotide sequences of the exons and 3' UTR of STMP1 ORF2 (SEQ ID NOs: 17–20 and 24–26).

FIG. 4G shows the nucleotide sequence of the ORF of STMP1 ORF2 (SEQ ID NO: 27).

FIG. 4H shows the cDNA sequence (SEQ ID NO: 28), and predicted amino acid sequence (SEQ ID NO: 29) of STMP1 ORF2.

FIG. 4I shows the nucleotide sequences of the exons and 3' UTR of STMP1 ORF3 (SEQ ID NOs: 17–19 and 24–26).

FIG. 4J shows the nucleotide sequence of the ORF of STMP1 ORF3 (SEQ ID NO: 30).

FIG. 4K shows the cDNA sequence (SEQ ID NO: 31), and predicted amino acid sequence (SEQ ID NO: 32) of STMP1 ORF3.

FIG. 4L shows the cDNA sequence (SEQ ID NO: 33), and predicted amino acid sequence (SEQ ID NO:34) of STMP2.

FIG. 4M shows the cDNA sequence (SEQ ID NO: 35), and predicted amino acid sequence (SEQ ID NO: 36) of STMP3.

FIG. 5 shows a sequence alignment of STMP1 (SEQ ID NO: 14), with STEAP (SEQ ID NO: 37, Accession No. AF186249), and two ESTs (Accession No. BAA91839 and Accession No. BAB15559; SEQ ID NOs: 38 and 39, respectively).

FIG. 11A shows the cDNA (SEQ ID NO: 40) and predicted amino acid sequence (SEQ ID NO: 41) for SSH9.

FIG. 11B shows the predicted promoter sequence for SSH9 (SEQ ID NO: 42).

FIG. 11C shows the predicted intron-exon boundaries for SSH9 (SEQ ID NOs: 43–50).

FIG. 14A shows the nucleotide sequence of the ORF of PSL22 (SEQ ID NO: 51).

FIG. 14B shows the cDNA sequence (SEQ ID NO: 52), and predicted amino acid sequence (SEQ ID NO: 53) of PSL22.

FIG. 14C shows the nucleotide sequences of the TATA promoter and transcription start site, exons, and 5' and 3' UTRs of PSL22 (SEQ ID NOs: 54–70).

DETAILED DESCRIPTION OF THE INVENTION

Figure 1:
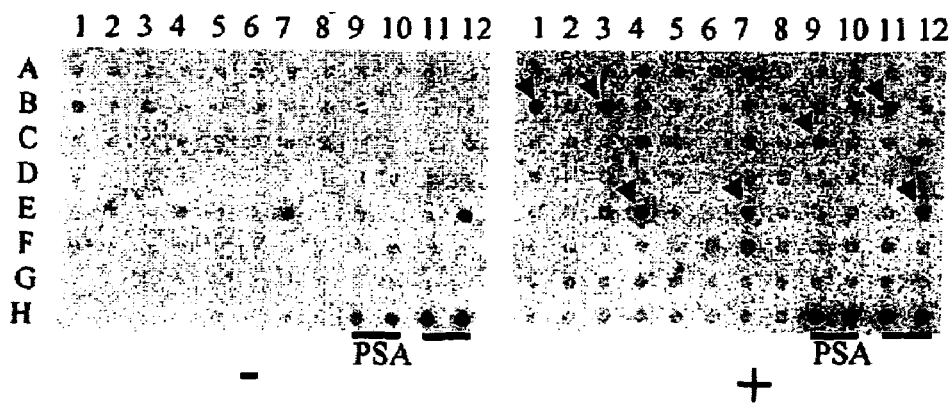
FIG. 1 shows an exemplary reverse northern analysis of several clones from a prostate specific cDNA library.

The basic biology of the normal prostate and testis, as well as prostate and testicular cancer initiation and progression is still poorly understood. It is therefore necessary to delineate the molecular events that are at the basis of these processes. To achieve this goal, we have identified, cloned, and characterized highly prostate- and testis-enriched genes whose gene products have important roles for both the normal physiology and the pathophysiology of the prostate and the testis. These gene products also have important roles in other disorders, for example, heart, brain, liver, pancreas, kidney, and colon, which are the tissues where variable low expression, and occasionally, very high expression of specific gene products, can be detected by Northern analysis.

The invention provides prostate-specific or testis-specific polypeptides and nucleic acid molecules (see below), and diagnostic and therapeutic methods employing these polypeptides and nucleic acid molecules. The invention also provides methods for identifying compounds that modulate the biological activities of prostate-specific or testis-specific polypeptides and nucleic acid molecules, and therapeutic methods employing these compounds. The diagnostic, therapeutic, and screening methods of the invention are first described, followed by general approaches that can be used in carrying out these methods. Finally, experimental results supporting the methods of the invention are described.

Bioassays

Prostate-specific and testis-specific polypeptides are expressed in the prostate and testis, and also in other tissues such as kidney, pancreas, liver, lung, and colon. The expression patterns of prostate-specific and testis-specific polypeptides in specific cells and tissues are used to identify cellular targets of prostate-specific and testis-specific polypeptide actions, and to identify bioactivities that are relevant to specific prostate- and testis-related diseases, such as prostate cancer, testicular cancer, benign prostatic hyperplasia, acute prostatitis, and developmental testis defects.

Therapeutic and diagnostic utilities for prostate-specific and testis-specific polypeptides are identified by, for example, conducting bioassays in vitro. Culture systems that reflect prostate-specific and testis-specific polypeptide expression patterns, along with the distribution of particular receptors, such as the androgen receptor, are selected. For example, LNCaP cells express androgen receptors, and respond to one or more isoforms of prostate-specific and testis-specific polypeptides in a variety of bioassays. The activities of prostate-specific and testis-specific polypeptides (e.g., STMP1, SSH9, PSL22) are compared, using sister cultures, in various dose-response assays, including but not limited to, inhibition of proliferation, apoptosis, signaling events (e.g. changes in kinase activity), changes in transcription factor activity (such as that of the androgen receptor), intracellular trafficking, or cell signaling. The relative potencies of the prostate-specific and testis-specific polypeptides are determined on the basis of, for example, protein concentration.

Diagnostic Methods Employing Prostate-Specific Or Testis-Specific Nucleic Acid Molecules, Polypeptides and Antibodies Prostate-specific or testis-specific nucleic acid molecules, polypeptides, and antibodies are used in methods to diagnose or monitor a variety of diseases and conditions, including those involving mutations in, or inappropriate expression of, prostate-specific or testis-specific genes. Prostate-specific or testis-specific expression has been documented in a variety of tissues, as discussed above. Thus, detection of abnormalities in prostate-specific or testis-specific genes or their expression is used in methods to diagnose, or to monitor treatment or development of diseases of these tissues.

The diagnostic methods of the invention are used, for example, with patients that have a prostate-related or testis-related disease, for example, prostate or testicular cancer, in an effort to determine its etiology, and thus, to facilitate selection of an appropriate course of treatment. The diagnostic methods are also used with patients that have not yet developed a prostate-related or testis-related disease, but who may be at risk of developing such a disease, or with patients that are at an early stage of developing such a disease. Many prostate-related or testis-related diseases occur during development, and thus, the diagnostic methods of the invention are also carried out on a fetus or embryo during development. Also, the diagnostic methods of the invention are used in prenatal genetic screening, for example, to identify parents who may be carriers of a recessive prostate-related or testis-related mutation.

Prostate-specific or testis-specific abnormalities that are detected using the diagnostic methods of the invention include those characterized by, for example, (i) abnormal prostate-specific or testis-specific polypeptides, (ii) prostate-specific or testis-specific genes containing mutations that result in the production of such polypeptides, and (iii) mutations that result in production of abnormal amounts of prostate-specific or testis-specific polypeptides.

Levels of prostate-specific or testis-specific expression in a patient sample are determined by using any of a number of standard techniques that are well known in the art. For example, prostate-specific or testis-specific expression in a biological sample (e.g. a blood, prostate or testis tissue sample, or amniotic fluid) from a patient is monitored by standard northern blot analysis or by quantitative PCR (see, e.g., Ausubel et al., *Current Protocols in Molecular Biology*, John Wiley & Sons, New York, N.Y., 1998; *PCR Technology: Principles and Applications for DNA Amplification*, H. A. Ehrlich, Ed., Stockton Press, NY; Yap et al. *Nucl. Acids. Res.* 19:4294, 1991).

A biological sample obtained from a patient can be analyzed for one or more mutations in prostate-specific or testis-specific nucleic acid molecules using a mismatch detection approach. Generally, this approach involves PCR amplification of nucleic acid molecules from a patient sample, followed by identification of a mutation (i.e., a mismatch) by detection of altered hybridization, aberrant electrophoretic gel migration, binding, or cleavage mediated by mismatch binding proteins, or by direct nucleic acid molecule sequencing. Any of these techniques can be used to facilitate detection of mutant prostate-specific or testis-specific genes, and each is well known in the art. Examples of these techniques are described, for example, by Orita et al. (*Proc. Natl. Acad. Sci. USA* 86:2766–2770, 1989) and Sheffield et al. (*Proc. Natl Acad. Sci. USA* 86:232–236, 1989).

Mismatch detection assays also provide an opportunity to diagnose a prostate-specific or testis-specific gene-mediated predisposition to a disease before the onset of symptoms. For example, a patient heterozygous for a prostate-specific or testis-specific mutation that suppresses normal prostate-specific or testis-specific biological activity or expression may show no clinical symptoms of a prostate-specific or testis-specific gene-related disease, and yet possess a higher than normal probability of developing a prostate or testicular disease. Given such a diagnosis, patients can take precautions to minimize their exposure their exposure to adverse environmental factors and to carefully monitor their medical condition (for example, through frequent physical examinations). As mentioned above, this type of diagnostic approach can also be used to detect prostate-specific or testis-specific mutations in prenatal screens.

The prostate-specific or testis-specific diagnostic assays described above can be carried out using any biological sample (for example, a blood, prostate, or testis tissue sample, or amniotic fluid) in which a prostate-specific or testis-specific polypeptide or nucleic acid molecule is normally expressed. A mutant prostate-specific or testis-specific gene can also be identified using these sources as test samples. Alternatively, a prostate-specific or testis-specific mutation, as part of a diagnosis for predisposition to a prostate-specific or testis-specific gene-associated disease, can be tested for using a DNA sample from any cell, for example, by mismatch detection techniques. Preferably, the DNA sample is subjected to PCR amplification prior to analysis.

In yet another diagnostic approach of the invention, an immunoassay is used to detect or monitor prostate-specific or testis-specific protein expression in a biological sample. Anti-prostate-specific or testis-specific-polypeptide polyclonal or monoclonal antibodies (as described below) can be used in any standard immunoassay format (e.g., ELISA, Western blot, or RIA; see, e.g., Ausubel et al., supra) to measure prostate-specific or testis-specific polypeptide levels. These levels are compared to wild-type prostate-specific or testis-specific levels. For example, an increase in prostate-specific or testis-specific polypeptide production may be indicative of a condition or a predisposition to a condition involving overexpression of prostate-specific or testis-specific polypeptide biological activity, such as late stage prostate cancer.

Immunohistochemical techniques can also be utilized for prostate-specific or testis-specific polypeptide detection. For example, a tissue sample can be obtained from a patient, sectioned, and stained for the presence of prostate-specific or testis-specific polypeptide using an anti-prostate-specific or testis-specific antibody (see below) and any standard detection system (e.g., one that includes a secondary antibody conjugated to horseradish peroxidase). General guidance regarding such techniques can be found in, e.g., Bancroft et al., *Theory and Practice of Histological Techniques*, Churchill Livingstone, 1982, and Ausubel et al., supra.

In a preferred example, a combined diagnostic method can be employed that includes an evaluation of prostate-specific or testis-specific protein production (for example, by immunological techniques or the protein truncation test (Hogerrorst et al., *Nature Genetics* 10:208–212, 1995), and a nucleic acid molecule-based detection technique designed to identify more subtle prostate-specific or testis-specific mutations (for example, point mutations). As described above, a number of mismatch detection assays are available to those skilled in the art, and any preferred technique can be used. Mutations in prostate-specific or testis-specific genes can be detected that either result in loss or gain of prostate-specific or testis-specific polypeptide or nucleic acid molecule expression or loss or gain of normal prostate-specific or testis-specific polypeptide or nucleic acid molecule biological activity.

Prostate-specific or testis-specific polypeptides or nucleic acid molecules can be used to correlate the course of prostate cancer to a marker other than PSA, to monitor the course of an anticancer therapy, or to detect a neoplastic cell in a system. For example, a predetermined quantity of an RNA encoding a prostate-specific or testis-specific polypeptide is correlated with the presence of a neoplastic cell, for example, from a biopsy. The total RNA is extracted from the biopsy specimen, and a real time quantitative rt-PCR employing individual reactions with primer pairs specific to prostate-specific or testis-specific sequences is performed in parallel with a biopsy specimen known to be free of cancer cells. Biopsy specimens are determined to have a cancer cell, where the detected prostate-specific or testis-specific mRNA quantity is at least 5 times higher than in the control specimen. An exemplary extraction of total RNA utilizes the Quiagen BioRobot kit in conjunction with the BioRobot 9600 system, and the real time rtPCR is performed in a Perkin Elmer ABI Prism 7700.

In alternative aspects of the inventive subject matter, the method of detecting a neoplastic cell need not be limited to biopsy tissues from prostate or testis tissue, but may employ various alternative tissues, including lymphoma tumor cells, and various solid tumor cells, so long as such tumor cells overproduce mRNA of prostate-specific or testis-specific polypeptides. Appropriate alternative tumor cells can readily be identified by the above described method. Likewise, the system need not be restricted to a mammal, but may also include cell-, and tissue cultures grown in vitro, and tumor cells and specimens from animals other than mammals. For example, tumor cell and tissue grown in vitro may advantageously be utilized to investigate drug action on such cells, and sequences encoding prostate-specific or testis-specific polypeptides may conveniently be employed as tumor marker. Alternatively, body fluids (e.g., serum, saliva, etc.) that may or may not contain tumor cells are also contemplated a suitable substrate for the method presented herein, so long as they contain to at least some extent mRNA encoding a prostate-specific or testis-specific polypeptide.

In still other aspects of contemplated methods, the polypeptide quantity need not necessarily be limited to at least 5 times more than the control specimen in order to establish that the tissue has a cancer cell. For example, where the concentration of the polypeptide is hormone dependent, amounts between 3–8 fold and more may be appropriate. In contrast, where the concentration of cancer cells in the biopsy specimen is relatively low, amounts of less than 5-fold, including 1.5 to 4.9-fold and less are contemplated.

The detection process may include fluorescence detection, luminescence detection, scintigraphy, autoradiography, and formation of a dye. For example, for microscopic analysis of biopsy specimens, luciferase labeled probes are particularly advantageous in conjunction with a luminescence substrate (e.g., luciferin). Luminescence quantification may then be performed utilizing a CCD-camera and image analysis system. Similarly, radioactivity may be detected via autoradiographic or scintigraphic procedures on a tissue section, in a fluid or on a solid support. Where the probe is a natural or synthetic ligand of a prostate-specific or testis-specific polypeptide, the ligand may include molecules with a chemical modification that increase the affinity to the polypeptide and/or induce irreversible binding to the polypeptide. For example, transition state analogs or suicide inhibitors for a particular reaction catalyzed by the polypeptide are especially contemplated. Labeling of antibodies, antibody fragments, small molecules, and binding of the labeled entity is a technique that is well known in the art, and all known methods are generally suitable for use in conjunction with methods contemplated herein. Furthermore, the probe need not be limited to a fluorescein labeled antibody, and alternative probes include antibody fragments (e.g., Fab, Fab', scFab, etc.).

Still further contemplated variations include substitution of one or more atoms or chemical groups in the sequence with a radioactive atom or group. For example, where cDNAs are employed as a hybridization-specific probes, a fluorophor or enzyme (e.g., β-galactosidase for generation of a dye, or luciferase for generation of luminescence) may be coupled to the sequence to identify position and/or quantity of a complementary sequence. Alternatively, where contemplated cDNA molecules are utilized for affinity isolation procedures, the cDNA may be coupled to a molecule that is known to have a high-affinity (i.e., $K_d<10^{-4}$ mol$^{-1}$) partner, such as biotin, or an oligo-histidyl tag. In another example, one or more phosphate groups may be exchanged for a radioactive phosphate group with a $^{32}$P or $^{33}$P isotope to assist in detection and quantification, where the radiolabeled cDNA is employed as a hybridization probe.

Therapeutic Methods Employing Prostate-Specific or Testis-Specific Nucleic Acid Molecules Polypeptides, and Antibodies The invention includes methods of treating or preventing prostate-specific or testis-specific diseases. Therapies are designed to circumvent or overcome a prostate-specific or testis-specific gene defect, or inadequate or excessive prostate-specific or testis-specific gene expression, and thus modulate and possibly alleviate conditions involving defects in prostate-specific or testis-specific genes or proteins. In considering various therapies, it is understood that such therapies are, preferably, targeted to the affected or potentially affected organs, for example, the prostate or the testis. Reagents that are used to modulate prostate-specific or testis-specific biological activity can include, without limitation, full length prostate-specific or testis-specific polypeptides; prostate-specific or testis-specific cDNA, mRNA, or antisense RNA; prostate-specific or testis-specific antibodies; and any compound that modulates prostate-specific or testis-specific polypeptide or nucleic acid molecule biological activity, expression, or stability.

Treatment or prevention of diseases resulting from a mutated prostate-specific or testis-specific gene is accomplished, for example, by replacing a mutant prostate-specific or testis-specific gene with a normal prostate-specific or testis-specific gene, administering a normal prostate-specific or testis-specific gene, modulating the function of a mutant prostate-specific or testis-specific protein, delivering normal prostate-specific or testis-specific protein to the appropriate cells, or altering the levels of normal or mutant prostate-specific or testis-specific protein. It is also possible to correct a prostate-specific or testis-specific gene defect to modify the physiological pathway (e.g., an intracellular trafficking pathway) in which the prostate-specific or testis-specific protein participates.

To replace a mutant protein with normal protein, or to add protein to cells that do not express sufficient or normal prostate-specific or testis-specific protein, it may be necessary to obtain large amounts of pure prostate-specific or testis-specific protein from cultured cell systems in which the protein is expressed (see, e.g., below). Delivery of the protein to the affected tissue can then be accomplished using appropriate packaging or administrating systems. Alternatively, small molecule analogs that act as prostate-specific or testis-specific molecule agonists or antagonists can be administered to produce a desired physiological effect (see below).

Gene therapy is another therapeutic approach for preventing or ameliorating diseases caused by prostate-specific or testis-specific gene defects. Nucleic acid molecules encoding wild type prostate-specific or testis-specific proteins can be delivered to cells that lack sufficient, normal prostate-specific or testis-specific biological activity (e.g. cells carrying mutations in prostate-specific or testis-specific genes). The nucleic acid molecules must be delivered to those cells in a form in which they can be taken up by the cells and so that sufficient levels of protein, to provide effective prostate-specific or testis-specific function, can be produced. Alternatively, for some prostate-specific or testis-specific mutations, it may be possible slow the progression of the resulting disease or to modulate prostate-specific or testis-specific activity by introducing another copy of a homologous gene bearing a second mutation in that gene, to alter the mutation, or to use another gene to block any negative effect.

Transducing retroviral, adenoviral, and adeno-associated viral vectors can be used for somatic cell gene therapy, especially because of their high efficiency of infection and stable integration and expression (see, e.g., Cayouette et al., *Human Gene Therapy* 8:423–430, 1997; Kido et al., *Current Eye Research* 15:833–844, 1996; Bloomer et al., *Journal of Virology* 71:6641–6649, 1997; Naldini et al., *Science* 272: 263–267, 1996; and Miyoshi et al., *Proc. Natl. Acad. Sci., USA* 94:10319–1032, 1997). For example, the full length prostate-specific or testis-specific gene, or a portion thereof, can be cloned into a retroviral vector and expression can be driven from its endogenous promoter, from the retroviral long terminal repeat, or from a promoter specific for a target cell type of interest (such as aortic or other vascular cells). Other viral vectors that can be used include, for example, vaccinia virus, bovine papilloma virus, or a herpes virus, such as Epstein-Barr Virus (also see, for example, the vectors of Miller, *Human Gene Therapy* 15–14, 1990; Friedman, *Science* 244:1275–1281, 1989; Eglitis et al, *Bio-Techniques* 6:608–614, 1988; Tolstoshev et al., *Current Opinion in Biotechnology* 1:55–61, 1990; Sharp, *The Lancet* 337:1277–1278, 1991; Cornetta et al., *Nucleic Acid Research and Molecular Biology* 36:311–322, 1987; Anderson, *Science* 226:401–409, 1984; Moen, *Blood Cells* 17:407–416, 1991; or Miller et al., *Biotechnology* 7:980–990, 1989). Retroviral vectors are particularly well developed and have been used in clinical settings (Rosenberg et al., *N. Engl. J. Med* 323:370, 1990; Anderson et al., U.S. Pat. No. 5,399,346).

Gene transfer can also be achieved using non-viral means involving transfection in vitro, by means of any standard technique, including but not limited to, calcium phosphate, DEAE dextran, electroporation, protoplast fusion, and liposomes. Transplantation of normal genes into the affected tissues of a patient can also be accomplished by transferring a normal prostate-specific or testis-specific gene into a cultivatable cell type ex vivo, after which the cell (or its descendants) is injected into a targeted tissue. Another strategy for inhibiting prostate-specific or testis-specific function using gene therapy involves intracellular expression of an anti-prostate-specific or testis-specific antibody or a portion of an prostate-specific or testis-specific antibody. For example, the gene (or gene fragment) encoding a monoclonal antibody that specifically binds to prostate-specific or testis-specific polypeptide and inhibits its biological activity is placed under the transcriptional control of a tissue-specific gene regulatory sequence. Another therapeutic approach involves administration of recombinant prostate-specific or testis-specific polypeptide, either directly to the site of a potential or actual disease-affected tissue (for example, by injection) or systemically (for example, by any conventional recombinant protein administration technique). The dosage of a prostate-specific or testis-specific polypeptide depends on a number of factors, including the size and health of the individual patient but, generally, between about 0.006 mg/kg to about 0.6 mg/kg, inclusive, is administered per day to an adult in any pharmaceutically acceptable formulation.

Non-viral approaches can also be employed for the introduction of therapeutic DNA into cells predicted to be subject to diseases involving a prostate-specific or testis-specific disorder. For example, a prostate-specific or testis-specific nucleic acid molecule or an antisense nucleic acid molecule can be introduced into a cell by lipofection (Felgner et al., *Proc. Natl. Acad. Sci. USA* 84:7413, 1987; Ono et al., *Neuroscience Letters* 17:259, 1990; Brigham et al., *Am. J. Med. Sci.* 298:278, 1989; Staubinger et al., *Methods in Enzymology* 101:512, 1983), asialoorosomucoid-polylysine conjugation (Wu et al., *Journal of Biological Chemistry* 263:14621, 1988; Wu et al., *Journal of Biological Chemistry* 264:16985, 1989), or, less preferably, micro-injection under surgical conditions (Wolff et al., *Science* 247:1465, 1990).

Prostate-specific or testis-specific cDNA expression for use in gene therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct prostate-specific or testis-specific expression. The enhancers used can include, without limitation, those that are characterized as tissue- or cell-specific enhancers. Alternatively, if a prostate-specific or testis-specific genomic clone is used as a therapeutic construct (such clones can be identified by hybridization with prostate-specific or testis-specific cDNA, described above), regulation can be mediated by the cognate regulatory sequences, or, if desired, by regulatory sequences derived from a heterologous source, including any of the promoters or regulatory elements described above.

Antisense-based strategies can be employed to explore prostate-specific or testis-specific gene function and as a basis for therapeutic drug design. These strategies are based on the principle that sequence-specific suppression of gene expression (via transcription or translation) can be achieved by intracellular hybridization between genomic DNA or mRNA and a complementary antisense species. The formation of a hybrid RNA duplex interferes with transcription of the target prostate-specific or testis-specific-encoding genomic DNA molecule, or processing, transport, translation, or stability of the target prostate-specific or testis-specific mRNA molecule.

Antisense strategies can be delivered by a variety of approaches. For example, antisense oligonucleotides or antisense RNA can be directly administered (e.g., by intravenous injection) to a subject in a form that allows uptake into cells. Alternatively, viral or plasmid vectors that encode antisense RNA (or antisense RNA fragments) can be introduced into a cell in vivo or ex vivo. Antisense effects can be induced by control (sense) sequences; however, the extent of phenotypic changes are highly variable. Phenotypic effects induced by antisense effects are based on changes in criteria such as protein levels, protein activity measurement, and target mRNA levels.

For example, prostate-specific or testis-specific gene therapy can also be accomplished by direct administration of antisense prostate-specific or testis-specific mRNA to a cell that is expected to be adversely affected by the expression of wild-type or mutant prostate-specific or testis-specific polypeptides. The antisense prostate-specific or testis-specific mRNA can be produced and isolated by any standard technique, but is most readily produced by in vitro transcription using an antisense prostate-specific or testis-specific cDNA under the control of a high efficiency promoter (e.g., the T7 promoter). Administration of antisense prostate-specific or testis-specific mRNA to cells can be carried out by any of the methods for direct nucleic acid molecule administration described above.

An alternative strategy for inhibiting prostate-specific or testis-specific function using gene therapy involves intracellular expression of an anti-prostate-specific or testis-specific antibody or a portion of an anti-prostate-specific or testis-specific antibody. For example, the gene (or gene fragment) encoding a monoclonal antibody that specifically binds to prostate-specific or testis-specific and inhibits its biological activity can be placed under the transcriptional control of a tissue-specific gene regulatory sequence.

Another therapeutic approach within the invention involves administration of recombinant prostate-specific or testis-specific polypeptide, either directly to the site of a potential or actual disease-affected tissue (for example, by injection) or systemically (for example, by any conventional recombinant protein administration technique). The dosage of prostate-specific or testis-specific depends on a number of factors, including the size and health of the individual patient, but, generally, between 0.1 mg and 100 mg, inclusive, are administered per day to an adult in any pharmaceutically acceptable formulation.

In a patient diagnosed as having a prostate-specific or testis-specific mutation gene or a prostate-specific or testis-specific disease, or as susceptible to prostate-specific or testis-specific gene mutations, aberrant prostate-specific or testis-specific polypeptide or nucleic acid molecule expression (even if those mutations or expression patterns do not yet result in alterations in prostate-specific or testis-specific expression or biological activity), or to a prostate-specific or testis-specific disease, any of the above-described therapies are administered before the occurrence of the disease phenotype. Also, compounds shown to modulate prostate-specific or testis-specific polypeptide or nucleic acid molecule expression or prostate-specific or testis-specific polypeptide or nucleic acid molecule biological activity are administered to patients diagnosed with potential or actual diseases by any standard dosage and route of administration. Alternatively, gene therapy using an antisense prostate-specific or testis-specific mRNA expression construct is undertaken to reverse or prevent the gene defect prior to the development of the full course of the disease.

The therapeutic methods of the invention are, in some cases, targeted to prenatal treatment. For example, a fetus found to have a prostate-specific or testis-specific mutation is administered a gene therapy vector including a normal prostate-specific or testis-specific gene, or administered a normal prostate-specific or testis-specific protein. Such treatment may be required only for a short period of time, or may, in some form, be required throughout such a patient's lifetime. Any continued need for treatment, however, is determined using, for example, the diagnostic methods described above. Also as discussed above, prostate-specific or testis-specific polypeptide or nucleic acid molecule abnormalities may be associated with diseases in adults, and thus, adults are subject to the therapeutic methods of the invention as well.

Additionally, prostate-specific or testis-specific polypeptides may be used to stimulate an immune system to assist in generating immunity against, for example, prostate cancer cells.

The methods of the present invention can be used to diagnose or treat the disorders described herein in any mammal, for example, humans, domestic pets, or livestock. Where a non-human mammal is treated or diagnosed, the prostate-specific or testis-specific polypeptide, nucleic acid molecule, or antibody employed is preferably specific for that species.

Identification of Molecules that Modulate Prostate-Specific Or Testis-Specific Polypeptide or Nucleic Acid Molecule Biological Activity or Whose Biological Activity is Modulated by Prostate-Specific Or Testis-Specific Polypeptides or Nucleic Acid Molecules Isolation of prostate-specific or testis-specific cDNAs (as described herein) also facilitates the identification of molecules that increase or decrease prostate-specific or testis-specific polypeptide or nucleic acid molecule biological activity. Similarly, molecules whose activity is modulated by prostate-specific or testis-specific polypeptide or nucleic acid molecule biological activity can be identified. According to one approach, candidate molecules are added at varying concentrations to the culture medium of cells expressing prostate-specific or testis-specific mRNA. Prostate-specific or testis-specific biological activity is then measured using standard techniques. The measurement of biological activity can include, without limitation, the measurement of prostate-specific or testis-specific protein and nucleic acid molecule expression levels, response to androgens, or intracellular localization and trafficking.

If desired, the effect of candidate modulators on expression can also be measured at the level of prostate-specific or testis-specific protein production using the same general approach and standard immunological detection techniques, such as western blotting or immunoprecipitation with a prostate-specific or testis-specific-specific antibody (see below).

A test compound that is screened in the methods described above can be a chemical, be it naturally-occurring or artificially-derived. Such compounds can include, for example, polypeptides, synthesized organic molecules, naturally occurring organic molecules, nucleic acid molecules, and components thereof Candidate prostate-specific or testis-specific modulators include peptide as well as non-peptide molecules (e.g., peptide or non-peptide molecules found, e.g., in a cell extract, mammalian serum, or growth medium in which mammalian cells have been cultured).

Administration of Prostate-Specific or Testis-Specific Polypeptides, Prostate-Specific or Testis-Specific Nucleic Acid Molecules, and Modulators of Prostate-Specific or Testis-Specific Polypeptide or Nucleic Acid Molecule Synthesis or Function A prostate-specific or testis-specific protein, nucleic acid molecule, or modulator is administered within a pharmaceutically-acceptable diluent, carrier, or excipient, in unit dosage form to patients or experimental animals. Also, conventional pharmaceutical practice is employed to provide suitable formulations or compositions in which to administer neutralizing prostate-specific or testis-specific antibodies or prostate-specific or testis-specific-inhibiting compounds (e.g., a prostate-specific or testis-specific antisense molecule or a prostate-specific or testis-specific dominant negative mutant) to patients suffering from a prostate-specific or testis-specific disease, such as prostate cancer, testicular cancer, benign hyperplasia of the prostate, or developmental defects of the prostate or testis. Administration can begin before or after the patient is symptomatic.

Any appropriate route of administration can be employed, for example, administration can be parenteral, intravenous, intra-arterial, subcutaneous, intramuscular, intracranial, intraorbital, ophthalmic, intraventricular, intracapsular, intraspinal, intracisternal, intraperitoneal, intranasal, inhalation to deep lung, aerosol, by suppositories, oral, or topical (e.g. by applying an adhesive patch carrying a formulation capable of crossing the dermis and entering the bloodstream). Preferably, the administration is local to the afflicted tissue, such as prostate or testis tissue. Therapeutic formulations can be in the form of liquid solutions or suspensions; for oral administration, formulations can be in the form of tablets or capsules; and for intranasal formulations, in the form of powders, nasal drops, or aerosols. Any of the above formulations may be a sustained-release formulation.

Methods that are well known in the art for making formulations are found, for example, in *Remington's Pharmaceutical Sciences*, ($18^{th}$ edition), ed. A. Gennaro, 1990, Mack Publishing Company, Easton, Pa. Formulations for parenteral administration can, for example, contain excipients; sterile water; or saline; polyalkylene glycols, such as polyethylene glycol; oils of vegetable origin; or hydrogenated napthalenes. Sustained-release, biocompatible, biodegradable lactide polymer, lactide/glycolide copolymer, or polyoxyethylene-polyoxypropylene copolymers can be used to control the release of the compounds. Other potentially useful parenteral delivery systems for prostate-specific or testis-specific modulatory compounds include ethylene-vinyl acetate copolymer particles, osmotic pumps, implantable infusion systems, and liposomes. Formulations for inhalation can contain excipients, for example, lactose, or can be aqueous solutions containing, for example, polyoxyethylene-9-lauryl ether, glycocholate, and deoxycholate, or can be oily solutions for administration in the form of nasal drops, or as a gel.

Prostate-Specific or Testis-Specific Fragments

Polypeptide fragments that include various portions of prostate-specific or testis-specific proteins are useful in identifying the domains important for their biological activities, such as protein-protein interactions and transcription. Methods for generating such fragments are well known in the art (see, for example, Ausubel et al., supra), using the nucleotide sequences provided herein. For example, a prostate-specific or testis-specific protein fragment can be generated by PCR amplifying a desired prostate-specific or testis-specific nucleic acid molecule fragment using oligonucleotide primers designed based upon the prostate-specific or testis-specific nucleic acid sequences. Preferably, the oligonucleotide primers include unique restriction enzyme sites that facilitate insertion of the amplified fragment into the cloning site of an expression vector (e.g., a mammalian expression vecoor, see above). This vector can then be introduced into a cell (e.g., a mammalian cell; see above) by artifice, using any of the various techniques known in the art such as those described herein, resulting in the production of a prostate-specific or testis-specific polypeptide fragment in the cell containing the expression vector.

Prostate-specific or testis-specific polypeptide fragments (e.g., chimeric fusion proteins) can also be used to raise antibodies specific for various regions of prostate-specific or testis-specific polypeptides. Preferred prostate-specific or testis-specific fragments include, without limitation, fragments including the N-terminal domain of STMP1 (amino acids 1–200), the P5CR domain, and fragments thereof.

Synthesis of Prostate-Specific or Testis-Specific Proteins, Polypeptides, and Polypeptide Fragments Those skilled in the art of molecular biology will understand that a wide variety of expression systems can be used to produce recombinant prostate-specific or testis-specific proteins. The precise host cell used is not critical to the invention. The prostate-specific or testis-specific proteins can be produced in a prokaryotic host (e.g., *E. coli*) or in a eukaryotic host (e.g., *S. cerevisiae*, insect cells such as Sf9 cells, or mammalian cells such as COS, NIH 3T3, CHO, or HeLa cells). These cells are commercially available from, for example, the American Type Culture Collection, Rockville, Md. (see also Ausubel et al., *Current Protocols in Molecular Biology*, John Wiley & Sons, New York, N.Y., 1998). The method of transformation and the choice of expression vehicle (e.g., expression vector) will depend on the host system selected. Transformation and transfection methods are described, e.g., in Ausubel et al., *Current Protocols in Molecular Biology*, John Wiley & Sons, New York, N.Y., 1998, and expression vehicles can be chosen from those provided, e.g. in Pouwels et al., *Cloning Vectors: A Laboratory Manual*, 1985, Supp. 1987).

The characteristics of prostate-specific or testis-specific nucleic acid molecules are analyzed by introducing such genes into various cell types or using in vitro extracellular systems. The function of prostate-specific or testis-specific proteins produced in such cells or systems are then examined under different physiological conditions. Also, cell lines can be produced that over-express the prostate-specific or testis-specific gene product, allowing purification of prostate-specific or testis-specific proteins for biochemical characterization, large-scale production, antibody production, and patient therapy.

The polypeptides of the invention may be produced in vivo or in vitro, and may be chemically and/or enzymatically modified. The polypeptides can be isolated from prostate tissue or prostate cancer cells that may or may not be in a hormone dependent state. Alternatively, and especially where larger amounts (i.e., >10 mg) are desirable, recombinant production (e.g., in a bacterial, yeast, insect cell, or mammalian cell system) may advantageously be employed to generate significant quantities of prostate-specific or testis-specific polypeptides.

Furthermore, recombinant production not only offers a more economical strategy to produce the polypeptides of the invention, but also allows specific modification in the amino acid sequence and composition to tailor particular biochemical, catalytic and physical properties. For example, where increased solubility of is desirable, one or more hydrophobic amino acids may be replaced with hydrophilic amino acids. Alternatively, where reduced or increased catalytic activity is required, one or more amino acids may be replaced or eliminated.

In still another example, the polypeptides of the invention can be synthesized as fusion proteins including, for example, fusions with enzymatically active partners (e.g., for dye formation or substrate conversion) and fluorescent partners such as GFP, EGFB, BFP, etc.

With respect to chemical and enzymatic modifications of contemplated polypeptides, it is many modifications are appropriate, including addition of mono-, and bifunctional linkers, coupling with protein- and non-protein macromolecules, and glycosylation. For example, mono- and bifunctional linkers are especially advantageous where polypeptides are immobilized to a solid support, or covalently coupled to a molecule that enhances immunogenicity of contemplated polypeptides (e.g., KLH, or BSA conjugation). Alternatively, the polypeptides may be coupled to antibodies or antibody fragments to allow rapid retrieval of the polypeptide from a mixture of molecules. Further couplings include covalent and non-covalent coupling of polypeptides with molecules that prolong the serum half-life and/or reduce immunogenicity such as cyclodextranes and polyethylene glycols.

Use of Prostate-Specific or Testis-Specific Antibodies

Antibodies to prostate-specific or testis-specific proteins are used to detect prostate-specific or testis-specific proteins or to inhibit the biological activities of prostate-specific or testis-specific proteins. For example, a nucleic acid molecule encoding an antibody or portion of an antibody can be expressed within a cell to inhibit prostate-specific or testis-specific function. In addition, the antibodies can be coupled to compounds, such as radionuclides and liposomes for diagnostic or therapeutic uses. Antibodies that inhibit the activity of a prostate-specific or testis-specific polypeptide can also be useful in preventing or slowing the development of a disease caused by inappropriate expression of a wild type or mutant prostate-specific or testis-specific gene. For example, the antibodies of the invention may be utilized to localize and locally quantify disease-specific markers in prostate or testis tissue sections, e.g, in prostate or testicular cancer.

Detection of Prostate-Specific or Testis-Specific Gene Expression

As noted, the antibodies described above can be used to monitor prostate-specific or testis-specific protein expression. In situ hybridization of RNA can be used to detect the expression of prostate-specific or testis-specific genes. RNA in situ hybridization techniques rely upon the hybridization of a specifically labeled nucleic acid probe to the cellular RNA in individual cells or tissues. Therefore, RNA in situ hybridization is a powerful approach for studying tissue- and temporal-specific gene expression. In this method, oligonucleotides, cloned DNA fragments, or antisense RNA transcripts of cloned DNA fragments corresponding to unique portions of prostate-specific or testis-specific genes are used to detect specific mRNA species, e.g., in the tissues of animals, such as mice, at various developmental stages, or to monitor tumor progression. Other gene expression detection techniques are known to those of skill in the art and can be employed for detection of prostate-specific or testis-specific gene expression.

Identification of Additional Prostate-Specific or Testis-Specific Genes

Standard techniques, such as the polymerase chain reaction (PCR) and DNA hybridization, as well as the SSH and other techniques described herein, can be used to clone prostate-specific or testis-specific homologues in other species and other prostate-specific or testis-specific genes in humans. Prostate-specific or testis-specific genes and homologues can be readily identified using low-stringency DNA hybridization or low-stringency PCR with human prostate-specific or testis-specific probes or primers. Degenerate primers encoding human prostate-specific or testis-specific or human prostate-specific or testis-specific amino acid sequences can be used to clone additional prostate-specific or testis-specific genes and homologues by RT-PCR.

Additional prostate-specific or testis-specific genes include genes expressed during various growth and developmental phases of the diseased prostate or testis, e.g., those involved in prostate cancer, benign prostatic hyperplasia, or testicular cancer, and genes expressed as a result of a drug regimen.

Construction of Transgenic Animals and Knockout Animals

Characterization of prostate-specific or testis-specific genes provides information that allows prostate-specific or testis-specific knockout animal models to be developed by homologous recombination. Preferably, a prostate-specific or testis-specific knockout animal is a mammal, most preferably a mouse. Similarly, animal models of prostate-specific or testis-specific overproduction can be generated by integrating one or more prostate-specific or testis-specific sequences into the genome of an animal, according to standard transgenic techniques. Moreover, the effect of prostate-specific or testis-specific gene mutations (e.g., dominant gene mutations) can be studied using transgenic mice carrying mutated prostate-specific or testis-specific transgenes or by introducing such mutations into the endogenous prostate-specific or testis-specific gene, using standard homologous recombination techniques.

A replacement-type targeting vector, which can be used to create a knockout model, can be constructed using an isogenic genomic clone, for example, from a mouse strain such as 129/Sv (Stratagene Inc., LaJolla, Calif.). The targeting vector can be introduced into a suitably-derived line of embryonic stem (ES) cells by electroporation to generate ES cell lines that carry a profoundly truncated form of a prostate-specific or testis-specific gene. To generate chimeric founder mice, the targeted cell lines are injected into a mouse blastula-stage embryo. Heterozygous offspring can be interbred to homozygosity. Prostate-specific or testis-specific knockout mice provide a tool for studying the role of prostate-specific or testis-specific polypeptides and nucleic acid molecules in embryonic development and in disease. Moreover, such mice provide the means, in vivo, for testing therapeutic compounds for amelioration of diseases or conditions involving a prostate-specific or testis-specific polypeptide or nucleic acid molecule-dependent or prostate-specific or testis-specific polypeptide or nucleic acid molecule-affected pathway.

Animal Models

The prostate-specific and testis-specific polypeptides, antisense compounds, etc., of the invention can also be used in conjunction with animal models of prostate or testis disorders, to test the therapeutic, diagnostic, and screening methods of the invention. An exemplary prostate cancer model in transgenic mice is called TRAMP, in which the SV40 large T antigen is targeted to the prostate (Greenberg et al., PNAS 92, 3439–3443, 1995). Another test system is the CWR22 (androgen-dependent) and CWR22R (androgen-independent) xenografts, as known in the art and as described herein. Growth, PSA secretion, metastasis, etc. of these xenografts could be monitored in the presence and absence of the prostate-specific or testis-specific polypeptides, nucleic acid molecules, and other compounds of the invention. Other animal models, for example, animal models of other forms of cancer, or immunocompromised animals, e.g., nude mice, may also be used.

The following Examples will assist those skilled in the art to better understand the invention and its principles and advantages. It is intended that these Examples be illustrative of the invention and not limit the scope thereof.

EXAMPLE 1

Suppression Subtraction of Prostate- and Testes-Specific Genes and Subcloning Into Pzero cDNA derived from poly(A)+ RNA of 10 different normal human tissues were subtracted against normal human prostate cDNA using suppression subtraction hybridization (SSH) (Diatchenko, L. et al., Proc. Natl. Acad. Sci. USA 93, 6025–6030, 1996) and the resulting cDNA fragments were cloned into an appropriate vector. SSH was performed as described (Clontech PCR-Select Cloning Kit) using prostate poly(A)+ RNA against a pool of poly(A)+ RNA obtained from ten normal human tissues (heart, brain, placenta, lung, liver, skeletal muscle, kidney, spleen, thymus, and ovary). Upon secondary PCR amplification (12 cycles), the reactions were extracted with phenol/chloroform, the DNA with ethanol, and the pellets washed once with 70% ethanol. After drying, the DNA pellet was dissolved in 0.2XTE or MQ dH$_2$O and cut with RsaI in a 20 µl reaction for 2 hrs at 37° C. to excise adaptors. After digestion, the reactions were run on a 1.5% agarose gel, with molecular size markers on one side, at 5 V/cm, 40 min. Care was taken not to expose the gel to short wavelength UV light. The adapter bands were excised, and the gel was run at 5 V/cm for 15 min in a reversed electric field to concentrate the cDNA bands.

The gel was visualized (long wave UV light) and the amplified cDNAs, ranging in size between 100 bp–1 kB, were excised. The DNA was purified using the QAIEX gel DNA purification kit. The purified DNA was cloned into EcoRV-cut, dephosphorylated pZERO (Invitrogen). Ligation reactions were performed in 10 µl final volume in the presence of 5% PEG, 1×T4 Ligase buffer at 37° C. overnight and a ⅕ dilution of 1 µl of the ligation mix (PSL) was transformed into DH10B electrocompetent cells (>10$^{10}$ efficiency) or equivalent. Colonies were picked and the presence of cDNA inserts was confirmed. To that end, PCR was performed with T7 and SP6 primers directly from the colonies. 10% of the reactions were run on a 1.5% agarose gel to visualize amplified products. The colonies with inserts were grown and glycerol stocks (15%) were prepared and stored at −80° C.

EXAMPLE 2

Reverse Northern Blot and Sequence Analyses

To clone androgen-responsive genes represented in the PSL, the reverse northern technique was used (Hedrick, S. M. et al., Nature 308, 149–153, 1984; Sakaguchi, N. et al., EMBO J. 5: 2139–2147, 1986). In this procedure, RNA made from two populations of cells that are to be compared is used to make cDNA probes that are then hybridized to two identical arrays of clones. To that end, PSL clones were amplified by PCR and spotted on nylon filters in 96-well format to generate two identical blots for each set of 92 clones (the remaining four spots were used for positive and negative controls). To make the probes, the androgen-responsive prostate cancer cell line LNCaP was used (Horoszewicz, J. S. et al., Cancer Res. 43, 1809–1818, 1983) and was either left untreated (the (−) probe) or treated with the synthetic androgen R1881 for 24 hours (the (+) probe). Poly(A)+ RNA was isolated from these cells and was used to make the $^{32}$P-labeled probes. After hybridization with the (−) and (+) probes, clones that showed differential hybridization were selected for further analysis, i.e., confirmation by a secondary reverse northern blot, and northern blotting.

Reverse northern screening on the cDNA clones was done essentially as described previously (Hedrick, S. M. et al., supra; Sakaguchi, N. et al., supra) with some modifications. DNA (approximately 400 ng) from PCR amplification in step 6 was diluted in 200 µl of 0.4M NaOH, 10 mM EDTA and mixed well by pipetting. After incubation at 95° C. for 5–10 minutes, the tubes were chilled on ice. Denatured DNA was blotted on two separate pieces of Zeta Probe GT+ membrane (Bio-Rad) using a dot-blot apparatus (Bio-Rad). Positive (Prostate specific antigen (PSA) cDNA) and negative (glyceraldehyde 3-phosphate dehydrogenase (G3PDH) cDNA) controls were included on each blot (bottom right) in duplicate. The membranes were rinsed with 2×SSC, air dried, and then baked at 80° C. for 30 minutes. An exemplary reverse northern analysis is shown in FIG. 1. Note that there was a substantial increase in PSA hybridization in the (+) blot (probe prepared from cells that have been stimulated by androgens) compared with the (−) blot (probe prepared from unstimulated cells), whereas there was no significant change in hybridization of G3PDH between the two blots. Arrowheads indicate the positive clones identified in this experiment.

Figure 2:
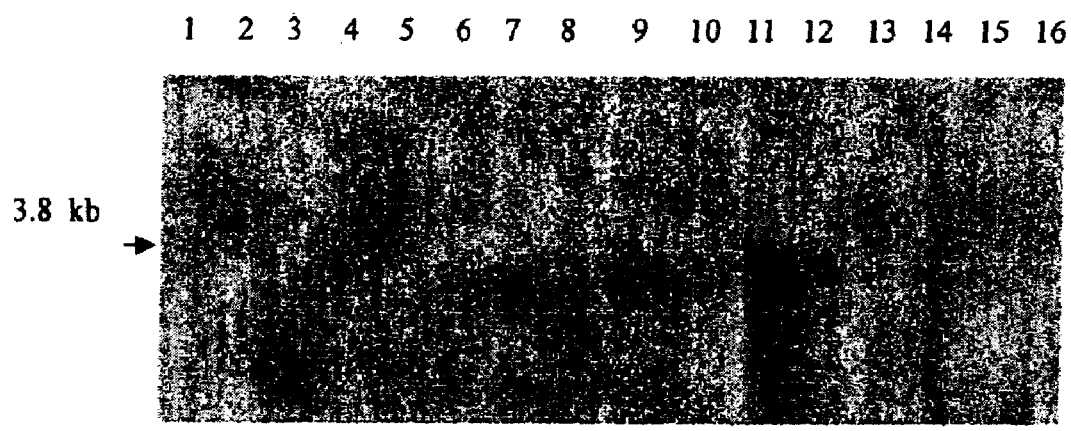
FIG. 2 shows an exemplary multiple tissue northern blot.

To verify the tissue-specific nature of the isolated sequences, positive clones were tested in a standard northern blot against RNA preparations of multiple non-prostate tissue samples. FIG. 2 shows a multiple tissue northern blot using NKX3A as a probe, to show an exemplary tissue expression pattern seen in the positive clones. Lanes 1–10, and 12–16 are RNA preparations from non-prostate tissues, lane 11 is a RNA preparation from prostate, lane 12 is a RNA preparation from testis.

Twelve clones with no significant homology to known sequences (by BLAST analysis) were isolated from prostate tissue and LNCaP cells. SEQ ID NOs: 1–9 were identified as androgen-responsive differentially-expressed genes in the prostate, while SEQ ID NOs: 10–12 were identified as androgen-responsive differentially-expressed genes in LNCaP cells.

EXAMPLE 3

Isolation and Characterization Of The STMP1 Gene And mRNA

A normal prostate cDNA library was screened by 5'- and 3'-RACE analysis, and resulted in the full-length cDNA for L74. Since computer-aided secondary structure prediction of the deduced amino acid sequence of L74 suggested the presence of a six-transmembrane domain in its C-terminal half, L74 was renamed Six-Transmembrane Protein of Prostate 1 (STMP1).

Figure 4A:
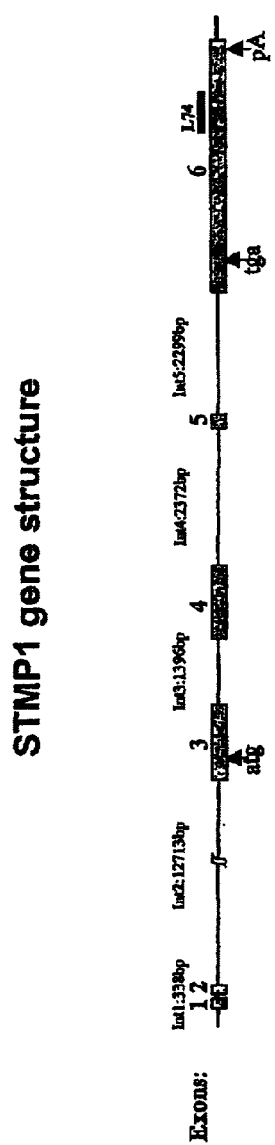
FIG. 4A is a schematic diagram showing the STMP1 gene structure.

When the full-length STMP1 cDNA was used in BLAST analysis, it was found to match a BAC clone (GenBank accession # AC002064) except for a 313 bp repetitive unit in the 3' UTR region, thereby identifying it as the STMP1 gene and localizing it to Chr7q21. The repetitive region is likely to be a cloning or sequencing artifact of the BAC clone. Computational exon/intron junction analysis and alignment of the full-length cDNA sequence with the BAC clone revealed that STMP1 gene is composed of six exons and five introns (FIG. 4A). The transcription start site, the location and size of the exons and introns, and the location of the partial cDNA clone L74 (black box) are indicated. The start (atg) and stop codons (tga), as well as the putative polyadenylation signal (pA) are also indicated. The first two exons are short, non-coding exons of 83 and 61 bp, whereas exons 3–6 encode the open reading frame (ORF) and are 525, 528, 165, and 3281 bp long, respectively (FIG. 4C). The STMP1 gene spans around 26 kb, which is in part due to the extremely large size of intron 2 (12713 bp). There are three different predicted promoters within 4 kb upstream of the STMP1 initiation codon, none of which has any significant TATA or CAAT box consensus sequences, suggesting that STMP1 is transcribed from a TATA-less promoter.

Figure 4B:
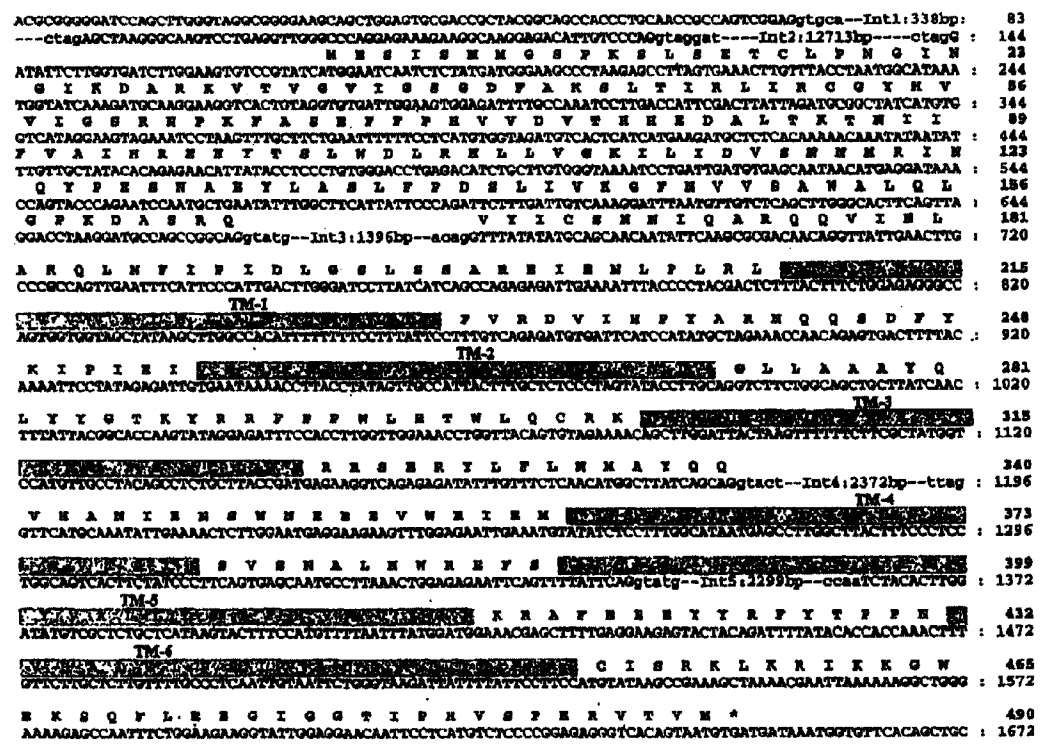

The STMP1 cDNA (GenBank accession # AY008445) has a predicted 5' untranslated region (5'UTR) of approximately 1 kb (deduced by RACE analysis) and an unusually long 3'UTR of approximately 4 kb that comprises ~77% of the total cDNA sequence. The ORF starts within the $3^{rd}$ exon and is predicted to encode a 490 amino-acid protein (FIG. 4B). A search for protein motifs identified six predicted transmembrane domains in the C-terminal half of STP1 starting at F209 (FIGS. 4B and 4E). Only the cDNA sequence surrounding the ORF is indicated. The exon-intron junctions are indicated and the location of the predicted transmembrane domains are highlighted (TM 1–6) (FIG. 4B). The stop codon is indicated with an asterisk. STMP1 has two alternatively spliced forms, shown in FIGS. 4F–4K, which lead to two predicted isoforms of the protein.

EXAMPLE 4

STMP1 Belongs To A New Subfamily Of Six-Transmembrane Domain Proteins

Figure 5:
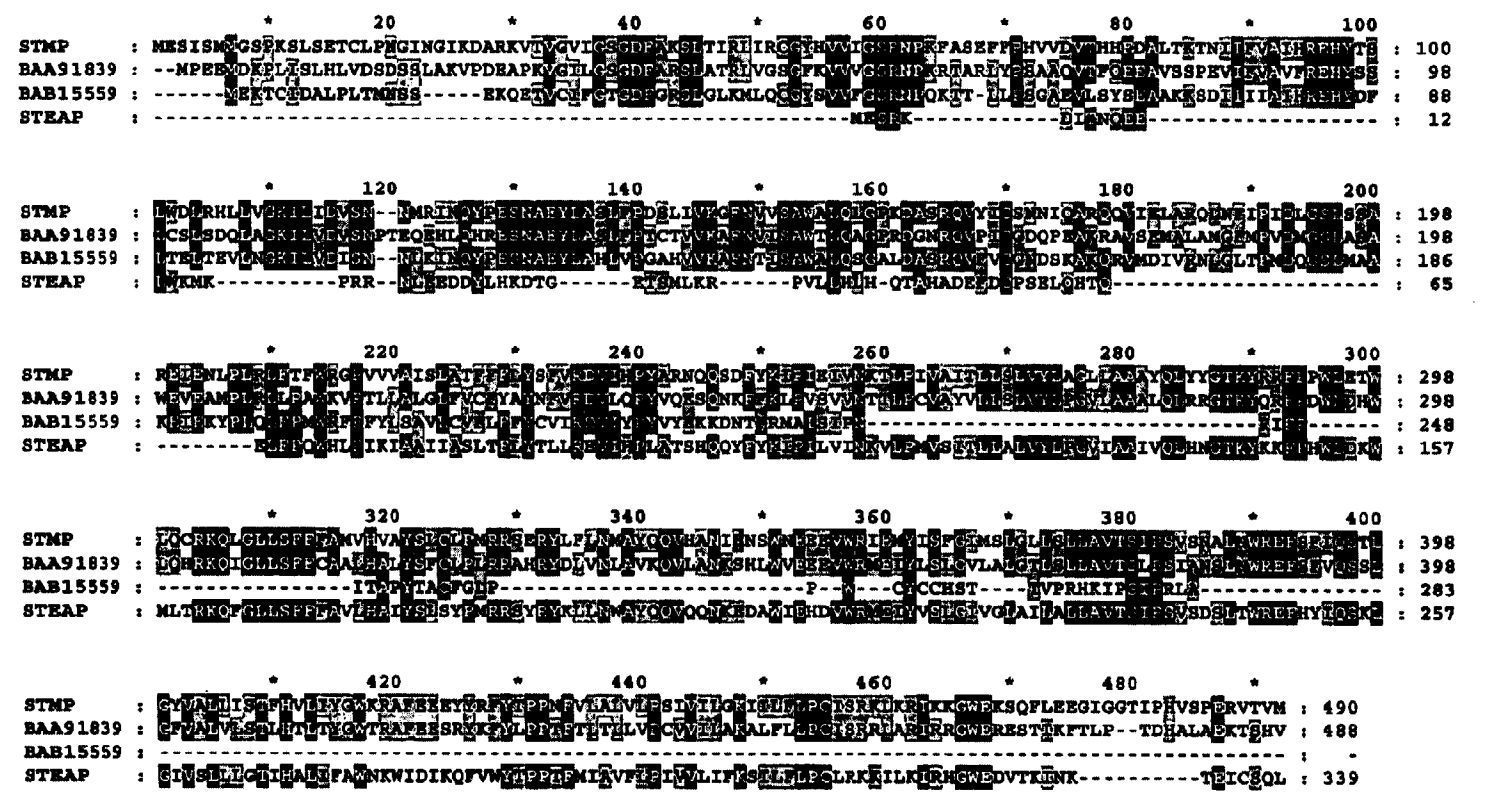

BLAST analysis of GenBank with the predicted STMP1 amino acid sequence identified two independent ESTs and STEAP, a recently discovered cell membrane protein enriched in prostate for expression. An alignment of these sequences, obtained by Clustal and GenDoc programs, is shown in FIG. 5. Completely conserved residues are shaded in black; residues that are conserved in two or three of the sequences are shaded light and dark gray, respectively. This alignment suggested that while the EST BAA91839 cDNA may be close to full-length, BAB15559 cDNA may represent a partial sequence.

The sequences of two proteins related to STMP1 were determined (FIGS. 4L and 4M, STMP2 and STMP3, respectively). The STMP2 and STMP3 sequences contain the EST sequences. The GFP-fusion of STMP2 gives similar localization as STMP1. Both STMP2 and STMP3 are more widely distributed and have higher levels in some tissues other than the prostate. For example, STMP2 has the highest expression in the placenta and the lung, and is also highly expressed in the heart, liver, prostate, and testis, while STMP3 has the highest expression in the liver, and is also highly expressed in the heart, placenta, lung, kidney, pancreas, prostate, testis, small intestine, and colon.

The sequence similarity between STMP1 and STEAP is limited and not significant before residue 210 of STMP1 where the predicted six-transmembrane coding domain starts. This suggests that the N-terminal region is structurally and functionally related among STMP proteins, forming a six-transmembrane protein subfamily that is distinct from STEAP.

EXAMPLE 5

STMP1 Expression is Highly Enriched in Prostate

Figure 6:
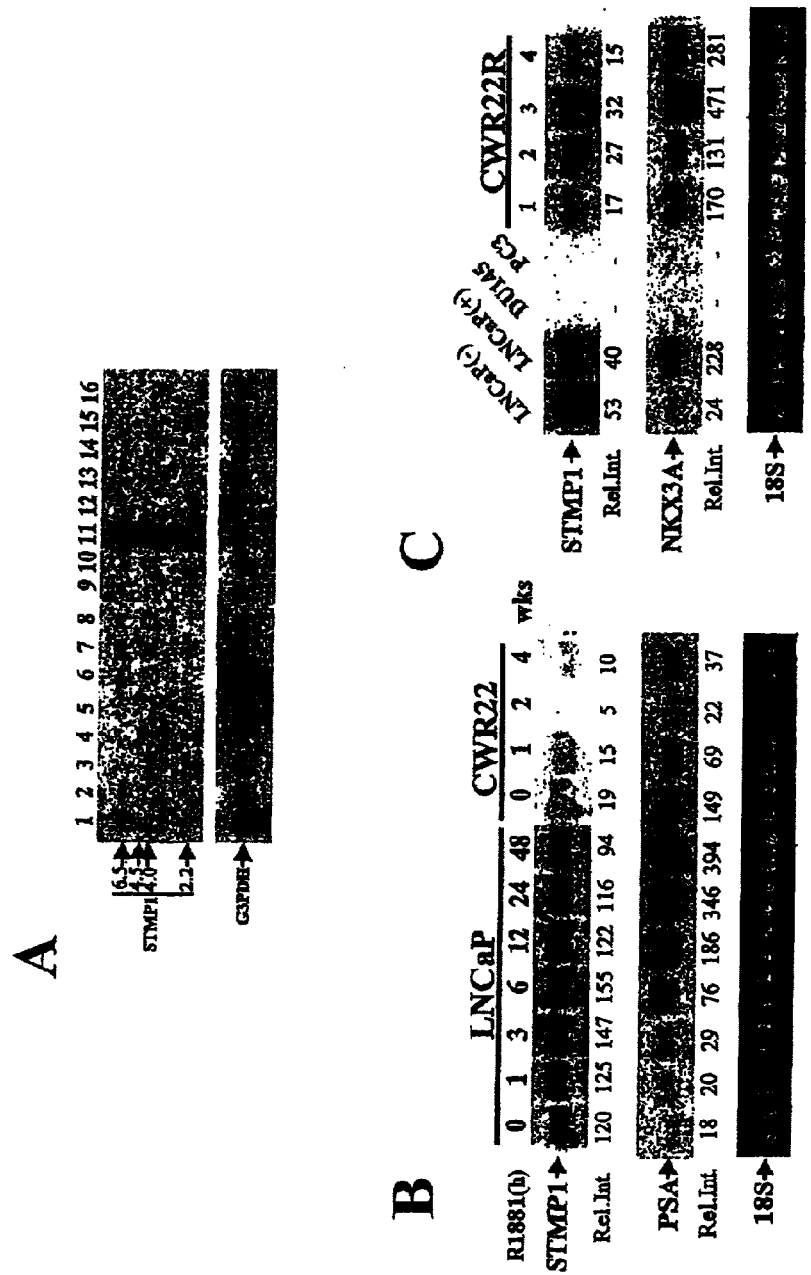
FIG. 6A shows a multiple tissue Northern blot probed with STMP1 or G3PDH cDNA.
FIG. 6B is a Northern blot probed with STMP1 and PSA in the androgen-responsive prostate cancer cell line LNCaP and in the CWR22 human prostate cancer xenograft model.
FIG. 6C is a Northern blot probed with STMP1 and NKX3A in LNCaP, PC-3, and DU-145 cell lines and in the CWR22R human prostate cancer xenograft model.

The expression profile of STMP1 was then determined in various human tissues by Northern analysis, in which a multiple tissue Northern blot was hybridized to the STMP1 probe (see Materials and Methods). As shown in FIG. 6A, STMP1 hybridized to a major mRNA species of 6.5 kb, and three minor mRNA species of 2.2, 4.0, and 4.5 kb in the prostate tissue. The stronger hybridization that is observed with G3PDH in the heart and skeletal muscle samples is due to its higher expression in these tissues. The lanes represent: 1. Heart, 2. Brain, 3. Placenta, 4. Lung, 5. Liver, 6. Skeletal Muscle, 7. Kidney, 8. Pancreas, 9. Spleen, 10. Thymus, 11. Prostate, 12. Testis, 13. Ovary, 14. Small Intestine, 15. Colon, 16. Peripheral blood leukocyte. The location of the fill-length 6.5 kb mRNA, as well as the lower molecular weight STMP1 species are indicated by arrows to the left of the figure. There was 15–20-fold lower mRNA expression of the 6.5 kb band in the heart, brain, kidney, pancreas, and ovary, compared to prostate, and no detectable expression in other tissues. In contrast, the three lower molecular weight species, encoded by alternatively spliced forms of STMP1, were only detectable in the prostate. Hybridization with a glyceraldehyde 3-phosphate dehydrogenase (G3PDH) cDNA probe resulted in approximately similar signals in all lanes, except for the heart and skeletal muscle where G3PDH is known to be more abundant compared with other tissues. These data show that STMP1 expression is high in the prostate, although expression can be seen in other tissues, and that STMP1 has isoforms that are restricted to the prostate for expression.

EXAMPLE 6

Characterization of STMP1 Expression

Since androgen is a major hormonal stimulus for the normal prostate gland and for early stage prostate cancer, the possible androgen regulation of STMP1 was assessed by Northern analysis in the androgen-responsive prostate cancer cell line LNCaP. Cells were either left untreated or treated with the synthetic androgen R1881 ($10^{-8}$ M) with increasing amounts of time (hours) as indicated (FIG. 6B), harvested, and total RNA isolated and used in Northern analysis with STMP1 cDNA as probe. The same membrane was also probed for the androgen-dependent gene PSA. Relative induction of mRNA accumulation is indicated at the bottom of the lanes, as determined by phosphorimager analysis (Molecular Dynamics). The CWR22 xenograft was grown in nude mice and tumor samples were collected either before (t=0) or 1, 2, or 4 weeks after castration. Total RNA was isolated and was then used in Northern analysis with the same probes. Ethidium bromide-stained 18S RNA is shown as a control for RNA integrity and loading. At 6 h, there was an approximately 25% increase in STMP1 expression, which was lost by 24 h, with a final 20% decrease observed at 48 h compared with basal levels. In contrast, the mRNA accumulation of the androgen-regulated gene PSA dramatically increased upon androgen stimulation in a time-dependent manner, as expected, reaching approximately 22-fold higher levels by 48 hours. Relative induction of STMP1 mRNA accumulation is indicated at the bottom of the lanes determined by phosphorimager analysis. As is shown in FIG. 6B, STMP1 displayed similar expression levels in untreated and R1881-treated LNCaP cells, indicating that STMP1 expression is not significantly regulated by androgens in LNCaP cells.

To determine the possible androgenic regulation of STMP1 expression in an in vivo setting, the androgen-dependent xenograft model CWR22, which is derived from a primary human prostate tumor was used (Wainstein, M. A. et al., *Cancer Res* 54, 6049–6052, 1994). Since they are androgen-dependent for growth, the CWR22 tumors in nude mice display marked regression upon castration and may regress completely. CWR22 xenografts were grown in nude mice in the presence of a sustained release testosterone pellet. After the tumors had grown, the mice were castrated, the testosterone pellets were removed, and the regressing tumors were collected at 1, 2, or 4 weeks post-castration. Total RNA was prepared from these tumor samples and used in Northern analysis. As shown in FIG. 6B, similar to the obsevations in LNCaP cells, STMP1 mRNA accumulation in the CWR22 tumors showed no significant change upon castration and was not affected by the presence of androgens (note that there is underloading of RNA for CWR22 2 wk sample). In contrast, the mRNA accumulation of the androgen-regulated gene PSA was dramatically decreased upon castration, dropping to approximately 16% of pre-castrate levels by two weeks post-castration. These results are consistent with the findings in LNCaP cells and suggest that STMP1 expression is not significantly regulated by androgens in prostate cancer cells. STMP1 expression was substantially lower in the CWR22 tumors compared with LNCaP cells.

The expression profile of STMP1 was also analyzed in the androgen-independent prostate cancer cell lines PC3 and DU145, as well as in four independent, relapsed derivatives of CWR22 tumors, named CWR22R (Nagabhushan, M. et al., *Cancer Res* 56, 3042–3046, 1996), representative of advanced prostate cancer (FIG. 6C). LNCaP (in the presence (+) or absence (−) of R1881 ($10^{-8}$ M)), PC-3, or DU-145 cells were grown and total RNA was isolated. Four independent lines of the androgen independent human prostate cancer xenograft CWR22R, were grown in nude mice, tumors were collected, and total RNA was isolated and used in Northern analysis with STMP1 or the androgen target gene NKX3.1 cDNAs as probes. Ethidium bromide-stained 18S RNA is shown as a control for RNA integrity and loading. The relative induction of STMP1 and NKX3.1 mRNA accumulation is indicated at the bottom of the lanes determined by phosphorimager analysis (Molecular Dynamics). As is shown in FIG. 6C, STMP1 expression was high in LNCaP cells and did not significantly change in response to R1881 treatment compared with a ~9-fold induction of the androgen target gene NKX3.1. There was no STMP1 expression in the androgen-independent prostate cancer cell lines PC-3 or DU-145, as was the case for NKX3.1. In contrast, there was significant STMP1 expression in tumors from all four independent CWR22R xenograft lines tested, ranging between ~30–60% of that observed in LNCaP cells. A similar overexpression pattern was also observed for NKX3.1 (FIG. 6C) consistent with previous findings (Korkmaz, K. S. et al., *Gene* 260, 25–36, 2000).

An interesting property of STMP1 expression profile is that even though it is expressed at low levels in the androgen dependent CWR22 xenograft, it is highly expressed in the relapsed CWR22R which is androgen receptor (AR) positive, but is not responsive to androgens. This indicates that STMP1 expression is deregulated once the prostate tumor progresses from an androgen-dependent to an androgen-independent phase. In addition, STMP1 is not expressed in the AR-negative prostate cancer cell lines PC-3 and DU-145, but is expressed at high levels in the AR-positive cell line LNCaP and the CWR22 and CWR22R xenografts. Thus, expression of STMP1 is correlated with the presence of a functional AR in the cell.

It has been known for over 50 years that androgens play a key role both in the development and maintenance of the normal prostate and the initiation and progression of prostate cancer. Androgen withdrawal results in involution of both the normal prostate gland as well as a prostate tumor in the early stages of the disease that is still androgen dependent. Consequently, androgen withdrawal is commonly used as treatment to reverse tumor growth. However, in the case of the prostate tumor, after a few months or years, the tumor recurs in almost all cases in an androgen-independent state. At this point there is no effective therapy and prognosis for survival is extremely poor. Since STMP1 is overexpressed during this later androgen-insensitive state, it will be a useful tool in diagnostic and therapeutic applications for prostate cancer.

These data indicate that STMP1 expression is deregulated once prostate cancer progresses from an androgen-dependent to an androgen-independent state.

EXAMPLE 7

Intracellular Localization of STMP1

To gain insight into the intracellular localization pattern of STMP1, a green fluorescent protein (GFP)-STMP1 fusion protein was generated. The use of such GFP chimeric proteins has recently become a standard method to assess intracellular localization and dynamics of proteins. COS-1 cells were transiently transfected with GFP-STMP1, fixed and processed for confocal microscopy as described in Materials and Methods.

Figure 7A:
FIG. 7A shows fluorescence microscopy images of COS-1 cells transiently transfected with GFP-STMP1.

A series of 11 confocal sections along the z-axis were collected through a single cell at nominal 100 nm intervals. Three of the consecutive sections and the projection of all 11 sections are shown in FIG. 7A. Arrows indicate tubular-vesicular structures (VTS) in different sizes, shapes, and locations (Bar=5 μm). In all 11 z-plane sections, GFP-STMP1 showed bright juxtanuclear distribution pattern, characteristic of the Golgi complex. Additionally, GFP-STMP1 was dispersed in spots of variable size throughout the cytoplasm and at the cell periphery (z-7, projection). Some of these bright fluorescent spots were tubular (z-6, arrow and FIG. 8) or vesicular (z-5, arrow) in morphology.

Figure 7B:
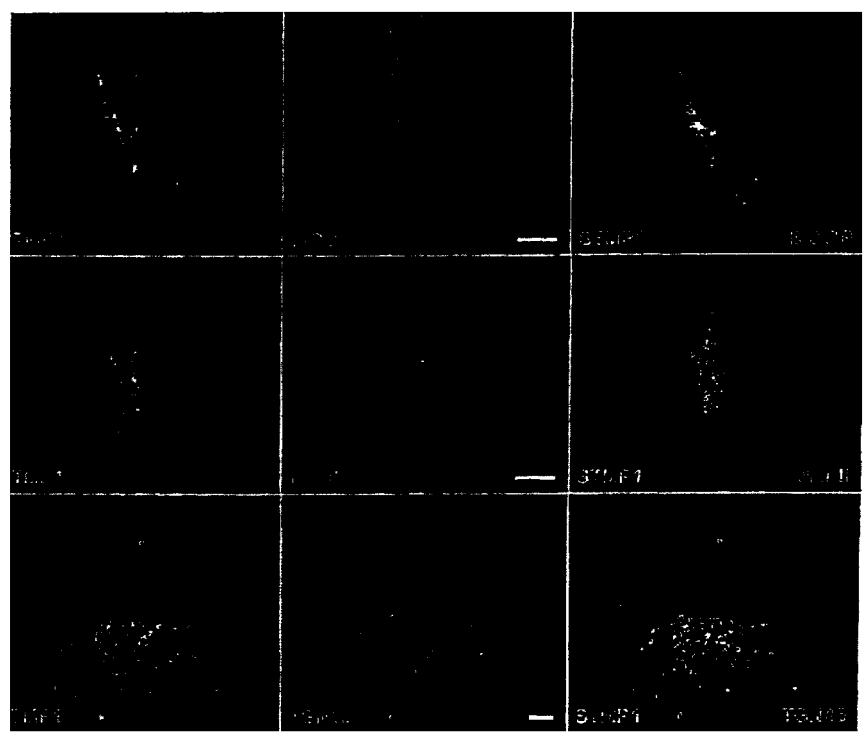
FIG. 7B shows fluorescence microscopy images of COS-1 cells transiently transfected with GFP-STMP1 and labeled with antibodies against Golgi markers.

To determine more directly whether GFP-STMP1 was localized to the Golgi complex, we compared its intracellular distribution with those of two well characterized Golgi markers, the medial Golgi enzyme mannosidase II (ManII) (Rabouille, C. et al., *J Cell Sci* 108, 1617–1627, 1995) and the coat protein β-COP (Pepperkok, R. et al., *Cell* 74, 71–82, 1993). COS-1 cells were transfected with GFP-STMP1, fixed, labeled with the appropriate primary and secondary antibodies and imaged by confocal laser scanning microscopy. Green GFP-STMP1 fluorescence and red (Texas Red-labeled secondary antisera) β-COP and ManII fluorescence were detected by confocal laser microscopy. Panels to the right show the overlay images with yellow/orange staining indicating the regions of colocalization. Bars=5 μm. As shown in FIG. 7B, the distribution of GFP-STMP1 extended throughout the Golgi complex, as evidenced by significant colocalization with both ManII and β-COP. However, some areas of non-overlap between the GFP-STMP1 and both Golgi markers were observed suggesting that STMP1, at least in part, is differentially localized within the Golgi complex compared with these two markers.

Since GFP-STMP1 was associated with VTS (FIG. 7A and FIG. 8), more specific localization of GFP-STMP1 to the trans-Golgi network (TGN), an important site for the sorting of proteins destined to the plasma membrane, secretory vesicles, or lysosomes (Farquhar, M. G. & Palade, G. E. *Trends Cell Biol* 8, 2–10, 1998; Mellman, I. & Warren, G., *Cell* 100, 99–112, 2000; Lemmon, S. K. & Traub, L. M., *Curr Opin Cell Biol* 12, 457–466, 2000) was assessed. An antibody against TGN46, a TGN resident protein that shuttles between the TGN and the plasma membrane (Prescott AR, et al., *Eur J Cell Biol* 72, 238–246, 1997; Ponnambalam, S. et al., *J Cell Sci.* 109, 675–685, 1996), was used in immunoflourescence microscopy experiments as above. As shown in FIG. 7B, GFP-STMP1 extensively colocalized with TGN46, greater than that observed with ManII and β-COP, suggesting that in the Golgi complex, STMP1 is primarily localized to the TGN. Note that the images with TGN46 were obtained with lower objective power.

EXAMPLE 8

Figure 8:
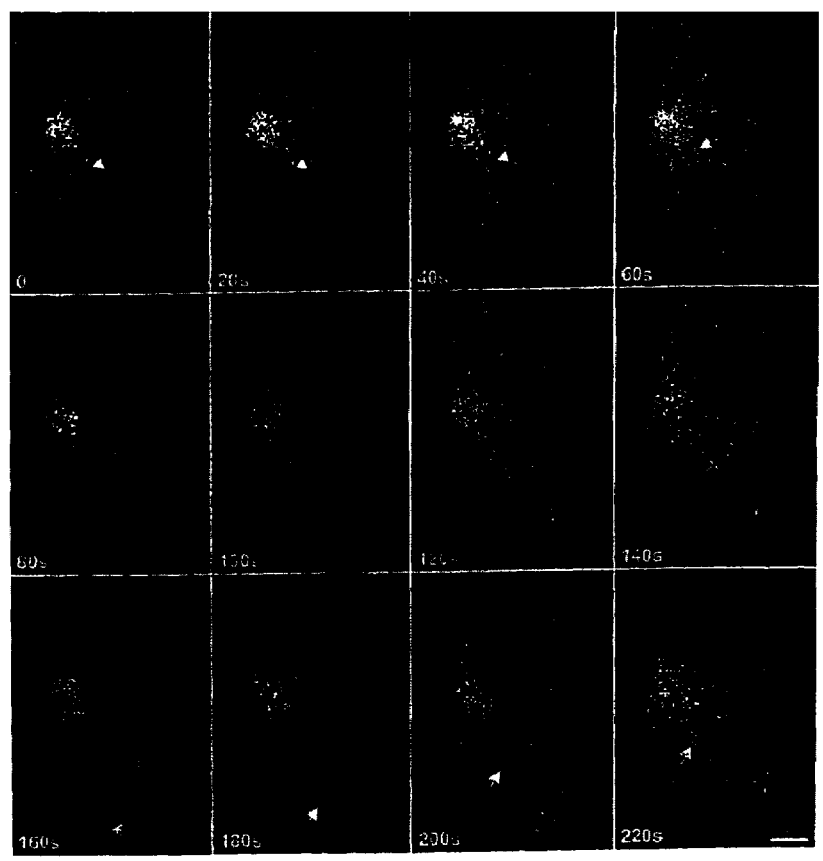
FIG. 8 shows fluorescence microscopy images of COS-1 cells transiently transfected with GFP-STMP1 and observed by live-cell confocal microscopy.

STMP1 Shuttles between the Golgi and the Plasma Membrane and Colocalizes to the Early Endosomes The dynamic properties and intracellular trafficking of GFP-STMP1 were studied using confocal time-lapse imaging in living cells. COS-1 cells were transiently transfected with GFP-STMP1 and, 16 h after transfection, 12 consecutive images were collected from live cells every 20 s at 37° C. by confocal laser scanning microscope (FIG. 8). The upper panel shows a VTS extending out and retracting back to the Golgi body (white arrows). In the middle panel and the first image in the lower panel (160s), red arrows indicate the translocation of a VTS from the Golgi body to the cell periphery. In the lower panel, yellow arrows point to the movement of a VTS from the edge of the cell towards the Golgi body. Note that the results shown are representative of multiple time-lapse analyses and the changes in the images are not due to movement from the plain of focus. Bar=5 μm.

As shown in FIG. 8, some VTS were found to be detaching and some to be associating with the Golgi complex. The VTS were highly dynamic and pleiomorphic in size. Some of the VTS followed straight or curvilinear paths, some moved in a stop-and-go fashion, and some showed saltatory movements. The VTS indicated at the top panel (white arrows) extended away from and then retracted back to the Golgi. The VTS in the middle panel and the first image in the lower panel (red arrows) detached from the Golgi complex, paused, and then moved towards the cell periphery until it disappeared at the cell edge suggesting that STMP1 is associated with the secretory pathway. The VTS in the lower panel (yellow arrow) moved from the cell periphery towards the Golgi body suggesting that STMP1 is localized to the endocytic pathway.

EXAMPLE 9

Colocalization of GFP-STMP1 with the Early Endosomal Marker EEA1

Figure 9:
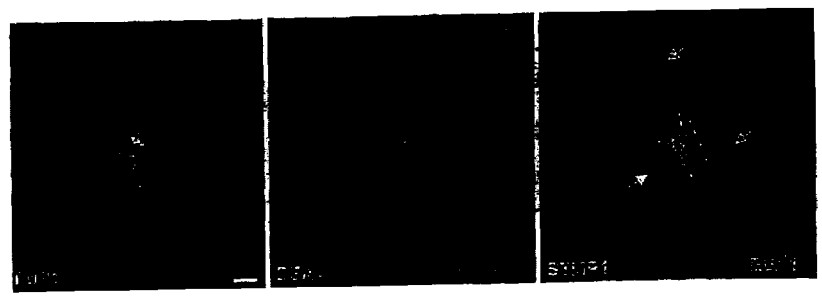
FIG. 9 shows fluorescence microscopy images of COS-1 cells transiently transfected with GFP-STMP1 and labeled with an antibody against an early endosomal marker.

To probe whether GFP-STMP1 was associated with the endocytic pathway, the intracellular distribution of GFP-STMP1 was compared with that of the early endosome protein EEA1 (Stenmark, H. et al., *J Biol Chem* 271, 204048–204054, 1996). COS-1 cells were transfected with GFP-STMP1, fixed, immunostained with EEA1 antibodies and observed by confocal laser scanning microscopy. Green GFP-STMP1 fluorescence and red (Texas Red-labeled secondary antiserum) EEA1 fluorescence were detected by confocal laser microscopy. The panel to the right shows the overlay images with yellow/orange staining indicating the regions of colocalization. Arrows indicate examples of the VTS in the cell periphery which contain both EEA1 and STMP1. Bar=5 μm. As shown in FIG. 9, EEA1 manifested a similar intracellular distribution in both transfected and untransfected cells. Furthermore, GFP-STMP1 significantly colocalized with EEA1 both in the cell periphery and also in the perinuclear area (FIG. 9, arrows) suggesting that STMP1 is associated with early endosomes and the endocytic pathway.

EXAMPLE 10

Isolation and Characterization of the SSH9 Gene and mRNA

Figure 10:
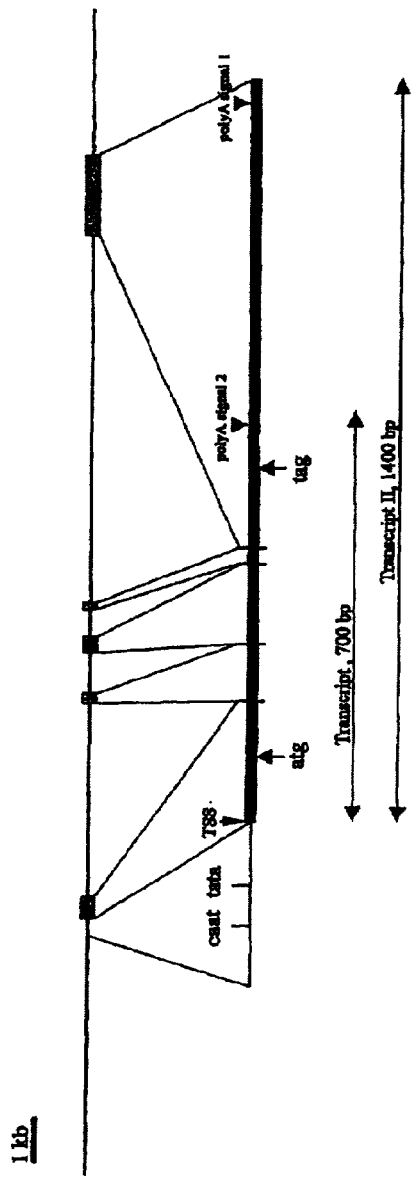
FIG. 10 is a schematic diagram showing the SSH9 gene structure and two mRNA species transcribed from the SSH9 gene.

The SSH9 gene was identified and mapped (FIG. 10). The predicted promoter site, the transcription start site, and the location and size of the exons and introns are indicated. The start and stop codons, as well as two polyadenylation signals, leading to two alternatively spliced transcripts, are also indicated. FIGS. 11A–C show the nucleotide and predicted amino acid sequence of SSH9, as well as the predicted promoter sequence and exon-intron boundaries.

The expression profile of SSH9, determined in various human tissues by Northern analysis (FIG. 12C), revealed that the 0.7 kb splice variant of SSH9 was highly testis-specific, while the 1.4 kb transcript was expressed in both prostate and testis.

Figure 12:
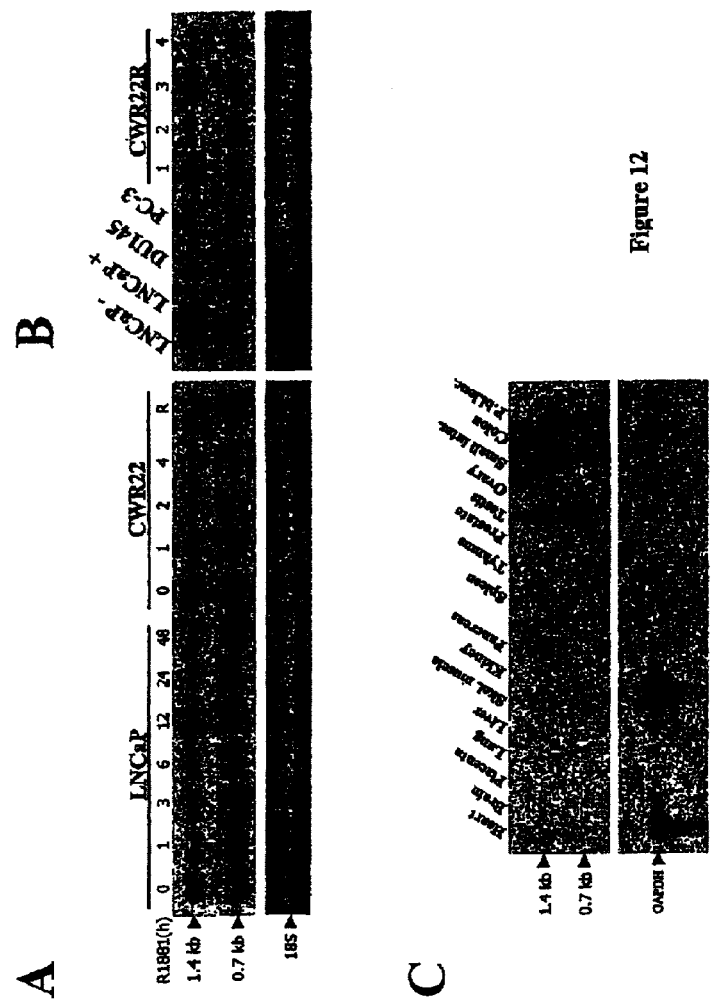
FIG. 12A is a Northern blot probed with SSH9 in the androgen-responsive prostate cancer cell line LNCaP cells and in the CWR22 human prostate cancer xenograft model.
FIG. 12B is a Northern blot probed with SSH9 in LNCaP, PC-3, and DU-145 cell lines, and CWR22R human prostate cancer xenograft model.
FIG. 12C is a multiple tissue Northern blot probed with SSH9 or GAPDH cDNA.

The androgen regulation of SSH9 was examined in LNCaP cells and in CWR22 xenografts (FIG. 12A) revealed that SSH9 is not regulated in LNCaP cells, but is regulated in CWR22 xenografts. The expression profile of SSH9 was also examined in the androgen-independent prostate cancer cell lines PC3 and DU145, and in CWR22R cells (FIG. 12B).

EXAMPLE 11

Isolation and Characterization of the PSL22 Gene and mRNA

Figure 13:
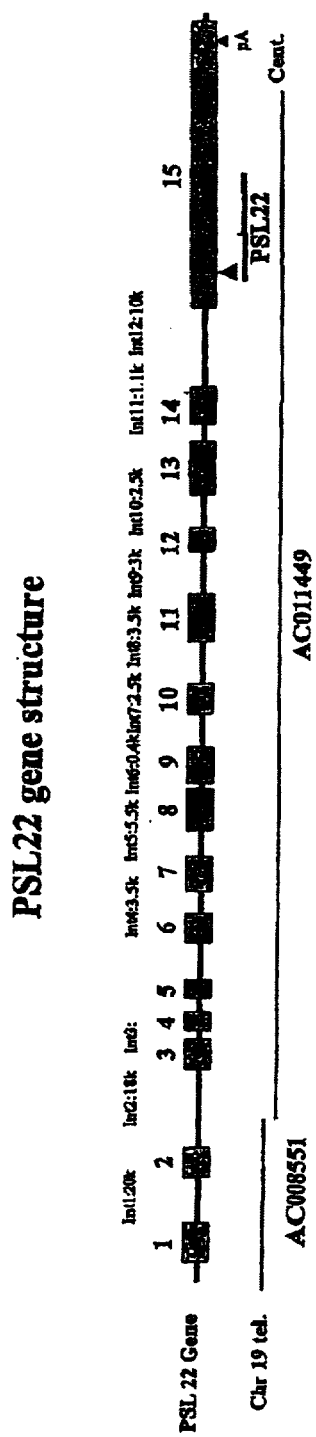
FIG. 13 is a schematic diagram showing the PSL22 gene structure.

The PSL22 gene was identified and mapped (FIG. 13). The location and size of the exons and introns, the location of the partial cDNA clone (black box), as well as the alignment of the full-length cDNA clone with GenBank Accession Nos. AC008551 and AC011449, are indicated. FIGS. 14A–C show the nucleotide sequence of the ORF, cDNA and predicted amino acid sequence, as well as the predicted promoter, exon, and UTR sequences of PSL22.

Figure 15:
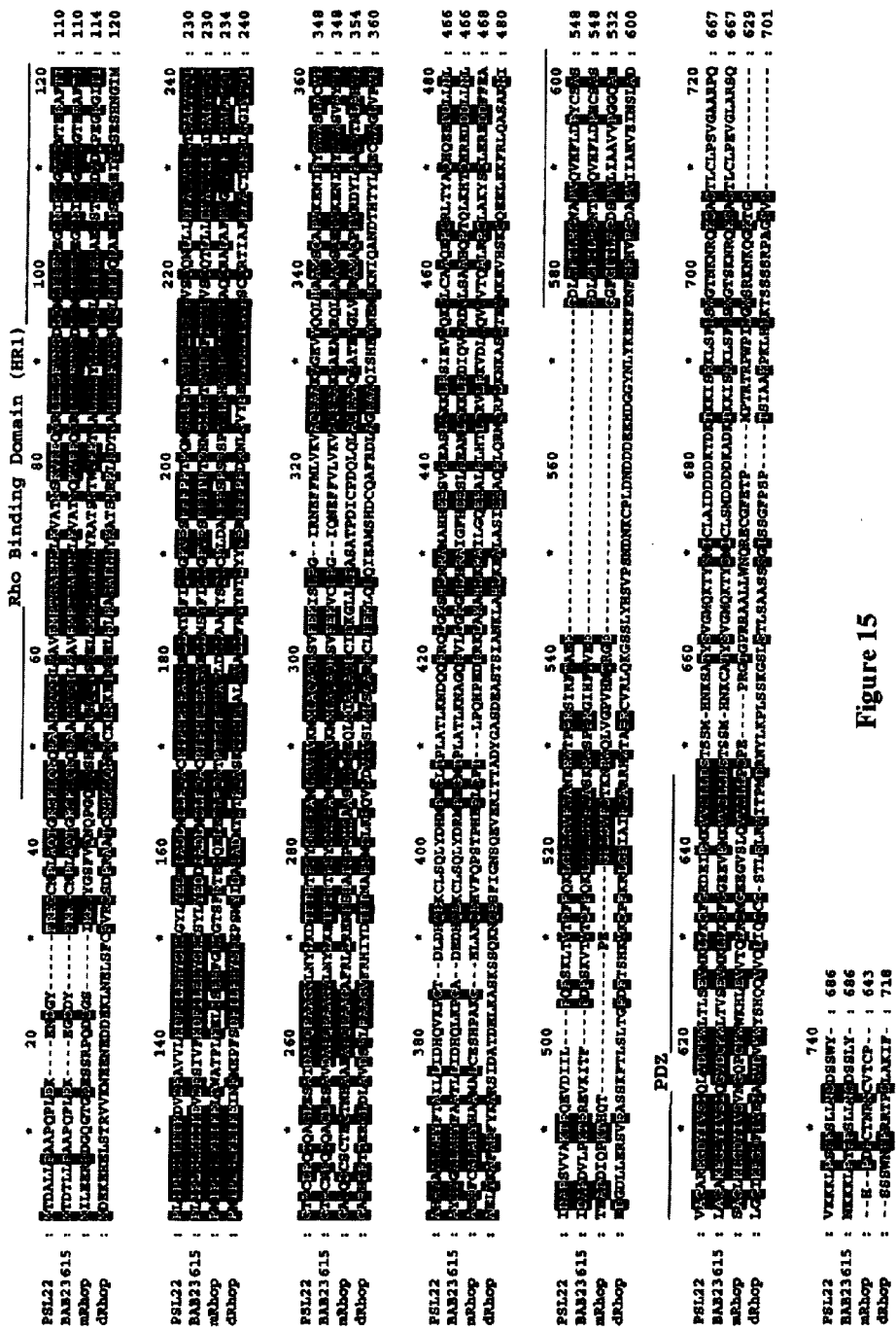
FIG. 15 shows a sequence alignment of PSL22 (RhoBP) (SEQ ID NO: 53), with ESTs NP032190 (mRhoph), AF132025 (dRhoph), and BAB23615 (SEQ ID Nos:71–73).

BLAST analysis of GenBank with the predicted PSL22 amino acid sequence identified PSL22 as a Rho binding protein. FIG. 15 shows a multiple sequence alignment of PSL22 with related proteins. Completely conserved residues are shown in black; residues found in three sequences are shaded.

The expression profile of PSL22, determined in various human tissues by Northern analysis (FIG. 116B), revealed that while the highest expression was seen in the prostate, high expression was seen in the kidney, pancreas, and colon.

Figure 16:
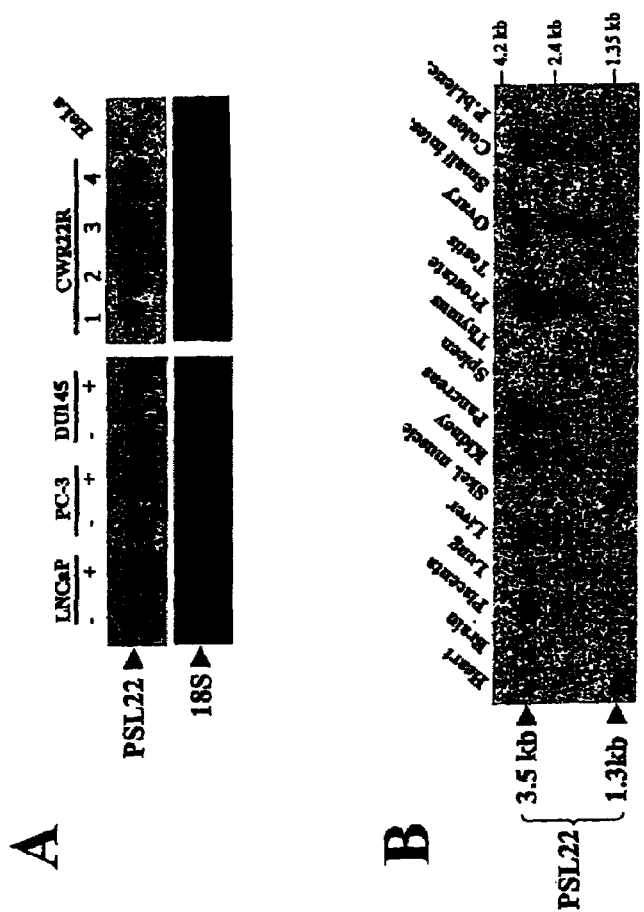
FIG. 16A is a Northern blot probed with PSL22 in LNCaP, PC-3, and DU-145 cell lines, and in the CWR22R human prostate cancer xenograft model.
FIG. 16B is a multiple tissue Northern blot probed with PSL22 cDNA.

The androgen regulation of PSL22 was examined in LNCaP cells, in the androgen-independent prostate cancer cell lines PC3 and DU145, and in CWR22R cells (FIG. 16A). The results showed that PSL22 is androgen regulated in LNCaP cells, where it is highly expressed, but is not androgen regulated in the PC3 and DU145 cells.

EXAMPLE 12

Materials And Methods

The following materials and methods were used in performing the exemplary experiments shown herein. It is understood that these materials and methods are subject to modifications that do not change the nature of the invention, as will be understood by those of ordinary skill in the art.

Probes

| Poly (A) + RNA | 1 μg [(−) or (+)] |
|---|---|
| Random primer (N7) | 200 ng |

RNAse-free sterile $H_2O$ to 20 μl

Heat at 70° C. for 10 min, and chill on ice.

While heating the RNA samples, the following solution was prepared:

| 5X 1st strand buffer | 10 μl |
|---|---|
| 0.1 mM DTT | 5 μl |
| 10 mM each dTTP + dGTP | 2 μl |
| $^{32}P$ alpha dATP | 5 μl |
| $^{32}P$ alpha dCTP | 5 μl |
| Superscript II(200 U/μl, BRL) | 2 μl |

The solution was mixed by pipetting, spun briefly, incubated at 25° C. for 5 min, and then for an additional 1 hour at 37° C. 2 μl of 10 mM dCTP+dATP was added and the mixture was incubated for 30 min at 37° C. and then heat inactivated at 70° C. for 10 min. Unincorporated nucleotides were removed using prespun G25 columns (Bio-Rad). Specific activity (which should be over $5 \times 10^8$ cpm/μg) was calculated.

Hybridization

Freshly prepared 25 ml Hybridization mix (7% SDS, 0.5 M $NaHPO_4$, 1 mM EDTA) was pre-warmed at 65° C. and 12.5 ml was used for prehybridization of each membrane, 5–10 min at 65° C. The probe was heat denatured at 95° C. for 3–5 min and transferred to the prehybridization mix at 65° C. Hybridization was carried out at 65° C. overnight.

Washing

Wash solution I (2×SSC and 1% SDS) and II (0.1×SSC and 0.5% SDS) were prewarmed, and the membrane were washed once with Solution I and then with Solution II for 30 min at 65° C. The membranes were covered with plastic wrap and exposed to a phosphorimager screen.

Selection

Clones that showed differences between the (−) and (+) blots were picked (usually 1–8 on each blot pair). A secondary round of reverse northern analysis for confirmation was performed, this time spotting each clone in duplicate on each blot. After phosphorimager analysis, he blots were stripped in 0.1×SSC and 0.5% SDS for 2×15 min at 95° C. and hybridized with a PSA probe (or depending on the hormone that is being used, with a probe for any abundant target genes in the tissue under study). For the clones that were confirmed to be different from PSA, for differential expression in the secondary reverse northern, northern analysis was performed using established protocols. A time course of R1881 induction of LNCaP cells, as well as the CWR22 xenograft model upon androgen ablation (Wainstein, M. A. et al., *Cancer Res.* 54, 6049–6052, 1994) and the androgen-independent CWR22R relapsed xenograft (Nagabhushan, M. et al., *Cancer Res.* 56, 3042–6, 1996), was used.

Sequence Analysis

Sequence analysis was perfomed by the dideoxy chain termination methods using an ABI automated sequencer. Homology search was done using a basic BLAST algorithm. FIG. 3 shows a table of results obtained from the BLAST analysis of isolated clones and their homology to known genes (The cutoff for significant homology was 50% identity).

Isolation of Prostate Cancer Related Genes From LNCaP Cells

The prostate cancer cell line LNCaP was cultured in two batches in culture conditions similar to those previously described (Horoszewicz J S et al., *Cancer Res.* 43: 1809–1818, 1983). The first batch was left untreated, while the second batch was treated with the synthetic androgen R1881 for 24 hrs. Cells from both batches were harvested and total RNA was then isolated from each batch. From the total RNA, polyA$^+$ RNA was obtained using standard procedures, and was used in the Suppression Subtraction Hybridization (SSH; Diatchenko et al., supra) procedure to identify hormone regulated genes. The tester in the SSH procedure was cDNA from untreated cells and the driver was cDNA from R1881-treated cells. The suppression subtraction protocol was performed according to the original description of the method (Diatchenko et al., supra).

Cell Culture

LNCaP, PC-3 and DU-145 cells were routinely maintained and treated as described previously (Korkmaz, K. S. et al., *DNA Cell Biol* 19, 499–506, 2000; Korkmaz, K. S. et al., *Gene* 260, 25–36, 2000).

Xenodraft Studies

Transplantation, growth, and harvesting of tumors from mice bearing the CWR22 and CWR22R xenografts were as previously described (Wainstein, M. A., supra; Nagabhushan, M., supra).

Cloning and Plasmid Construction

A 262 bp cDNA fragment was originally obtained from a screen of a prostate specific library (Ausubel, F. M., et al. (1997) *Current Protocols in Molecular Biology* (John Wiley and Sons, New York) and termed L74. 5' Rapid Amplification of cDNA Ends (RACE) was performed (oligonucleotide sequences available upon request) using the Marathon-Ready cDNA that was prepared from normal prostate tissue (Clontech) and/or SMART-RACE LNCaP cDNA library (Clontech) that was generated according to the manufacturer's recommendations. RACE products were cloned into pCRII-TOPO (Invitrogen), positive clones were confirmed by Southern analysis, and sequenced. In parallel, a λgt10 cDNA library made from a pool of normal human prostates (Clontech) was screened by established procedures to obtain additional clones. Overlapping clones were used to deduce the full-length STMP1 cDNA sequence.

The full-length STMP1 ORF was amplified by using primers centered around the start and stop codons (sequences available upon request) and fused in frame to the C-terminus of green flourescent protein (GFP) using the vector pcDNA3.1-NT-GFP-TOPO (Invitrogen) to generate GFP-STMP1.

Northern Analysis

Total RNA was prepared by the single step guanidine thiocyanate procedure and used in Northern analysis (18). 15 µg of total RNA was used per lane. Probes were generated by random priming and had a specific activity of >3×10$^8$ dpm/µg. A cDNA fragment of STMP1 spanning residues 145–2202 bp was used as probe. Bands were visualized and quantitated by phosphorimager analysis (Molecular Dynamics).

Confocal Microscopy

COS-1 cells were transiently transfected by electroporation using a BTX square-wave pulser at 150 V, 1 ms duration. Cells were grown either on cover slips placed in 6-well tissue culture plates for indirect immunofluorescence or on Lab-Tek Chambered Coverglass (Nalge Nunc International) for live-cell microscopy. Transiently transfected cells were observed 16 h after transfection by Leica TCS-SP confocal microscope. All live-cell experiments were done at 37° C.

Indirect Immunofluorescence

The indirect immunofluorescence was carried out as previously described (Misteli, T. & Spector, D. L. *Mol Cell* 3, 697–705, 1999). The following antibodies were used: anti-β-coat protein (β-COP) antiserum (kindly provided by J. Lippincott-Schwartz), anti-mannosidase II (kindly provided by T. Misteli), anti-TGN46 (Serotec, kindly provided by J. S. Bonifacino), and anti-EEA1 (Affinity Biotechnologies). Texas Red-conjugated secondary antibodies specific for mouse and rabbit were purchased from ICN Biomedicals (Costa Mesa, Calif.).

OTHER EMBODIMENTS

All publications and patent applications mentioned in this specification are herein incorporated by reference to the same extent as if each independent publication or patent application was specifically and individually indicated to be incorporated by reference. While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follow in the scope of the appended claims.

The invention claimed is:

1. An isolated polynucleotide comprising the sequence of SEQ ID NO: 23.

2. The polynucleotide of claim 1, wherein said polynucleotide consists of the sequence of SEQ ID NO: 23.

3. An isolated polynucleotide encoding a polypeptide comprising the sequence of SEQ ID NO: 14.

4. The polynucleotide of claim 3, wherein said polypeptide consists of the sequence of SEQ ID NO: 14.

5. A vector comprising the isolated nucleic acid molecule of claim 1.

6. A vector comprising the nucleic acid molecule of claim 3.

7. An isolated host cell comprising the vector of claim 5.

8. An isolated host cell comprising the vector of claim 6.

9. An isolated host cell comprising the nucleic acid molecule of claim 1.

10. An isolated host cell comprising the nucleic acid molecule of claim 3.

* * * * *

UNITED STATES PATENT AND TRADEMARK OFFICE
CERTIFICATE OF CORRECTION

PATENT NO. : 7,189,565 B2  Page 1 of 1
APPLICATION NO. : 10/239607
DATED : March 13, 2007
INVENTOR(S) : F. Saatcioglu It is certified that error appears in the above-identified patent and that said Letters Patent is hereby corrected as shown below:

Column 4, Line 4, replace "accompany it Typically," with --accompany it. Typically,--.

Column 11, Line 53, replace "4E shows the shows the cDNA" with
 --4E shows the cDNA--.

Column 15, Line 2, replace "minimize their exposure their exposure to" with
 --"minimize their exposure to--.

Column 16, Line 26, replace "cell-", with --cell,--.

Column 18,
 Line 13, replace "be possible slow" with --be possible to slow--; and
 Line 59, replace "an" with --a--.

Column 21, Line 45, replace "thereof Candidate" with --thereof. Candidate--.

Column 32, Line7, replace "immunoflourescence" with --immunofluorescence--.

Column 34,
 Line 52, replace "phoshorimager" with --phosphorimager--; and
 Line 59, replace "he blots" with --the blots--.

Column 35,
 Line 7, replace "was perfomed" with --was performed--; and
 Line 38, replace "Xenodraft" with --Xenograft--.

Signed and Sealed this

Twenty-sixth Day of June, 2007

JON W. DUDAS
*Director of the United States Patent and Trademark Office*